US006469065B1

(12) United States Patent
Garvey et al.

(10) Patent No.: US 6,469,065 B1
(45) Date of Patent: Oct. 22, 2002

(54) NITROSATED AND NITROSYLATED α-ADRENERGIC RECEPTOR ANTAGONIST, COMPOSITIONS AND METHODS OF USE

(75) Inventors: David S. Garvey, Dover; Joseph D. Schroeder, Dedham, both of MA (US); Inigo Saenez de Tejada, Madrid (ES); Ricky D. Gaston, Malden, MA (US); Tatiana E. Shelekhin, Acton, MA (US); Tiansheng Wang, Concord, MA (US)

(73) Assignee: NitroMed, Inc., Bedford, MA (US)

(*) Notice: Subject to any disclaimer, the term of this patent is extended or adjusted under 35 U.S.C. 154(b) by 0 days.

(21) Appl. No.: 09/387,724

(22) Filed: Sep. 1, 1999

Related U.S. Application Data

(63) Continuation-in-part of application No. 09/145,143, filed on Sep. 1, 1998, now Pat. No. 6,294,517, which is a continuation-in-part of application No. 08/714,313, filed on Sep. 18, 1996, now Pat. No. 5,994,294, which is a continuation-in-part of application No. 08/595,732, filed on Feb. 2, 1996, now Pat. No. 5,932,538.

(51) Int. Cl.$^7$ ................... A61K 31/135; A61K 31/21
(52) U.S. Cl. ................... 514/546; 514/506; 514/617; 514/651; 536/103; 540/1; 540/147; 540/155; 548/500; 564/45
(58) Field of Search ................... 514/546, 506, 514/617, 651; 536/103; 540/1; 560/147, 155; 548/500; 564/45

(56) References Cited

U.S. PATENT DOCUMENTS

| 4,127,118 A | 11/1978 | Latorre |
| 4,590,202 A | 5/1986 | Remy ................... 514/392 |
| 4,801,587 A | 1/1989 | Voss et al. |
| 4,885,173 A | 12/1989 | Stanley et al. |
| 5,059,603 A | 10/1991 | Rubin |
| 5,145,852 A | 9/1992 | Virag |
| 5,190,967 A | 3/1993 | Riley |
| 5,236,904 A | 8/1993 | Gerstenberg et al. |
| 5,256,652 A | 10/1993 | El-Rashidy |
| 5,281,607 A | 1/1994 | Stone et al. ................... 514/280 |
| 5,380,758 A | 1/1995 | Stamler et al. |
| 5,399,581 A | 3/1995 | Laragh |
| 5,403,847 A | 4/1995 | Gluchowski et al. ....... 514/318 |
| 5,439,938 A | 8/1995 | Snyder et al. |
| 5,447,912 A | 9/1995 | Gerstenberg et al. |
| 5,451,609 A | 9/1995 | Bellamy et al. ............ 514/651 |
| 5,474,535 A | 12/1995 | Place et al. |
| 5,492,911 A | 2/1996 | Stief |
| 5,498,623 A | 3/1996 | Karjalainen et al. ........ 514/396 |
| 5,543,430 A | 8/1996 | Kaesemeyer |
| 5,565,466 A | 10/1996 | Gioco et al. |
| 5,567,706 A | 10/1996 | Gavras |
| 5,574,068 A | 11/1996 | Stamler et al. |
| 5,578,611 A | 11/1996 | Gluchowski et al. ....... 514/318 |
| 5,583,144 A | 12/1996 | Kral |
| 5,593,876 A | 1/1997 | Stamler et al. |
| 5,612,314 A | 3/1997 | Stamler et al. |
| 5,635,204 A | 6/1997 | Gevirtz et al. ............ 424/449 |
| 5,646,181 A | 7/1997 | Fung et al. |
| 5,648,393 A | 7/1997 | Stamler et al. |
| 5,698,589 A | 12/1997 | Allen |
| 5,731,339 A | 3/1998 | Lowrey |
| 5,767,160 A | 6/1998 | Kaesemeyer |
| 5,773,457 A | 6/1998 | Nahoum |
| 5,789,442 A | 8/1998 | Garfield et al. |
| 5,877,216 A | 3/1999 | Place et al. |

FOREIGN PATENT DOCUMENTS

| EP | 0346297 | 12/1989 |
| EP | 0357581 | 3/1990 |
| EP | 0432199 | 6/1991 |
| FR | 2547501 | 12/1984 |
| JP | 8026962 | 1/1998 |
| WO | 97/27749 | * 8/1997 |
| WO | 9727749 | 8/1997 |
| WO | 9742946 | 11/1997 |
| WO | 9852569 | 11/1998 |
| WO | 9901132 | 1/1999 |
| WO | 9907353 | 2/1999 |
| WO | 9907695 | 2/1999 |
| WO | 9925345 | 5/1999 |
| WO | 9930697 | 6/1999 |

OTHER PUBLICATIONS

Buvat et al, The Journal of Urology, 141 (6):1364–1367 (1989).
Costa et al, The Journal of Urology, 149:301–305 (1993).
Burnett, The Journal of Urology, 157:320–324 (1997).

(List continued on next page.)

*Primary Examiner*—Bennett Celsa
(74) *Attorney, Agent, or Firm*—Hale and Dorr LLP

(57) ABSTRACT

The present invention describes novel nitrosated and/or nitrosylated α-adrenergic receptor antagonists, and novel compositions containing at least one nitrosated and/or nitrosylated α-adrenergic receptor antagonist, and, optionally, one or more compounds that donate, transfer or release nitric oxide, elevate endogenous levels of endothelium-derived relaxing factor, stimulate endogenous synthesis of nitric oxide or are a substrate for nitric oxide synthase, and/or one or more vasoactive agents. The present invention also provides novel compositions containing at least one α-adrenergic receptor antagonist, and one or more compounds that donate, transfer or release nitric oxide, elevate endogenous levels of endothelium-derived relaxing factor, stimulate endogenous synthesis of nitric oxide or is a substrate for nitric oxide synthase and/or one or more vasoactive agents. The present invention also provides methods for treating or preventing sexual dysfunctions in males and females, for enhancing sexual responses in males and females, and for treating or preventing benign prostatic hyperplasia, hypertension, congestive heart failure, variant (Printzmetal) angina, glaucoma, neurodegenerative disorders, vasospastic diseases, cognitive disorders, urge incontinence, or overactive bladder, and for reversing the state of anesthesia.

19 Claims, 11 Drawing Sheets

OTHER PUBLICATIONS

Buvat et al, The Journal of Urology, 159:116–119 (Jan. 1998).

Saenz de Tejada et al, The Journal of Pharmacology and Experimental Therapeutics, 290(1):121–128 (1999).

Mathers et al, *European Urology,* 35(suppl 2):67 (abstract 266) (1999).

RBI/Sigma Catalog, p. 354 (1999).

The Merck Index, 12th Edition, pp. 132, 1727 and 1728 (1996).

Physicians' Desk Reference, 48th Edition, pp. 1146–1147 (1994).

Zorgniotti et al, *Int. J. Impotence Res.,* 6:33–36 (1994).

Trigo–Rocha et al, *Neuroulogy and Urodynamics,* 13:71–80 (1994).

Sonda et al, *Journal of Sex & Marital Therapy,* 16(1):15–21 (1990).

Marquer et al, *Fundam Clin Pharmacol,* 12:377–387 (1998).

* cited by examiner

Dose (Example 10)

NITROSATED AND NITROSYLATED α-ADRENERGIC RECEPTOR ANTAGONIST, COMPOSITIONS AND METHODS OF USE

RELATED APPLICATIONS

This application is a continuation-in-part of U.S. application Ser. No. 09/145,143, filed Sep. 1, 1998, now U.S. Pat. No. 6,294,517 which is a continuation-in-part of U.S. application Ser. No. 08/714,313, filed Sep. 18, 1996, issued as U.S. Pat. No. 5,994,294, which is a continuation-in-part of U.S. application Ser. No. 08/595,732, filed Feb. 2, 1996, issued as U.S. Pat. No. 5,932,538.

FIELD OF THE INVENTION

The present invention describes novel nitrosated and/or nitrosylated α-adrenergic receptor antagonists, and novel compositions comprising at least one nitrosated and/or nitrosylated α-adrenergic receptor antagonist, and, optionally, at least one compound that donates, transfers or releases nitric oxide, elevates endogenous levels of endothelium-derived relaxing factor, stimulates endogenous synthesis of nitric oxide or is a substrate for nitric oxide synthase, and/or at least one vasoactive agent. The present invention also provides novel compositions comprising at least one α-adrenergic receptor antagonist, and at least one compound that donates, transfers or releases nitric oxide, elevates endogenous levels of endothelium-derived relaxing factor, stimulates endogenous synthesis of nitric oxide or is a substrate for nitric oxide synthase, and/or at least one vasoactive agent. The present invention also provides methods for treating or preventing sexual dysfunctions in males and females, for enhancing sexual responses in males and females, and for treating or preventing benign prostatic hyperplasia, hypertension, congestive heart failure, variant (Printzmetal) angina, glaucoma, neurodegenerative disorders, vasospastic diseases, cognitive disorders, urge incontinence, and overactive bladder, and methods for reversing the state of anesthesia.

BACKGROUND OF THE INVENTION

Adequate sexual function is a complex interaction of hormonal events and psychosocial relationships. There are four stages to sexual response as described in the *International Journal of Gynecology & Obstetrics*, 51(3):265–277 (1995). The first stage of sexual response is desire. The second stage of sexual response is arousal. Both physical and emotional stimulation may lead to breast and genital vasodilation and clitoral engorgement (vasocongestion). In the female, dilation and engorgement of the blood vessels in the labia and tissue surrounding the vagina produce the "orgasmic platform," an area at the distal third of the vagina where blood becomes sequestered. Localized perivaginal swelling and vaginal lubrication make up the changes in this stage of sexual response. Subsequently, ballooning of the proximal portion of the vagina and elevation of the uterus occurs. In the male, vasodilation of the cavernosal arteries and closure of the venous channels that drain the penis produce an erection. The third stage of sexual response is orgasm, while the fourth stage is resolution. Interruption or absence of any of the stages of the sexual response cycle can result in sexual dysfunction. One study found that 35% of males and 42% of females reported some form of sexual dysfunction. Read et al, *J. Public Health Med.*, 19(4): 387–391 (1997).

While there are obvious differences in the sexual response between males and females, one common aspect of the sexual response is the erectile response. The erectile response in both males and females is the result of engorgement of the erectile tissues of the genitalia with blood which is caused by the relaxation of smooth muscles in the arteries serving the genitalia.

In both pre-menopausal and menopausal females, sexual dysfunction can include, for example, sexual pain disorders, sexual desire disorders, sexual arousal dysfunction, orgasmic dysfunction, dyspareunia, and vaginismus. Sexual dysfunction can be caused, for example, by pregnancy, menopause, cancer, pelvic surgery, chronic medical illness or medications.

In males, some pharmacological methods of treating sexual dysfunctions are available, however, such methods have not proven to be highly satisfactory or without potentially severe side-effects. Papaverine now widely used to treat impotence, is generally effective in cases where the dysfunction is psychogenic or neurogenic and where severe atherosclerosis is not involved. Injection of papaverine, a smooth muscle relaxant, or phenoxybenzamine, a non-specific antagonist and hypotensive, into corpus cavernosum has been found to cause an erection sufficient for vaginal penetration, however, these treatments are not without the serious and often painful side effect of priapism. Also, in cases where severe atherosclerosis is not a cause of the dysfunction, intracavernosal injection of phentolamine, an α-adrenergic antagonist, is used. As an alternative or, in some cases, as an adjunct to α-adrenergic blockade, prostaglandin $E_1$ ($PGE_1$) has been administered via intracavernosal injection. A major side effect frequently associated with intracorparally delivered $PGE_1$ is penile pain and burning.

The use of α-adrenergic receptor antagonists for the treatment and prevention of benign prostatic hyperplasia, hypertension, congestive heart failure, variant (Printzmetal) angina, glaucoma, neurodegenerative disorders, vasospastic diseases, cognitive disorders, urge incontinence, and overactive bladder, and for reversing the state of anesthesia has been described. For example, U.S. Pat. Nos. 5,403,847, and 5,578,611, and WO 99/25345 describe treating benign prostatic hyperplasia with specific compounds; Stanaszek et al., *Drugs*, 25(4): 339–384 (1983) reviews the use of α-adrenergic receptor antagonists to treat hypertension and congestive heart failure; Goodman and Gilman, The Pharmacological Basis of Therapeutics (9th Ed.), McGraw-Hill, Inc. (1995), describe the use of α-adrenergic receptor antagonists to treat variant (Printzmetal) angina and vasospastic diseases, such as Raynaud's disease; U.S. Pat. No. 4,590,202 and WO 99/07353 describe the use of adrenergic receptor antagonists in glaucoma therapy; U.S. Pat. No. 5,498,623 describes the treatment of cognitive disorders such as endogenous depression, age dependent memory impairment, and Alzheimer's disease; U.S. Pat. No. 5,281,607 describes the treatment of numerous neurodegenerative diseases, such as infantile spinal muscular atrophy, juvenile spinal muscular atrophy, hypokinetic movement disorder, Down's Syndrome in middle age, and senile dementia of Lewy body type; Sereis et al., *Neurourol. Urodyn.*, 31–36 (1998) describes the treatment of urge incontinence in women; Wein, *Urology*, 43–47, (1998) describes the treatment of overactive bladder; and U.S. Pat. No. 5,635,204 discloses reversing the state of anesthesia.

There is a need in the art for new and improved treatments of sexual dysfunctions, and other diseases. The present invention is directed to these, as well as other, important ends.

SUMMARY OF THE INVENTION

Nitric oxide (NO) has been shown to mediate a number of actions, including the bactericidal and tumoricidal actions of macrophages and blood vessel relaxation of endothelial cells. NO and NO donors have also been implicated as mediators of nonvascular smooth muscle relaxation. As described herein, this effect includes the dilation of the corpus cavernous smooth muscle, an event involved in the sexual response process in both males and females. The effects of modified α-adrenergic receptor antagonists which are directly or indirectly linked with a nitric oxide adduct, and which are optionally used in conjunction with NO donors, have not been previously investigated.

In arriving at the present invention it was recognized that the risk of toxicities and adverse effects that are associated with high doses of α-adrenergic receptor antagonists can be avoided by the use of nitrosated and/or nitrosylated α-adrenergic receptor antagonists or by the use of at least one α-adrenergic receptor antagonist in combination with at least one nitric oxide donor. Such toxicities and adverse effects include postural hypotension, reflex tachycardia and other arrhythmias, syncope and, with respect to the ergot alkaloids, nausea and vomiting and, upon prolonged or excessive administration, vascular insufficiency and gangrene of the extremities. The smooth muscle relaxant properties of the α-adrenergic receptor antagonists and of compounds that donate, release or transfer nitrogen monoxide or elevate levels of endogenous nitric oxide or endothelium-derived relaxing factor (EDRF) or are substrates for nitric oxide synthase work together to permit the same efficacy with lower doses of the α-adrenergic receptor antagonists or work synergistically to produce an effect that is greater than the additive effects of the α-adrenergic receptor antagonist and the compound that donates, releases or transfers nitrogen monoxide or elevate levels of endogenous nitric oxide or EDRF or is a substrate for nitric oxide synthase.

One aspect of the present invention provides novel nitrosated and/or nitrosylated α-adrenergic receptor antagonists. The α-adrenergic receptor antagonists can be nitrosated and/or nitrosylated through one or more sites such as oxygen (hydroxyl condensation), sulfur (sulfhydryl condensation), carbon and/or nitrogen. The present invention also provides compositions comprising a therapeutically effective amount of such compounds in a pharmaceutically acceptable carrier.

Another aspect of the present invention provides compositions comprising a therapeutically effective amount of at least one α-adrenergic receptor antagonist, that is optionally substituted with at least one NO and/or $NO_2$ group (i.e., nitrosylated and/or nitrosated), and at least one compound that donates, transfers or releases nitrogen monoxide as a charged species, i.e., nitrosonium ($NO^+$) or nitroxyl ($NO—$), or as the neutral species, nitric oxide (NO.), and/or stimulates endogenous production of nitric oxide or EDRF in vivo and/or is a substrate for nitric oxide synthase. The present invention also provides for such compositions in a pharmaceutically acceptable carrier.

Yet another aspect of the present invention provides compositions comprising a therapeutically effective amount of at least one α-adrenergic receptor antagonist, that is optionally substituted with at least one NO and/or $NO_2$ group (i.e., nitrosylated and/or nitrosated), at least one vasoactive drug, and, optionally, at least one compound that donates, transfers or releases nitrogen monoxide as a charged species, i.e., nitrosonium ($NO^+$) or nitroxyl ($NO—$), or as the neutral species, nitric oxide (NO.), and/or stimulates endogenous production of nitric oxide or EDRF in vivo and/or is a substrate for nitric oxide synthase. The invention also provides for such compositions in a pharmaceutically acceptable carrier.

Yet another aspect of the present invention provides methods for treating and/or preventing sexual dysfunctions and/or enhancing sexual responses in patients, including males and females, by administering to a patient in need thereof a therapeutically effective amount of at least one nitrosated and/or nitrosylated α-adrenergic receptor antagonist and, optionally, at least one compound that donates, transfers or releases nitric oxide as a charged species, i.e., nitrosonium ($NO^+$) or nitroxyl ($NO—$), or as the neutral species, nitric oxide (NO.), and/or stimulates endogenous production of nitric oxide or EDRF in vivo and/or is a substrate for nitric oxide synthase. The methods can further comprise administering a therapeutically effective amount of at least one vasoactive agent. Alternatively, the methods for treating and/or preventing sexual dysfunctions and/or enhancing sexual responses in patients, including males and females, can comprise administering a therapeutically effective amount of at least one nitrosated and/or nitrosylated α-adrenergic receptor antagonist, at least one vasoactive agent, and, optionally, at least one compound that donates, transfers or releases nitric oxide as a charged species, i.e., nitrosonium ($NO^+$) or nitroxyl ($NO—$), or as the neutral species, nitric oxide (NO.), and/or stimulates endogenous production of nitric oxide or EDRF in vivo and/or is a substrate for nitric oxide synthase. The nitrosated and/or nitrosylated α-adrenergic receptor antagonists, nitric oxide donors, and/or vasoactive agents can be administered separately or as components of the same composition in one or more pharmaceutically acceptable carriers.

The present invention also provides methods for treating and/or preventing sexual dysfunctions and/or enhancing sexual responses in patients, including males and females, by administering to a patient in need thereof a therapeutically effective amount of at least one α-adrenergic receptor antagonist and at least one compound that donates, transfers or releases nitric oxide as a charged species, i.e., nitrosonium ($NO^+$) or nitroxyl ($NO—$), or as the neutral species, nitric oxide (NO.), and/or stimulates endogenous production of nitric oxide or EDRF in vivo and/or is a substrate for nitric oxide synthase. The methods can further comprise administering a therapeutically effective amount of at least one vasoactive agent. Alternatively, the methods for treating and/or preventing sexual dysfunctions and/or enhancing sexual responses in patients, including males and females, can comprise administering a therapeutically effective amount of at least one cc-adrenergic receptor antagonist, at least one vasoactive agent, and, optionally, at least one compound that donates, transfers or releases nitric oxide as a charged species, i.e., nitrosonium ($NO^+$) or nitroxyl ($NO—$), or as the neutral species, nitric oxide (NO.), and/or stimulates endogenous production of nitric oxide or EDRF in vivo and/or is a substrate for nitric oxide synthase. The α-adrenergic receptor no antagonists, the nitric oxide donors, and the vasoactive agents can be administered separately or as components of the same composition in one or more pharmaceutically acceptable carriers.

The present invention also provides methods using the compounds and compositions described herein to prevent or treat benign prostatic hyperplasia, hypertension, congestive heart failure, variant (Printzmetal) angina, glaucoma, neurodegenerative disorders, vasospastic diseases, cognitive disorders, urge incontinence, or overactive bladder, or to reverse the state of anesthesia by administering to a patient in need thereof a therapeutically effective amount of at least one of the compounds and/or compositions described herein. In these methods, the α-adrenergic receptor antagonists that are optionally nitrosated and/or nitrosylated, nitric oxide donors and vasoactive agents can be administered separately or as components of the same composition in one or more pharmaceutically acceptable carriers.

These and other aspects of the present invention are described in detail herein.

DETAILED DESCRIPTION OF THE INVENTION

Figure 1:
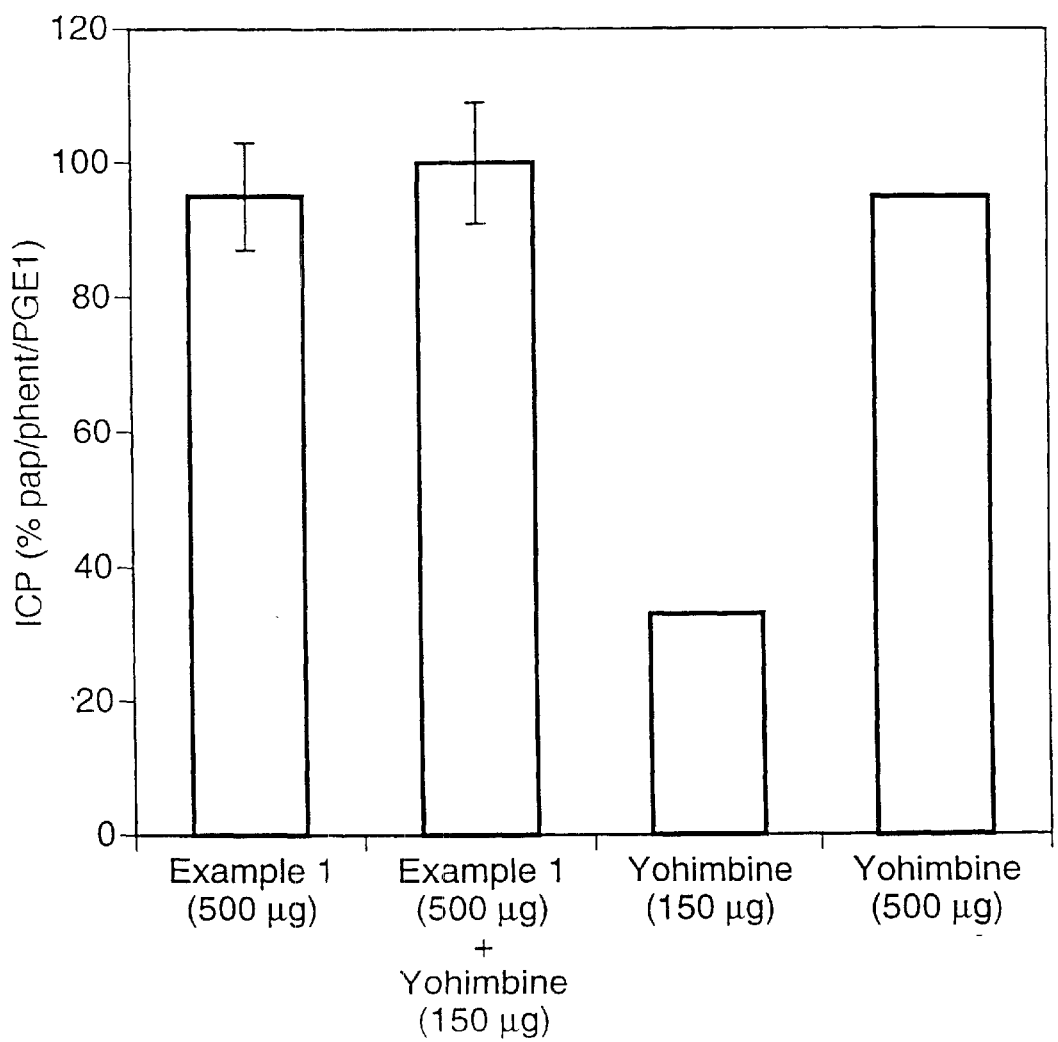
FIG. 1 shows the percent peak erectile response in vivo compared to that produced by 150 μl of pap/phent/PGE1 (30 mg/ml:1 mg/ml:10 μg/ml) in the anesthetized rabbit following the intracavemosal injection of 150 μp of yohimbine (150 μg, 500 μg), Example 1 (500 μg), and a combination of yohimbine (150 μg) and Example 1 (500 μg). The ordinate is the percent response of intracavemosal pressure relative to that produced by pap/phent/PGE1 and the abscissa indicates the various drugs given.

The following definitions may be used throughout the specification. "α-adrenergic receptor antagonists" refers to any compound that reversibly or irreversibly blocks the activation of any α-adrenergic receptor.

"Patient" refers to animals, preferably mammals, more preferably humans.

"Transurethral" or "intraurethral" refers to delivery of a drug into the urethra, such that the drug contacts and passes through the wall of the urethra and enters into the blood stream.

"Transdermal" refers to the delivery of a drug by passage through the skin and into the blood stream.

"Transmucosal" refers to delivery of a drug by passage of the drug through the mucosal tissue and into the blood stream.

"Penetration enhancement" or "permeation enhancement" refers to an increase in the permeability of the skin or mucosal tissue to a selected pharmacologically active agent such that the rate at which the drug permeates through the skin or mucosal tissue is increased.

"Carriers" or "vehicles" refers to carrier materials suitable for drug administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, NO.), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, NO—, NO.), such that the biological activity of the nitrogen monoxide species is expressed at the intended site of action.

"Nitric oxide donor" or "NO donor" refers to compounds that donate, release and/or directly or indirectly transfer a nitric oxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, an alkenyl group, an alkynyl group, a bridged cycloalkyl group, a cycloalkyl group or a heterocyclic ring, as defined herein.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$–$C_{10}$ hydrocarbon (preferably a $C_2$–$C_8$ hydrocarbon, more preferably a $C_2$–$C_6$ hydrocarbon) which can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Alkynyl" refers to an unsaturated acyclic $C_2$–$C_{10}$ hydrocarbon (preferably a $C_2$–$C_8$ hydrocarbon, more preferably a $C_2$–$C_6$ hydrocarbon) which can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo[3.3.0] octane, 7-oxabycyclo[2.2.1]heptyl and the like.

"Cycloalkyl" refers to an alicyclic group comprising from about 3 to about 7 carbon atoms. Cycloalkyl groups can be unsubstituted or substituted with one, two or three substituents independently selected from alkyl, alkoxy, amino, alkylamino, dialkylamino, arylamino, diarylamino. alkylarylamino, aryl, amidyl, ester, hydroxy, halo, carboxyl, alkylcarboxylic acid, alkylcarboxylic ester, carboxamido, alkylcarboxamido, oxo and nitro. Exemplary cycloalkyl groups include cyclopropyl, cyclobutyl, cyclopentyl, cyclohexyl, and the like.

"Heterocyclic ring or group" refers to a saturated or unsaturated cyclic hydrocarbon group having about 2 to about 10 carbon atoms (preferably about 4 to about 6 carbon atoms) where 1 to about 3 carbon atoms are replaced by one or more nitrogen, oxygen and/or sulfur atoms. The heterocyclic ring or group can be fused to an aromatic hydrocarbon group. Heterocyclic groups can be unsubstituted or substituted with one, two or three substituents independently selected from alkyl, alkoxy, amino, alkylamino, dialkylamino, arylamino, diarylamino. alkylarylamino, hydroxy, oxo, halo, carboxyl, alkylcarboxylic acid, alkylcarboxylic ester, aryl, amidyl, ester, carboxamido, alkylcarboxamido, arylcarboxamido, and nitro. Exemplary heterocyclic groups include pyrrolyl, pyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, 2-pyrrolinyl, 3-pyrrolinyl, pyrrolindinyl, oxazolindinyl 1,3-dioxolanyl, 2-imidazonlinyl, imidazolindinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronatphthtyl, furanyl, indanyl, indenyl, indoyl, and the like. Aryl groups (including bicylic aryl groups) can be unsubstituted or substituted with one, two or three substituents independently selected from alkyl, alkoxy, amino, alkylamino, dialkylamino, arylamino, diarylamino. alkylarylamino, hydroxy, alkylcarboxylic acid, alkylcarboxylic ester, aryl, amidyl, ester, carboxamido, alkylcarboxamido and nitro. Exemplary substituted aryl groups include tetrafluorophenyl, pentafluorophenyl, and the like.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein.

"Cycloalkylalkyl" refers to a cycloalkyl radical, as defined herein, attached to an alkyl radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkoxy" refers to $R_{50}O$—, wherein $R_{50}$ is an alkyl group, as defined herein. Exemplary alkoxy groups include methoxy, ethoxy, t-butoxy, cyclopentyloxy, and the like.

"Arylalkoxy or alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl refers to an alkoxy group, as defined herein, appended to a haloalkyl group, as defined herein. Exemplary alkoxyhaloalkyl groups include 4 methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Haloalkoxy" refers to a haloalkyl group, as defined herein, to which is appended an alkoxy group, as defined herein. Exemplary haloalkyl groups include 1,1,1-trichloroethoxy, 2-bromobutoxy, and the like.

"Hydroxy" refers to —OH.

"Oxo" refers to =O.

"Hydroxyalkyl" refers to a hydroxy group, as defined herein, appended to an alkyl group, as defined herein.

"Amino" refers to —NH$_2$.

"Nitrate" refers to —O—NO$_2$.

"Nitrite" refers to —O—NO.

"Thionitrate" refers to —S—NO$_2$.

"Thionitrite" and "nitrosothiol" refer to —S—NO.

"Nitro" refers to the group —NO$_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Alkylamino" refers to $R_{50}$NH—, wherein $R_{50}$ is an alkyl group, as defined herein. Exemplary alkylamino groups include methylamino, ethylamino, butylamino, cyclohexylamino, and the like.

"Arylamino" refers to $R_{55}$NH—, wherein $R_{55}$ is an aryl group, as defined herein.

"Dialkylamino" refers to $R_{52}R_{53}$N—, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}$N—, wherein $R_{55}$ and $R_{60}$ are each independently an aryl group, as defined herein.

"Alkylarylamino" refers to $R_{52}R_{55}$N—, wherein $R_{52}$ is an alkyl group, as defined herein and $R_{55}$ is an aryl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein.

"Aminoaryl" refers to an amino group, an alkylamino group, a dialkylamino group, an arylamino group, a diarylamino group, an alkylarylamino group or a heterocyclic ring, as defined herein, to which is appended an aryl group, as defined herein.

"Sulfinyl" refers to —S(O)—.

"Sulfonyl" refers to —S(O)$_2$—.

"Sulfonic acid" refers to —S(O)$_2$OH

"Alkylsulfonic acid" refers to a sulfonic acid group, as defined herein, appended to an alkyl group, as defined herein.

"Arylsulfonic acid" refers to an sulfonic acid group, as defined herein, appended to an aryl group, as defined herein "Sulfonic ester" refers to —S(O)$_2$OR$_{58}$, wherein $R_{58}$ is an alkyl group, an aryl group, an alkylaryl group or an aryl heterocyclic ring, as defined herein.

"Sulfonamido" refers to —S(O)$_2$—N(R$_{51}$)(R$_{57}$), wherein $R_{51}$ and $R_{57}$ are each independently a hydrogen atom, an alkyl group, an aryl group, an alkylaryl group, or an arylheterocyclic ring, as defined herein, and $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}$S—, wherein $R_{50}$ is an alkyl group, as defined herein.

"Arylthio" refers to $R_{55}$S—, wherein $R_{55}$ is an aryl group, as defined herein.

"Alkylsulfinyl" refers to $R_{50}$—S(O)—, wherein $R_{50}$ is an alkyl group, as defined herein.

"Alkylsulfonyl" refers to $R_{55}$—S(O)$_2$—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—S(O)$_2$—, wherein $R_{55}$ is an aryl group, as defined herein.

"Amidyl" refers to $R_{51}$C(O)N(R$_{57}$)— wherein $R_{51}$ and $R_{57}$ are each independently a hydrogen atom, an alkyl group, an aryl group, an alkylaryl group, or an arylheterocyclic ring, as defined herein.

"Ester" refers to $R_{51}$C(O)O— wherein $R_{51}$ is a hydrogen atom, an alkyl group, an aryl group, an alkylaryl group, or an arylheterocyclic ring, as defined herein.

"Carbamoyl" refers to —O—C(O)N(R$_{51}$)(R$_{57}$), wherein $R_{51}$ and $R_{57}$ are each independently a hydrogen atom, an alkyl group, an aryl group, an alkylaryl group or an aryl-heterocyclic ring, as defined herein, and $R_{51}$ and $R_{57}$ when taken together are a heterocyclic ring, a cycloalkyl group or a bridged cycloalkyl group, as defined herein.

"Carboxyl" refers to —CO$_2$H.

"Carbonyl" refers to —C(O)—.

"Methanthial" refers to —C(S)—.

"Carboxylic ester" refers to —C(O)OR$_{58}$, wherein $R_{58}$ is an alkyl group, an aryl group, an alkylaryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" refers to an aryl group, as defined herein, appended to a carboxylic ester group, as defined herein. "Carboxamido" refers to —C(O)N(R$_{51}$)(R$_{57}$), wherein $R_{51}$ and $R_{57}$ are each independently a hydrogen atom, an alkyl group, an aryl group, an alkylaryl group or an arylheterocyclic ring, as defined herein, and $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N(R$_{58}$)—C(O)N(R$_{51}$)(R$_{57}$) wherein $R_{51}$, $R_{57}$, and $R_{58}$ are each independently a hydrogen atom, an alkyl group, an aryl group, an alkylaryl group, or an arylheterocyclic ring, as defined herein, and $R_{51}$ and $R_{57}$ when taken together are a heterocyclic ring, a cycloalkyl group or a bridged cycloalkyl group, as defined herein.

"Phosphoryl" refers to —P(R$_{70}$)(R$_{71}$)(R$_{72}$), wherein $R_{70}$ is a lone pair of electrons, sulfur or oxygen, and $R_{71}$ and $R_{72}$ are each independently a covalent bond, a hydrogen, a lower alkyl, an alkoxy, an alkylamino, a hydroxy or an aryl, as defined herein.

"Silyl" refers to —Si($R_{73}$)($R_{74}$), wherein $R_{73}$ and $R_{74}$ are each independently a covalent bond, a lower alkyl, an alkoxy, an aryl or an arylalkoxy, as defined herein.

The term "sexual dysfunction" generally includes any sexual dysfunction in a patient, including an animal, preferably a mammal, more preferably a human. The patient can be male or female. Sexual dysfunctions can include, for example, sexual desire disorders, sexual arousal disorders, orgasmic disorders and sexual pain disorders. Female sexual dysfunction refers to any female sexual dysfunction including, for example, sexual desire disorders, sexual arousal dysfunctions, orgasmic dysfunctions, sexual pain disorders, dyspareunia, and vaginismus. The female can be pre-menopausal or menopausal. Male sexual dysfunction refers to any male sexual dysfunctions including, for example, male erectile dysfunction and impotence.

The present invention is directed to the treatment and/or prevention of sexual dysfunctions in patients, including males and females, by administering the compounds and compositions described herein. The present invention is also directed to enhancing sexual responses in patients, including males and females, by administering the compounds and/or compositions described herein. The novel compounds and novel compositions of the present invention are described in more detail herein.

The α-adrenergic receptor antagonists that are nitrosated or nitrosylated in accordance with the invention and/or are included in the compositions of the invention can be any of those known in the art, including those exemplified below. Structurally, the α-antagonists can generally be categorized as haloalkylamines, imidazolines, quinozolines, indole derivatives, phenoxypropanolamines, alcohols, alkaloids, amines, piperizines, piperidines and amides.

The first group of α-adrenergic receptor antagonists are the haloalkylamines that irreversibly block $α_1$- and $α_2$-adrenergic receptors. Included in this group are, for example, phenoxybenzamine and dibenamine. Phenoxybenzamine is used in the treatment of pheochromocytomas, tumors of the adrenal medulla and sympathetic neurons that secrete catecholamines into the circulation. It controls episodes of severe is hypertension and minimizes other adverse effects of catecholamines such as contraction of plasma volume and injury of the myocardium.

Another group of α-adrenergic receptor antagonists are the imidazolines. These include phentolamine and tolazoline. Phentolamine has similar affinity for $α_1$ and $α_2$ receptors. Phentolamine is used in short-term control of hypertension in patients with pheochromocytoma and direct, intracavernous injection of phentolamine (usually in combination with papaverine) has been proposed as a treatment for male sexual dysfunction. Tolazoline is used in the treatment of persistent pulmonary hypertension in neonates. Other imidazolines include, for example, idazoxan, deriglidole, RX 821002, BRL 44408 and BRL 44409 (see, Young et al, *Eur. J. Pharm.*, 168:381–386 (1989), the disclosure of which is incorporated herein by reference).

Another group of α-adrenergic receptor antagonists that are contemplated are the quinazolines. These include, for example, prazosine, a very potent and selective $α_1$-adrenergic antagonist, terazosin, doxazosin, alfuzosin, bunazosin, ketanserin, trimazosin and abanoquil. This group of compounds is principally used in the treatment of primary systemic hypertension and also in the treatment of congestive heart failure.

Another class of α-adrenergic receptor antagonists are indoles and indole derivatives. These include, for example, carvedilol and BAM 1303. Another class of α-adrenergic receptor antagonists are alcohols. These include, for example, labetelol and ifenprodil.

Another class of α-adrenergic receptor antagonists are alkaloids. These include, for example, "ergotoxine" which is a mixture of three alkaloids: ergocornine, ergocristine and ergocryptine. Both natural and dihydrogenated peptide alkaloids produce α-adrenergic blockade. The principal uses are to stimulate contraction of the uterus post-partum and to relieve the pain of migraine headaches. Another indole alkaloid is yohimbine. This compound is a competitive antagonist that is selective for $α_2$-adrenergic receptors. In humans, it has been observed to increase blood pressure and heart rate and has been used in the treatment of male sexual dysfunction. Other alkaloid α-adrenergic receptor antagonists include rauwolscine, corynathine, raubascine, tetrahydroalstonine, apoyohimbine, akuammigine, β-yohimbine, yohimbol, pseudoyohimbine, epi-3α-yohimbine, 10-hydroxy-yohimbine and 11-hydroxy-yohimbine. The indole alkaloids are typically obtained from plant extracts or tree barks.

Another class of α-adrenergic receptor antagonists are amines. These include, for example, tamsulosin, benoxathian, atipamezole, BE 2254, WB 4101, HU-723, tedisamil, mirtazipine, setiptiline, reboxitine and delequamine.

Another class of α-adrenergic receptor antagonists are piperizines, which include, for example, naftopil, saterinone, SL 89.0591, ARC 239, urapidil, 5-methylurapidil and monatepi. Urapidil is a selective $α_1$-adrenergic antagonist that has a hypotensive effect in humans.

Another class of α-adrenergic receptor antagonists are piperidines. These include, for example, haloperidol.

Another class of α-adrenergic receptor antagonists are amides, such as indoramin and SB 216469. Indoramin is a selective, competitive $α_1$-antagonist that has been used for the treatment of hypertension.

Other α-adrenergic receptor antagonists include moxisylyte, trazodone, dapiprozole, efaroxan, Recordati 15/2739, SNAP 1069, SNAP 5089, SNAP 5272, RS 17053, SL 89.0591, KMD 3213, spiperone, AH 11110A, chloroethylclonidine, BMY 7378 and niguldipine.

Sources of information for these compounds include Goodman and Gilman, The Pharmacological Basis of Therapeutics (9th Ed.), McGraw-Hill, Inc. (1995), The Physician's Desk Reference (49th Ed.), Medical Economics (1995), Drug Facts and Comparisons (1993 Ed), Facts and Comparisons (1993), and The Merck Index (12th Ed.), Merck & Co., Inc. (1996), the disclosures of each of which are incorporated herein by reference in their entirety.

In one embodiment, the present invention describes nitrosated and/or nitrosylated α-adrenergic receptor antagonists of Formula (I):

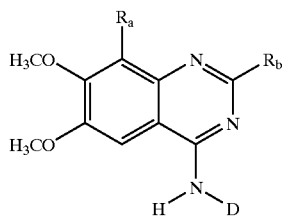

wherein $R_a$ is a hydrogen or an alkoxy;

$R_b$ is:

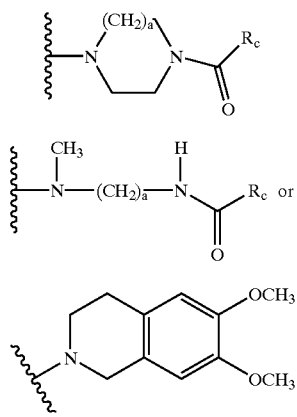

a is an integer of 2 or 3;

$R_c$ is a heterocyclic group, a lower alkyl group, a hydroxyalkyl group, or an arylheterocyclic ring;

D is:
(i) —NO;
(ii) —NO$_2$;
(iii) —C($R_d$)—O—C(O)—Y—Z—(C($R_e$)($R_f$))$_p$—T—(Q;
(iv) —C(O)—Y—Z—(G—(C($R_e$)($R_f$))$_q$—T—Q)$_p$;
(v) —P—Z—(G—(C($R_e$)($R_f$))$_q$—T—Q)$_p$;
(vi) —P—B$_{j}$—V—B$_{r}$—K$_{r}$—E$_{s}$—[C($R_e$)($R_f$)]$_w$—E$_c$—[C($R_e$)($R_f$)]$_x$—K$_d$—[C($R_e$)($R_f$)]$_y$—K$_i$—E$_j$—K$_g$—[C($R_e$)($R_f$)]$_z$—T—Q; or
(vii) —P—F'$_n$—K$_r$—E$_s$—[C($R_e$)($R_f$)]$_w$—E$_c$—[C($R_e$)($R_f$)]$_x$—K$_d$—[C($R_e$)($R_f$)]$_y$—K$_i$—E$_j$—K$_g$—[C($R_e$)($R_f$)]$_z$—T—Q;

wherein $R_d$ is a hydrogen, a lower alkyl, a cycloalkyl, an aryl or an arylalkyl;

Y is oxygen, S(O)$_o$, lower alkyl or NR$_j$;

o is an integer from 0 to 2;

$R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, —CH$_2$—C(T—Q)($R_e$)($R_f$), or —(N$_2$O$_2$$^-$).M$^+$, wherein M$^+$ in an organic or inorganic cation;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, —T—Q, or [C($R_e$)($R_f$)]$_k$—T—Q, or $R_e$ and $R_f$ taken together with the carbon atoms to which they are attached are a carbonyl, a methanthial, a heterocyclic ring, a cycloalkyl group or a bridged cycloalkyl group;

k is an integer from 1 to 3;

p is an integer from 1 to 10;

T is independently a covalent bond, oxygen, S(O)$_o$ or NR$_i$;

Z is a covalent bond, an alkyl, an aryl, an alkylaryl, an arylalkyl, a heteroalkyl, or (C($R_e$)($R_f$))$_p$;

Q is —NO or —NO$_2$;

G is a covalent bond, —T—C(O)—, —C(O)—T— or T;

q' is an integer from 0 to 5;

P is a carbonyl, a phosphoryl or a silyl;

l and t are each independently an integer from 1 to 3;

r, s, c, d, g, i and j are each independently an integer from 0 to 3;

w, x, y and z are each independently an integer from 0 to 10;

B at each occurrence is independently an alkyl, an aryl, or [C($R_e$)($R_f$)]$_p$;

E at each occurrence is independently —T—, an alkyl, an aryl, or —(CH$_2$CH$_2$O)$_q$;

K at each occurrence is independently —C(O)—, —C(S)—, —T—, a heterocyclic ring, an aryl, an alkenyl, an alkynyl, an arylheterocyclic ring, or —(CH$_2$CH$_2$O)$_q$;

q is an integer of from 1 to 5;

V is oxygen, S(O)$_o$, or NK$_i$;

F' at each occurrence is independently B or carbonyl;

n is an integer from 2 to 5;

with the proviso that when $R_i$ is —CH$_2$—C(T—Q)($R_e$)($R_f$) or —(N$_2$O$_2$$^-$).M$^+$, or $R_e$ or $R_f$ are T—Q or [C($R_e$)($R_f$)]$_k$—T—Q then the "—T—Q" subgroup designated in D can be a hydrogen, an alkyl, an alkoxy, an alkoxyalkyl, an aminoalkyl, a hydroxy, or an aryl.

In cases where multiple designations of variables in which reside in sequence are chosen as a "covalent bond" or the integer chosen is 0, the intent is to denote a single covalent bond connecting one radical to another. For example, E$_0$ or [C($R_e$)($R_f$)]$_0$ would denote a covalent bond, while E$_2$ denotes (E—E) and [C($R_e$)($R_f$)]$_2$ denotes —C($R_e$)($R_f$)—C($R_e$)($R_f$)—.

Another embodiment of the present invention describes nitrosated and/or nitrosylated α-adrenergic receptor antagonists of Formula (II):

II

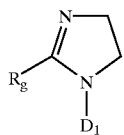

wherein R_g is:

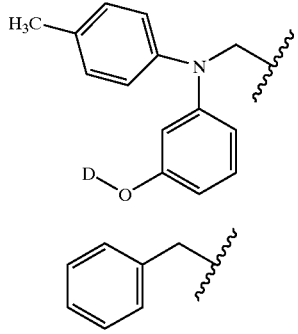 (i)

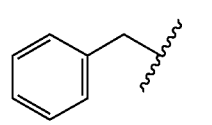 (ii)

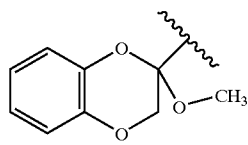 (iii)

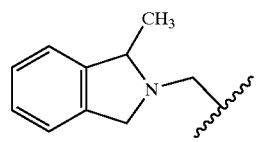 (iv)

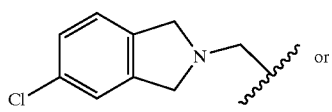 (v)

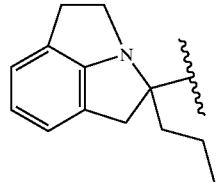 (vi)

wherein $D_1$ is a hydrogen or D, where D is as defined herein, with the proviso that $D_1$ must be D if there is no other D in the compound.

Another embodiment of the present invention describes nitrosated and/or nitrosylated α-adrenergic receptor antagonists of Formula (III):

III

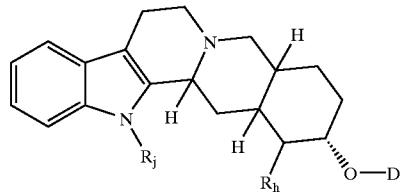

wherein
$R_h$ is a hydrogen, —C(O)—OR$_k$ or —C(O)—X;
$R_k$ is hydrogen or lower alkyl;

X is:

—Y—(C(R$_e$)(R$_f$))$_p$—G$_1$—(C(R$_e$)(R$_f$))$_p$—T—Q or (1)

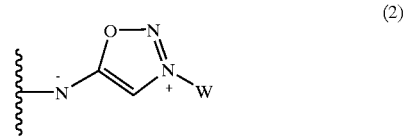 (2)

wherein:
G$_1$ is a covalent bond, —T—C(O)—, —C(O)—T—, or —C(Y—C(O)—R$_m$)—;
R$_m$ is a heterocyclic ring; and
W is a heterocyclic ring or NR$_q$R'$_q$ wherein R$_q$ and R'$_q$ are each independently a lower alkly, an aryl or an alkenyl, and R$_j$ is hydrogen, —D or —(O)CR$_d$; and
wherein Y, R$_e$, R$_f$, p, Q, D, T and R$_d$ are as defined herein.

Another embodiment of the present invention describes nitrosated and/or nitrosylated α-adrenergic receptor antagonists of Formula (IV):

IV

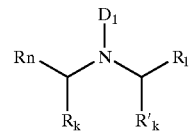

wherein A$_1$ is oxygen or methylene, and X and R$_j$ are as defined herein.

Another embodiment of the present invention describes nitrosated and/or nitrosylated α-adrenergic receptor antagonists of Formula (V):

V

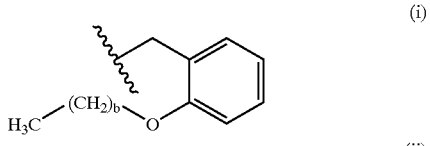

wherein R$_l$ is:

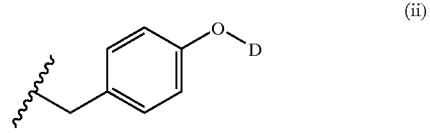 (i)

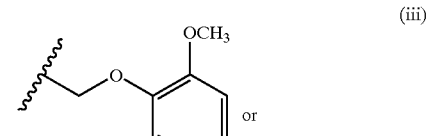 (ii)

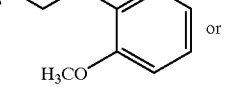 (iii)

or

-continued (iv)
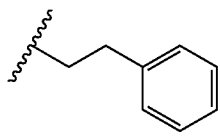

b is an integer of 0 or 1;
$R_n$ is:

(i)
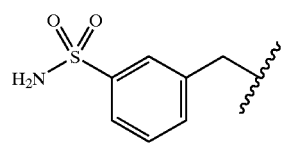

(ii)
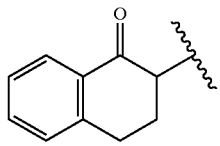

(iii)
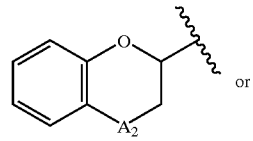

(iv)
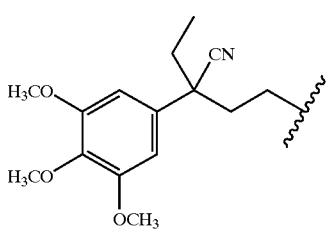

wherein $A_2$ is oxygen or sulfur, $R'_k$ is independently selected from $R_k$, D and $D_1$ are as defined herein; with the proviso that $D_1$ must be D if there is no other D in the compound.

Another embodiment of the present invention describes nitrosated and/or nitrosylated α-adrenergic receptor antagonists of Formula (VI):

VI
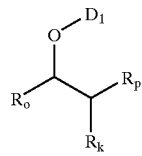

wherein
$R_o$ is:

(i)
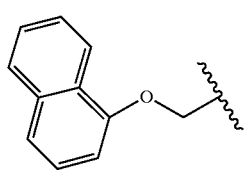

(ii)
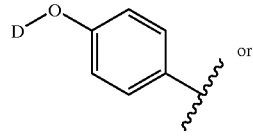

(iii)
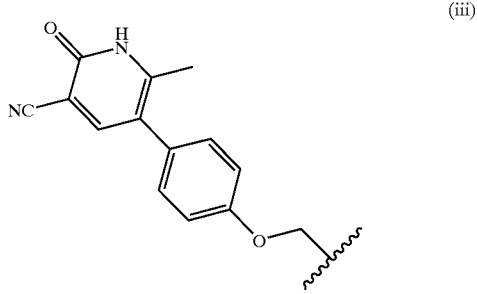

$R_p$ is:

(i)
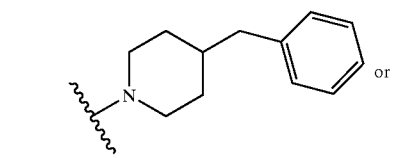

(ii)
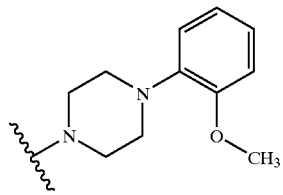

wherein $R_k$, $D_1$ and D are as defined herein, with the proviso that $D_1$ must be D if there is no other D in the compound.

Another embodiment of the present invention describes nitrosated and/or nitrosylated α-adrenergic receptor antagonists of Formula (VII):

VII
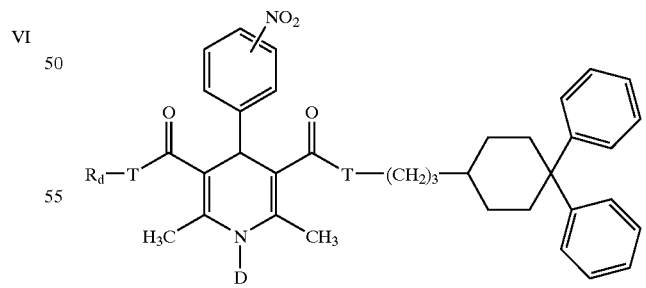

wherein $R_d$, T and D are defined as herein.

Another embodiment of the present invention describes nitrosated and/or nitrosylated α-adrenergic receptor antagonists of Formula (VIII):

VIII

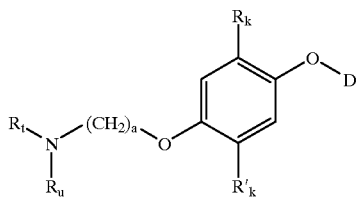

wherein $R_t$ and $R_u$ are each independently a hydrogen, a lower alkyl, a cycloalkyl, an aryl, or $R_t$ and $R_u$ when taken together with the nitrogen atom to which they are attached are a heterocyclic ring; and $R_k$, $R'_k$, and D are as defined herein.

Compounds of the present invention which have one or more asymmetric carbon atoms can exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof.

Another aspect of the present invention provides processes for making the novel compounds of the invention and to the intermediates useful in such processes. The compounds of the present invention of Formula (I), Formula (II), Formula (III), Formula (IV), Formula (V), Formula (VI), Formula (VII) and Formula (VIII) can be synthesized by one skilled in the art following the methods and examples described herein. The nitrosated and nitrosylated α-antagonists of the present invention can be synthesized as shown in reaction Schemes I through XXIV presented below, wherein $R_a$, $R_b$, $R_c$, $R_d$, $R_e$, $R_f$, $R_g$, $R_h$, $R_i$, $R'_i$, $R_j$, $R_k$, $R'_k$, $R_l$, $R_m$, $R_n$, $R_o$, $R_p$, $R_t$, $R_u$, $A_1$, $A_2$, a, n, W and X are as defined herein or as depicted in the reaction schemes for Formulas I, II, III, IV, V, VI, VII and VIII. $P^1$ is an oxygen protecting group and $P^2$ is a sulfur protecting group. The reactions are performed in solvents appropriate to the reagents and materials used are suitable for the transformations being effected. It is understood by one skilled in the art of organic synthesis that the functionality present in the compound must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known in the art for protecting thiol and alcohol groups against undesirable reactions during a synthetic procedure and many such protecting groups are known, such as those described by T. H. Greene and P. G. M. Wuts, *Protective Groups in Organic Synthesis*, John Wiley & Sons, New York (1991), the disclosure of which is incorporated by reference herein in its entirety.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Nitroso compounds of Formula (I), wherein $R_a$, $R_b$, $R_e$, $R_f$, and p are as defined herein, and an O-nitrosylated amide is representative of the D group, as defined herein, may be prepared according to Scheme I. The amine group of the quinazoline of the structure 1 is converted to the amide of the structure 2, wherein p, $R_e$ and $R_f$ are as defined herein, by reaction with an appropriate protected alcohol containing activated acylating agent, wherein $P^1$ is as defined herein. Preferred methods for the formation of amides are reacting the amine with the preformed acid chloride or symmetrical anhydride of the protected alcohol-containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of structure IA.

Scheme I

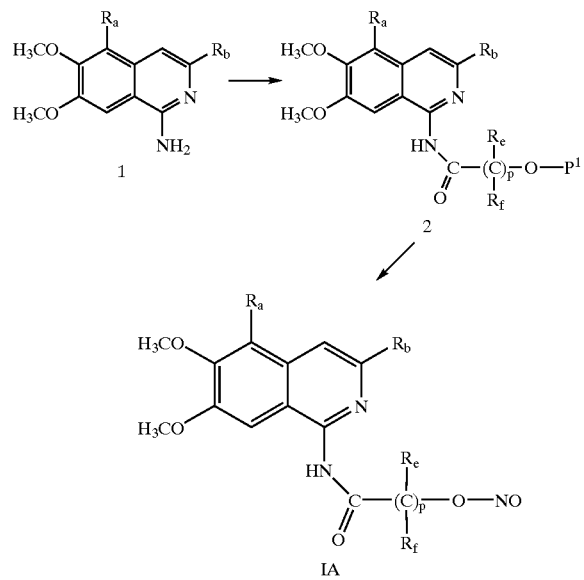

Nitroso compounds of Formula (I), wherein $R_a$, $R_b$, $R_e$, $R_f$, and p are as defined herein, and an S-nitrosylated amide is representative of the D group, as defined herein, may be prepared according to Scheme II. The amine group of the quinazoline of the structure 1 is converted to the amide of the structure 3, wherein p, $R_e$ and $R_f$ are as defined herein, by reaction with an appropriate protected thiol-containing activated acylating agent, wherein $P^2$ is as defined herein.

Preferred methods for the formation of amides are reacting the amine with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenyl-phosphine in water and sodium borohydride are preferred methods for reducing disulfide groups while an aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF, or acetonitrile with or without an amine base such as pyridine or triethylamine affords the compound of structure IB. Alternatively, treatment of compound 3 with a stoichiometric quantity of sodium nitrite in aqueous acid affords the compound of structure IB.

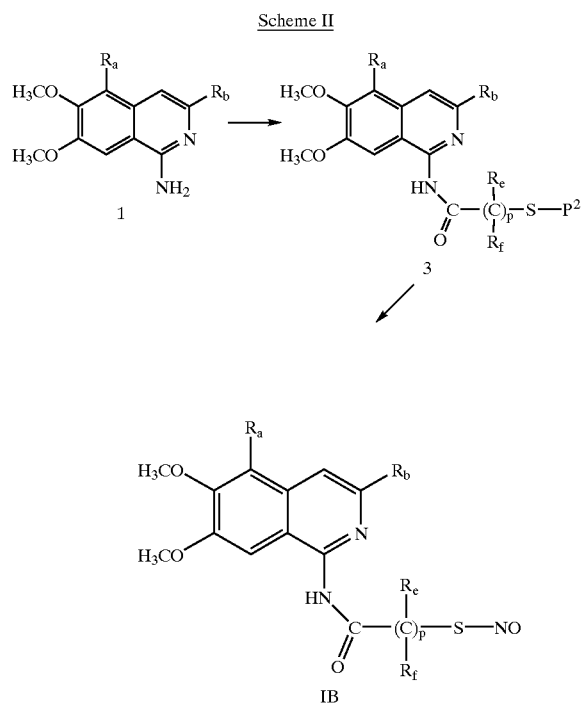

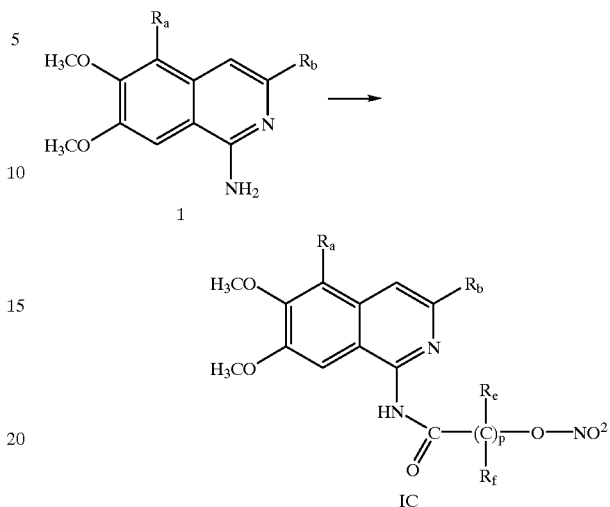

Scheme III

Nitroso compounds of Formula (II), wherein $R_e$, $R_f$, $R_g$, and p are as defined herein, and an O-nitrosylated acryl imidazoline is representative of the D group, as defined herein, may be prepared according to Scheme IV. The imidazoline group of the structure 4 is converted to the acyl imidazoline of the structure 5, wherein p, $R_e$ and $R_f$ are as defined herein, by reaction with an appropriate protected alcohol containing activated acylating agent, wherein $P^1$ is as defined herein. Preferred methods for the formation of acyl imidazolines are reacting the imidazoline with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of structure IIA.

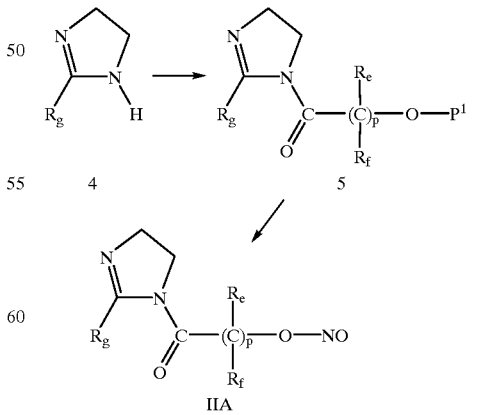

Nitro compounds of Formula (I), wherein $R_a$, $R_b$, $R_e$, $R_f$, and p are defined as Herein, and an O-nitrosated amide is representative of the D group, as defined herein, may be prepared according to Scheme III. The amine group of the quinazoline of the structure 1 is converted to the amide of the structure IC, wherein p, $R_e$ and $R_f$ are as defined herein, by reaction with an appropriate nitrate containing activated acylating agent. Preferred methods for the formation of amides are reacting the amine with the preformed acid chloride or symmetrical anhydride of the nitrate containing acid to afford the compound of structure IC.

Nitroso compounds of Formula (II), wherein $R_e$, $R_f$, $R_g$, and p are as defined herein, and an S-nitrosylated acyl imidazoline is representative of the D group, as defined herein, may be prepared according to Scheme V. The imidazoline group of the structure 4 is converted to the acyl imidazoline of the structure 6, wherein p, $R_e$ and $R_f$ are as defined herein, by reaction with an appropriate protected alcohol containing activated acylating agent, wherein $P^2$ is as defined herein. Preferred methods for the formation of acyl imidazolines are reacting the imidazoline with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydro-pyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydro-pyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF or acetonitrile with or without an amine base such as pyridine or triethylamine affords the compound of structure IIB. Alternatively, treatment of compound 6 with a stoichiometric quantity of sodium nitrite in aqueous acid affords the compound of structure IIB.

Scheme V

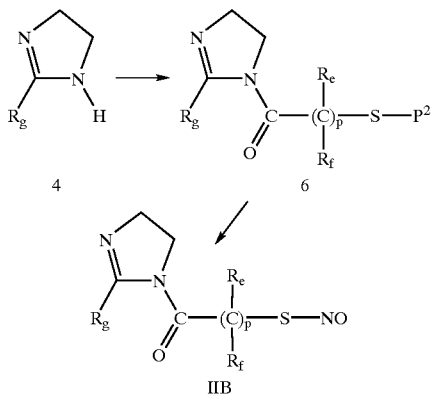

Nitro compounds of Formula (II), wherein $R_e$, $R_f$, $R_g$, and p are as defined herein, and an O-nitrosated acyl imidazoline is representative of the D group, as defined herein, may be prepared according to Scheme VI. The imidazoline group of the structure 4 is converted to the acyl imidazoline of the structure IIC, wherein p, $R_e$ and $R_f$ are as defined herein, by reaction with an appropriate nitrate containing activated acylating agent. Preferred methods for the formation of acyl imidazolines are reacting the amine with the preformed acid chloride or symmetrical anhydride of the nitrate containing acid to afford the compound of structure IC.

Scheme VI

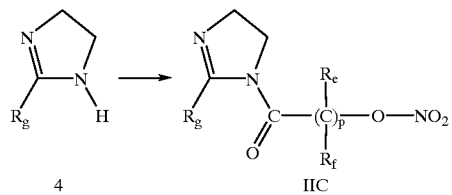

Nitroso compounds of Formula (III), wherein $R_e$, $R_f$, $R_h$, $R_j$, and p are as defined herein, and an O-nitrosylated ester is representative of the D group, as defined herein, may be prepared according to Scheme VII. The alcohol group of structure 7 is converted to the ester of structure 8, wherein p, $R_e$ and $R_f$ are as defined herein, by reaction with an appropriate protected alcohol containing activated acylating agent, wherein $P^1$ is as defined herein. Preferred methods for the formation of esters are reacting the alcohol with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of structure IIIA.

Scheme VII

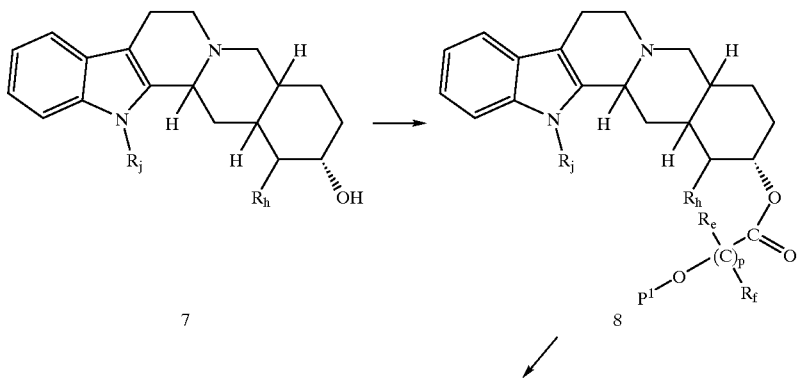

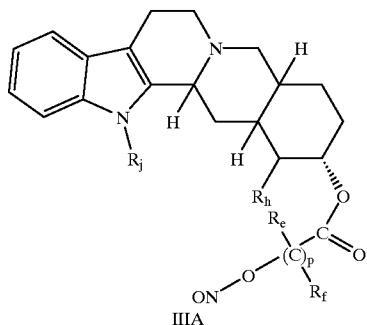

IIIA

Nitroso compounds of Formula (III), wherein $R_e$, $R_f$, $R_h$, $R_j$, and p are as defined herein, and an S-nitrosylated ester is representative of the D group, as defined herein, may be prepared according to Scheme VIII. The alcohol group of the structure 7 is converted to the ester of the structure 9, wherein p, $R_e$ and $R_f$ are as defined herein, by reaction with an appropriate protected thiol containing activated acylating agent, wherein $P^2$ is as defined herein. Preferred methods for the formation of esters are reacting the alcohol with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenyl-phosphine in water and sodium borohydride are preferred methods for reducing disulfide groups while an aqueous base is typically used to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF, or acetonitrile with or without an amine base such as pyridine or triethylamine affords the compound of structure IIIB. Alternatively, treatment of compound 9 with a stoichiometric quantity of sodium nitrite in aqueous acid affords the compound of structure IIIB.

Scheme VIII

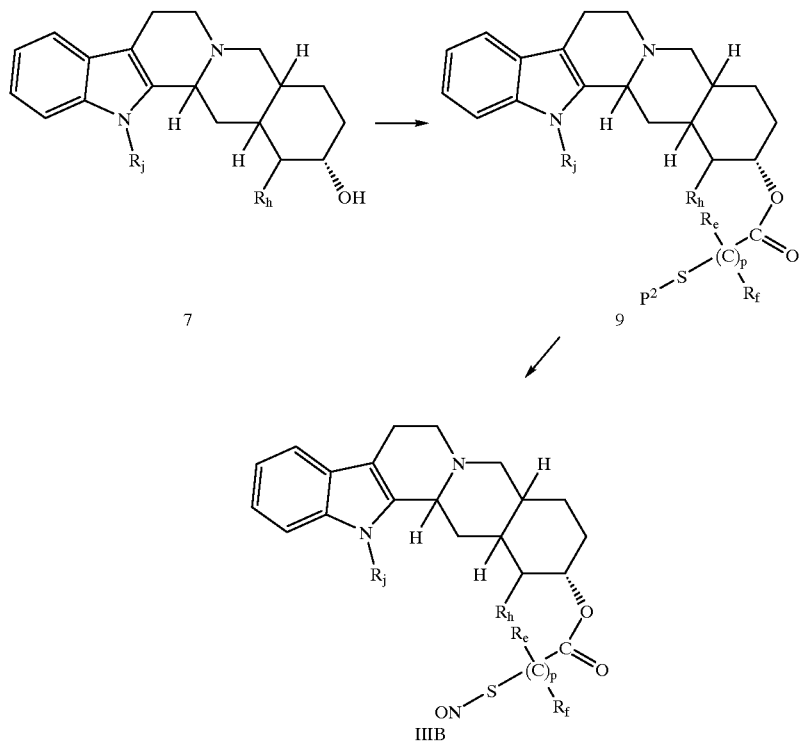

Nitro compounds of Formula (III), wherein $R_e$, $R_f$, $R_h$, $R_j$, and p are as defined herein, and an O-nitrosated ester is representative of the D group, as defined herein, may be prepared according to Scheme IX. The alcohol group of the structure 7 is converted to the ester of the structure IIIC, wherein p, $R_e$ and $R_f$ are as defined herein, by reaction with an appropriate nitrate containing activated acylating agent. Preferred methods for the formation of esters are reacting the alcohol with the preformed acid chloride or symmetrical anhydride of the nitrate containing acid to afford a compound of structure IIIC.

Scheme IX

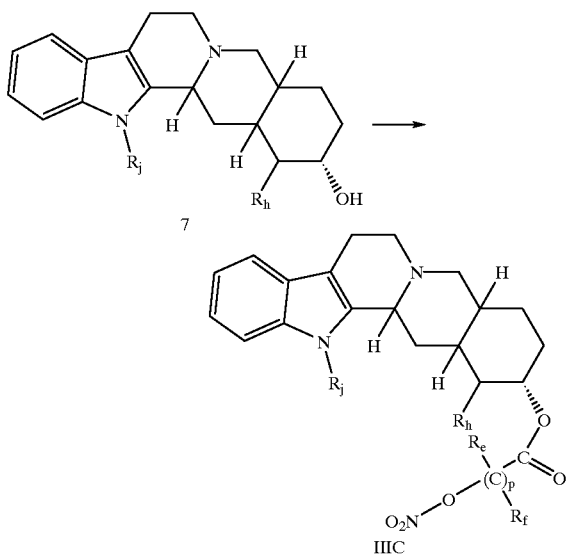

Nitroso compounds of Formula (IV), wherein $A_l$, $R_e$, $R_f$, $R_h$, $R_j$, and p are as defined herein, and an O-nitrosylated ester is representative of the X group as defined herein may be prepared according to Scheme X. An acid of the structure 10 is converted into the ester of the structure 11, wherein p, $R_e$, and $R_f$ are as defined herein, by reaction with an appropriate monoprotected diol. Preferred methods for the preparation of esters are initially forming the mixed anhydride via reaction of 10 with a chloroformate such as isobutylchloroformate in the presence of a non nucleophilic base such as triethylamine in an anhydrous inert solvent such as dichloromethane, diethylether, or THF. The mixed anhydride is then reacted with the monoprotected alcohol preferably in the presence of a condensation catalyst such as 4-dimethylamino pyridine. Alternatively, the acid 10 may be first converted to the acid chloride by treatment with oxalyl chloride in the presence of a catalytic amount of DMF. The acid chloride is then reacted with the monoprotected alcohol preferably in the presence of a condensation catalyst such as 4-dimethylamino-pyridine and a tertiary amine base such as triethyl amine to afford the ester 11. Alternatively, the acid 10 and monoprotected diol may be coupled to afford 11 by treatment with a dehydration agent such as dicyclohexyl-carbodiimide. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF, or acetonitrile affords the compound of structure IVA.

Scheme X

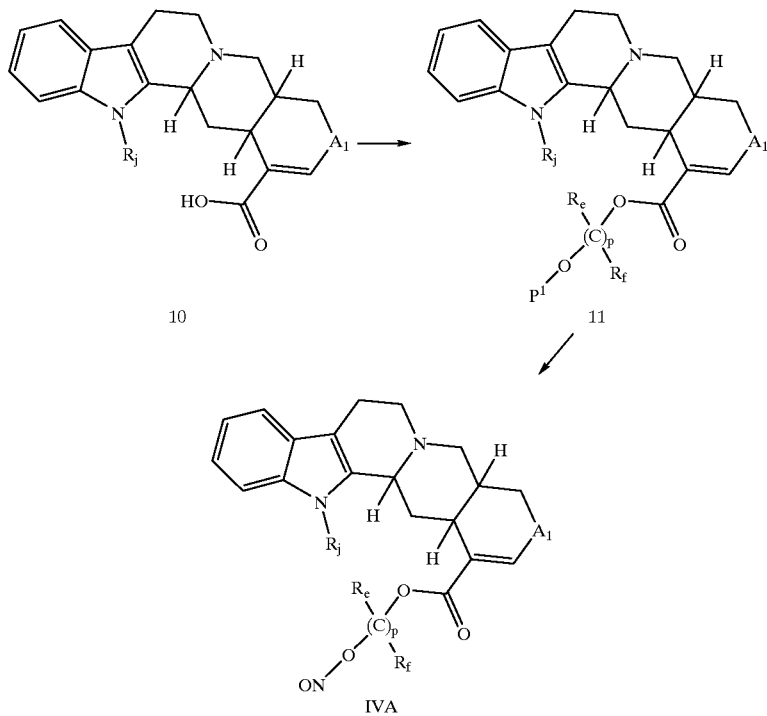

Nitroso compounds of Formula (IV), wherein $A_l$, $R_e$, $R_f$, $R_h$, $R_j$, and p are as defined herein, and an S-nitrosylated ester is representative of the X group, as defined herein, may be prepared according to Scheme XI. An acid of the structure 10 is converted into the ester of the structure 12, wherein p, $R_e$, and $R_f$ are as defined herein, and a S-nitrosylated ester is representative of the X group, as defined herein, by reaction with an appropriate protected thiol containing alcohol. Preferred methods for the preparation of esters are initially forming the mixed anhydride via reaction of 10 with a chioroformate such as isobutylchloroformate in the presence of a non nucleophilic base such as triethylamine in an anhydrous inert solvent such as diethylether or THF. The mixed anhydride is then reacted with the thiol containing alcohol preferably in the presence of a N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF or acetonitrile with or without an amine base such as pyridine or triethylamine affords the compound of structure IVB. Alternatively, treatment of compound 12 with a stoichiometric quantity of sodium nitrite in aqueous acid affords the compound of structure IVB.

Scheme XI

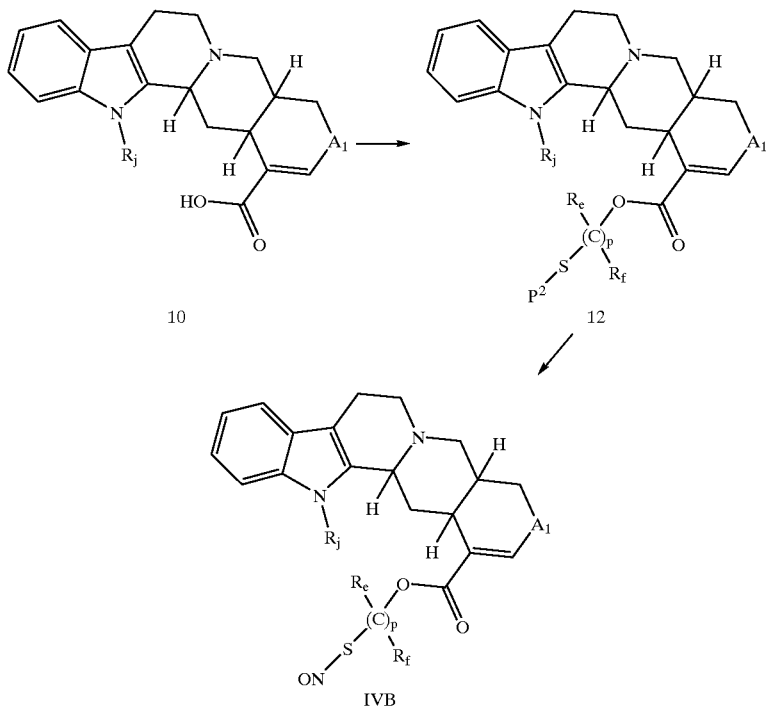

condensation catalyst such as 4-dimethyl-aminopyridine. Alternatively, the acid 10 may be first converted to the acid chloride be treatment with oxalyl chloride in the presence of a catalytic amount of DMF. The acid chloride is then reacted with the monoprotected thiol preferably in the presence of a condensation catalyst such as 4-dimethylaminopyridine and a tertiary amine base such as triethyl amine to afford the ester 12. Alternatively, the acid and thiol containing alcohol may be coupled to afford 12 by treatment with a dehydration agent such as dicyclohexylcarbodiimide. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether, or a S-triphenylmethyl thioether. Deprotection of the thiol moiety (zinc in dilute aqueous acid, triphenyl-phosphine in water and sodium borohydride are preferred methods for reducing disulfide groups while aqueous base is typically used to hydrolyze thiolesters and Nitro compounds of Formula (IV), wherein $A_l$, $R_e$, $R_f$, $R_h$, $R_j$ and p are as defined herein, and an O-nitrosated ester is representative of the X group as defined herein, may be prepared according to Scheme XII. An acid of the structure 10 is converted into the ester of the structure IVC, wherein p, $R_e$, and $R_f$ are as defined herein, by reaction with an appropriate nitrate containing alcohol. Preferred methods for the preparation of esters are initially forming the mixed anhydride via reaction of 10 with a chloroformate such as isobutylchloroformate in the presence of a non nucleophilic base such as triethylamine in an anhydrous inert solvent such as dichloromethane, diethylether, or THF. The mixed anhydride is then reacted with the nitrate containing alcohol preferably in the presence of a condensation catalyst such as 4-dimethylamino-pyridine. Alternatively, the acid 10 may be first converted to the acid chloride by treatment with oxalyl chloride in the presence of a catalytic amount of DMF. The acid chloride is then reacted with the nitrate containing alcohol preferably in the presence of a condensation catalyst such as 4-dimethylaminopyridine and a tertiary amine base such as triethyl amine to afford the a compound of structure IVC. Alternatively, the acid 10 and nitrate containing alcohol may be coupled to afford a compound of structure IVC by treatment with a dehydration agent such as dicyclohexylcarbodiimide.

Scheme XII

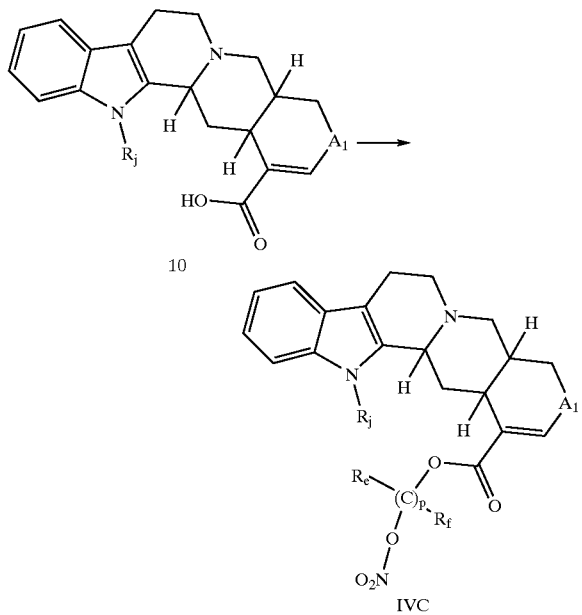

Nitroso compounds of Formula (V), wherein $R_e$, $R_f$, $R_k$, $R'_k$, $R_l$, $R_n$, and p are as defined herein, and an O-nitrosylated N-acyloxyalkyl amine is representative of the D group, as defined herein, may be prepared according to Scheme XIII. The amine group of the compound of structure 13 is converted to the N-acyloxyalkyl amine of the structure 14, wherein p, $R_e$, and $R_f$ are as defined herein, by reaction with an appropriate protected alcohol containing chloromethyl acyl derivative wherein $P^1$ is as defined herein. Preferred methods for the formation of N-acyloxyalkyl amines are reacting the amine with the preformed chloromethyl acyloxyalkyl derivative of the protected alcohol. Preferred protecting groups for the alcohol moiety are silyl ethers such as a triethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of structure VA.

Scheme XIII

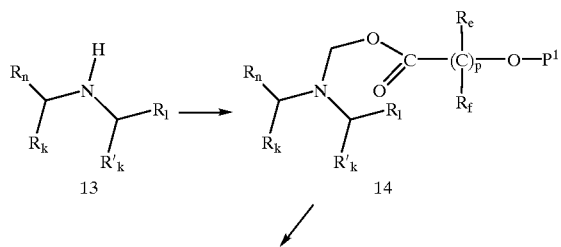

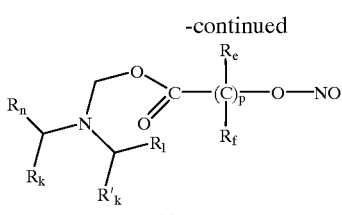

Nitroso compounds of Formula (V), wherein $R_e$, $R_f$, $R_k$, $R'_k$, $R_l$, $R_n$, and p are as defined herein, and an S-nitrosylated N-acyloxyalkyl amine is representative of the D group as defined herein may be prepared according to Scheme XIV. The amine group of the compound of structure 13 is converted to the N-acyloxyalkyl amine of the structure 15, wherein p, $R_e$ and $R_f$, are as defined herein, by reaction with an appropriate protected thiol containing chloromethyl acyl derivative wherein $P^2$ is as defined herein. Preferred protecting groups for the thiol moiety are as a thioester such as a thioacetate or thiobenzoate, as a disulfide, as a thiocarbamate such as N-methoxy-methyl thiocarbamate, or as a thioether such as a tetrahydropyranyl thioether. Deprotection of the thiol moiety (triphenylphosphine in water and sodium borohydride are preferred methods for reducing disulfide groups while an aqueous base is typically used to hydrolyze thioesters and N-methoxymethyl thiocarbamates and mercuric trifluoroacetate or silver nitrate are used to remove a tetrahydropyranyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF, or acetonitrile with or without an amine base such as pyridine or triethylamine affords the compound of structure VB.

Scheme XIV

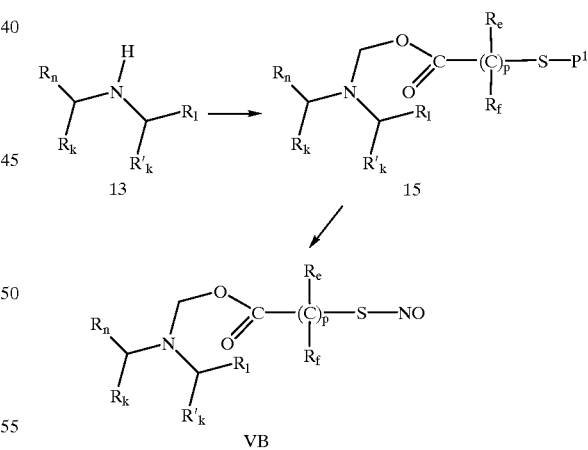

Nitro compounds of Formula (V), wherein $R_e$, $R_f$, $R_k$, $R'_k$, $R_l$, $R_n$, and p are as defined herein, and an O-nitrosated N-acyloxyalkyl amine is representative of the D group as defined herein may be prepared according to Scheme XV. The amine group of the compound of structure 13 is converted to the N-acyloxyalkyl amine of the structure VC, wherein p, $R_e$ and $R_f$ are as defined herein, by reaction with an appropriate nitrate containing chloromethyl acyl derivative. Preferred methods for the formation of N-acyloxyalkyl amines are reacting the amine with the preformed chloromethyl acyloxyalkyl derivative of the nitrate containing derivative to afford the compound of structure VC.

Scheme XV

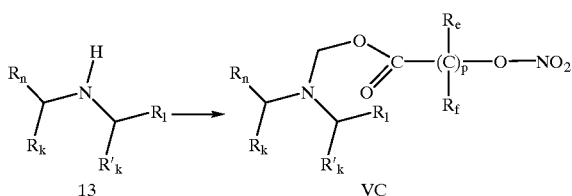

Nitroso compounds of Formula (VI), wherein $R_e$, $R_f$, $R_k$, $R_o$, $R_p$, a and p are as defined herein, and an O-nitrosylated ester is representative of the D group, as defined herein, may be prepared according to Scheme XVI. The hydroxyl group of the phenol of the structure 16 is converted to the ester of the structure 17, wherein a, p, $R_e$ and $R_f$ are as defined herein, by reaction with an appropriate protected alcohol containing activated acylating agent, wherein $P^1$ is as defined herein. Preferred methods for the formation of esters are reacting the hydroxyl with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF or acetonitrile with or without an amine base such as pyridine or triethylamine affords the compound of structure VIA.

Scheme XVI

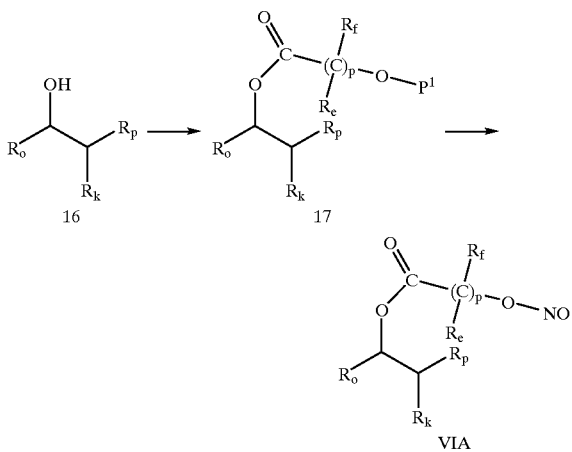

Nitroso compounds of Formula (VI), wherein $R_e$, $R_f$, $R_k$, $R_o$, $R_p$ and p are as defined herein, and an S-nitrosylated ester is representative of the D group, as defined herein may be prepared according to Scheme XVII. The hydroxyl group of the phenol of the structure 16 is converted to the ester of the structure 18, wherein a, p, $R_e$ and $R_f$ are as defined herein, by reaction with an appropriate protected thiol containing activated acylating agent, wherein $P^2$ is as defined herein. Preferred methods for the formation of esters are reacting the hydroxyl with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenyl-phosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF or acetonitrile with or without an amine base such as pyridine or triethylamine affords the compound of structure VIB. Alternatively, treatment of compound 18 with a stoichiometric quantity of sodium nitrite in aqueous acid affords the compound of structure VIB.

Scheme XVII

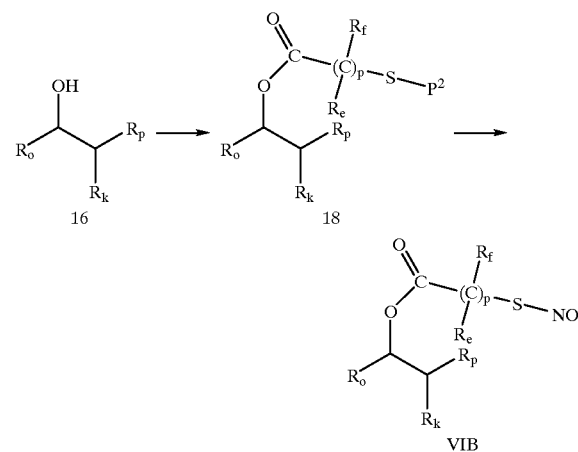

Nitro compounds of Formula (VI), wherein $R_e$, $R_f$, $R_k$, $R_o$, $R_p$, a and p are as defined herein, an O-nitrosated ester is representative of the D group, as defined herein may be prepared according to Scheme XVIII. The hydroxyl group of the phenol of the structure 16 is converted to the ester of the structure VIC, wherein a, p, $R_e$ and $R_f$ are as defined herein, by reaction with an appropriate nitrate containing activated acylating agent. Preferred methods for the formation of esters are reacting the amine with the preformed acid chloride or symmetrical anhydride of the nitrate containing acid to afford the compound of structure VIC.

Scheme XVIII

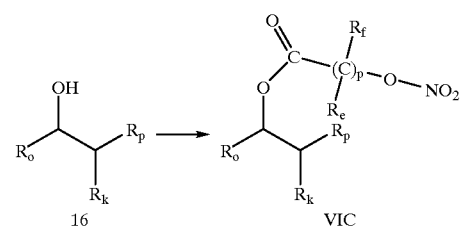

Nitroso compounds of Formula (VII), wherein $R_d$, $R_e$, $R_f$, T, and p are as defined herein, and an O-nitrosylated amide is representative of the D group, as defined herein may be prepared according to Scheme XIX. The amine group of the dihydropyridine of the structure 19 is converted to the amide of the structure 20, wherein p, $R_e$ and $R_f$ are as defined herein, by reaction with an appropriate protected alcohol containing activated acylating agent, wherein $P^1$ is as defined herein. Preferred methods for the formation of amides are reacting the amine with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of structure VIIA.

Scheme XIX

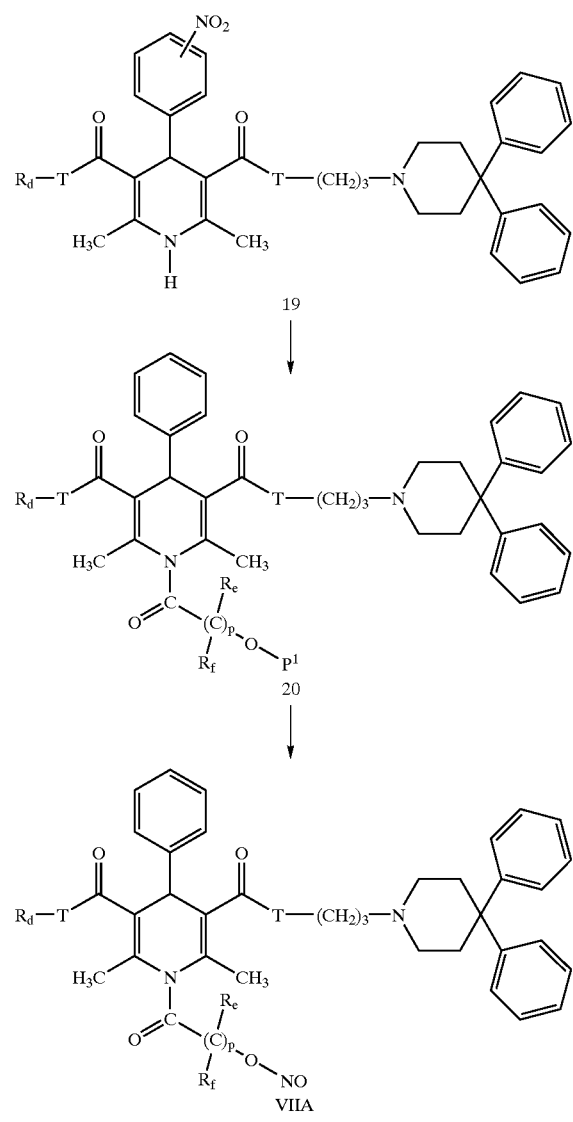

Nitroso compounds of Formula (VII) wherein $R_d$, $R_e$, $R_f$, T, and p are as defined herein, and an S-nitrosylated amide is representative of the D group, as defined herein may be prepared according to Scheme XX. The amine group of the dihydropyridine of the structure 19 is converted to the amide of the structure 21, wherein p, $R_e$, and $R_f$ are as defined herein, by reaction with an appropriate protected thiol containing activated acylating agent, wherein $P^2$ is defined above. Preferred methods for the formation of amides are reacting the amine with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF, or acetonitrile with or without an amine base such as pyridine or triethylamine affords the compound of structure VIIB. Alternatively, treatment of compound 21 with a stoichiometric quantity of sodium nitrite in aqueous acid affords the compound of structure VIIB.

Scheme XX

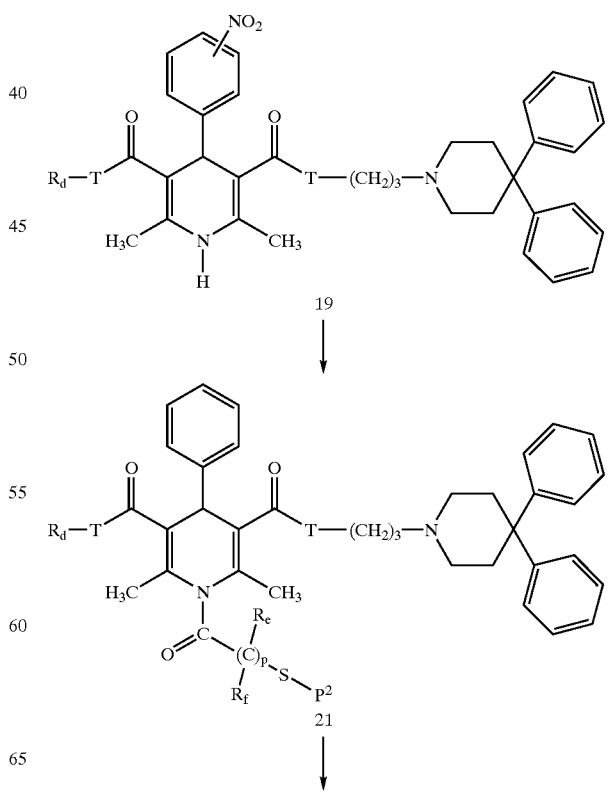

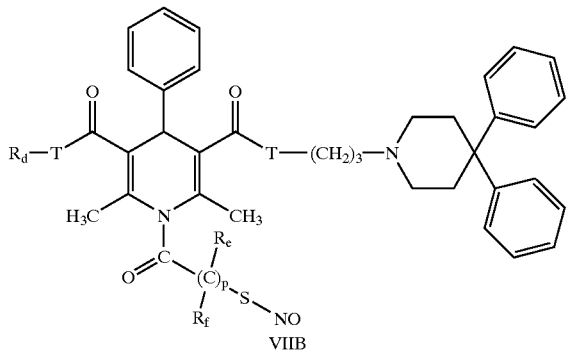

VIIB

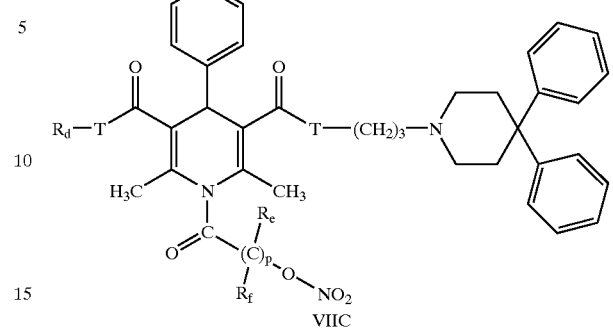

VIIC

Nitro compounds of Formula (VII), wherein $R_d$, $R_e$, $R_f$, T, and p are as defined herein, and an O-nitrosated amide is representative of the D group, as defined herein, may be prepared according to Scheme XXI. The amine group of the dihydropyridine of the structure 19 is converted to the amide of the structure VIIC, wherein p, $R_e$ and $R_f$ are as defined herein, by reaction with an appropriate nitrate containing activated acylating agent. Preferred methods for the formation of amides are reacting the amine with the preformed acid chloride or symmetrical anhydride of the nitrate containing acid to afford the compound of structure VIIC.

Nitroso compounds of Formula (VIII), wherein $R_e$, $R_f$, $R_k$, $R'_k$, $R_t$, $R_u$, a and p are as defined herein, and an O-nitrosylated ester is representative of the D group, as defined herein, may be prepared according to Scheme XXII. The hydroxyl group of the phenol of the structure 22 is converted to the ester of the structure 23, wherein a, p, $R_e$ and $R_f$ are as defined herein, by reaction with an appropriate protected alcohol containing activated acylating agent, wherein $P^1$ is as defined herein. Preferred methods for the formation of esters are reacting the hydroxyl with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF or acetonitrile with or without an amine base such as pyridine or triethylamine affords the compound of structure VIIIA.

Scheme XXI

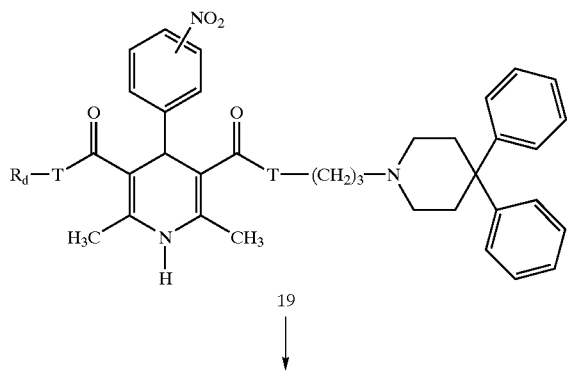

19

↓

Scheme XXII

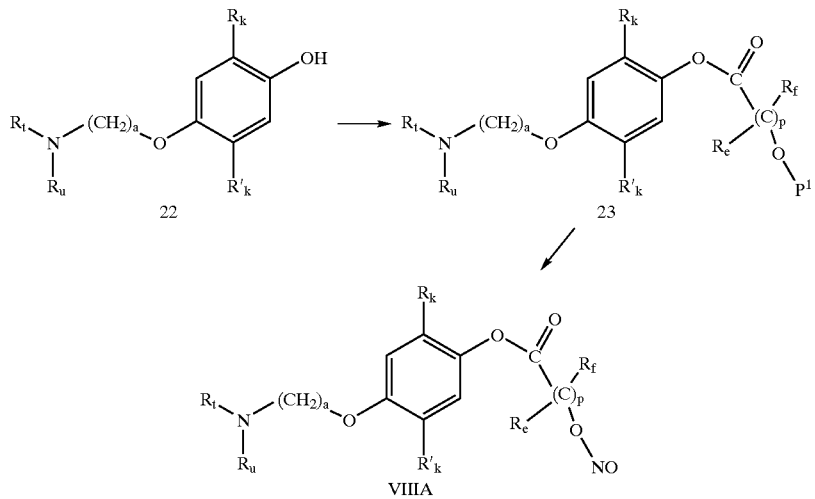

VIIIA

Nitroso compounds of Formula (VIII), wherein $R_e$, $R_f$, $R_k$, $R'_k$, $R_t$, $R_u$, a and p are as defined herein, and an S-nitrosylated ester is representative of the D group, as defined herein, may be prepared according to Scheme XXIII. The hydroxyl group of the phenol of the structure 22 is converted to the ester of the structure 24, wherein a, p, $R_e$ and $R_f$ are as defined herein, by reaction with an appropriate protected thiol containing activated acylating agent, wherein $P^2$ is as defined herein. Preferred methods for the formation of esters are reacting the hydroxyl with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenyl-phosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF or acetonitrile with or without an amine base such as pyridine or triethylamine affords the compound of structure VIIIB. Alternatively, treatment of compound 24 with a stoichiometric quantity of sodium nitrite in aqueous acid affords the compound of structure VIIIB.

Nitro compounds of Formula (VIII), wherein $R_e$, $R_f$, $R_k$, $R'_k$, $R_t$, $R_u$, a and p are as defined herein, an O-nitrosated ester is representative of the D group, as defined herein may be prepared according to Scheme XXIV. The hydroxyl group of the phenol of the structure 22 is converted to the ester of the structure VIIIC, wherein a, p, $R_e$ and $R_f$ are as defined herein, by reaction with an appropriate nitrate containing activated acylating agent. Preferred methods for the formation of esters are reacting the amine with the preformed acid chloride or symmetrical anhydride of the nitrate containing acid to afford the compound of structure VIIIC.

Scheme XXIV

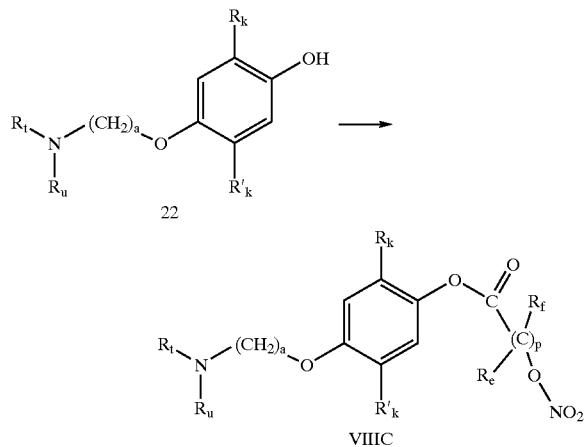

VIIIC

The compounds of the present invention include α-adrenergic receptor antagonists, including those described herein, which have been nitrosated and/or nitrosylated through one or more sites such as oxygen (hydroxyl condensation), sulfur (sulfhydryl condensation), carbon and/or nitrogen. The nitrosated and/or nitrosylated α-adrenergic receptor antagonists of the present invention donate, transfer or release a biologically active form of nitrogen monoxide (nitric oxide).

Scheme XXIII

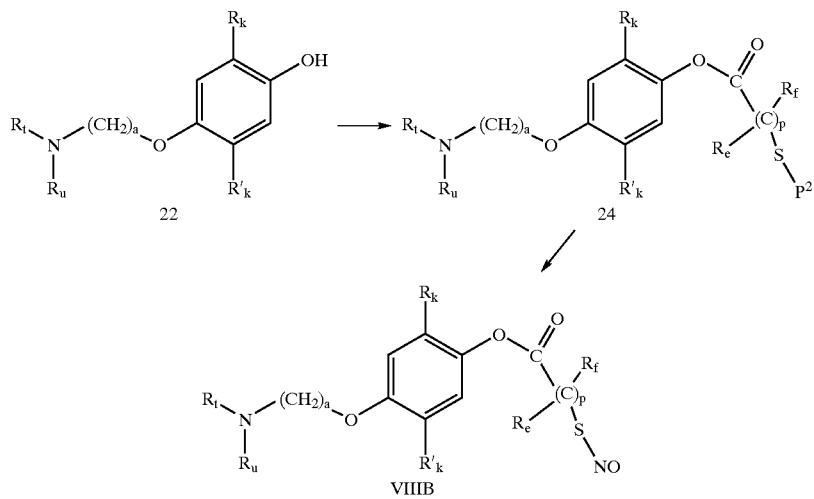

VIIIB

Nitrogen monoxide can exist in three forms: NO— (nitroxyl), NO. (nitric oxide) and NO⁺ (nitrosonium). NO— is a highly reactive short-lived species that is potentially toxic to cells. This is critical because the pharmacological efficacy of NO depends upon the form in which it is delivered. In contrast to the nitric oxide radical (NO.), nitrosonium (NO⁺) does not react with $O_2$ or $O_2^-$ species, and functionalities capable of transferring and/or releasing NO+ and NO— are also resistant to decomposition in the presence of many redox metals. Consequently, administration of charged NO equivalents (positive and/or negative) does not result in the generation of toxic by-products or the elimination of the active NO moiety.

Compounds contemplated for use in the present invention (e.g., α-adrenergic receptor antagonists and/or nitrosated and/or nitrosylated α-adrenergic receptor antagonists) are, optionally, used in combination with nitric oxide and compounds that release nitric oxide or otherwise directly or indirectly deliver or transfer nitric oxide to a site of its activity, such as on a cell membrane in vivo.

The term "nitric oxide" encompasses uncharged nitric oxide (NO.) and charged nitrogen monoxide species, preferably charged nitrogen monoxide species, such as nitrosonium ion (NO+) and nitroxyl ion (NO—). The reactive form of nitric oxide can be provided by gaseous nitric oxide. The nitric oxide releasing, delivering or transferring compounds, have the structure F—NO, wherein F is a nitric oxide releasing, delivering or transferring moiety, include any and all such compounds which provide nitric oxide to its intended site of action in a form active for its intended purpose. The term "NO adducts" encompasses any nitric oxide releasing, delivering or transferring compounds, including, for example, S-nitrosothiols, organic nitrites, organic nitrates, S-nitrothiols, sydnonimines, 2-hydroxy-2-nitrosohydrazines (NONOates), (E)-alkyl-2-[(E)-hydroxyimino]-5-nitro-3-hexene amines or amides, nitrosoamines, furoxanes as well as substrates for the endogenous enzymes which synthesize nitric oxide. The "NO adducts" can be mono-nitrosylated, poly-nitrosylated, mono-nitrosated and/or poly-nitrosated at a variety of naturally susceptible or artificially provided binding sites for nitric oxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3):165–198 (1983), the disclosures of each of which are incorporated by reference herein in their entirety.

Another embodiment of the present invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine and S-nitroso-glutathione.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS[C(R_e)(R_f)]_m SNO$;

(ii) $ONS[C(R_e)(R_f)]_m R_e$; and (iii) $H_2N-CH(CO_2H)-(CH_2)_m-C(O)NH-CH(CH_2SNO)-C(O)NH-CH_2-CO_2H$;

wherein m is an integer of from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, am alkoxy, a haloalkoxy, an amino, an alkylamino, a dialkylamino, an arylamino, a diarylamino, an alkylarylamino an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, or —T—Q; or $R_e$ and $R_f$ taken together with the carbon atoms to which they are attached are a carbonyl, a methanthial, a heterocyclic ring, a cycloalkyl group or a bridged cycloalkyl group; Q is —NO or —$NO_2$; and T is independently a covalent bond, an oxygen, $S(O)_o$, or $NR_i$, wherein o is an integer from 0 to 2, and $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, carboxamido, —$CH_2$—C(T—Q)($R_e$)($R_f$), or —($N_2O_2$—)$M^+$, wherein $M^+$ in an organic or inorganic cation; with the proviso that when $R_i$ is —$CH_2$—C(T—Q)($R_e$)($R_f$) or —($N_2 O_2$—) $M^+$; then "—T—Q" can be a hydrogen, an alkyl group, an alkoxyalkyl group, an aminoalkyl group, a hydroxy group or an aryl group.

In cases where $R_e$ and $R_f$ are a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetraflurorborate in an inert solvent.

Another group of NO adducts for use in the present invention, where the NO adduct is a compound that donates, transfers or releases nitric oxide, include compounds comprising at least one ON—O—, ON—N— or ON—C-group. The compounds that include at least one ON—O—, ON—N— or ON—C-group are preferably ON—O—, ON—N— or ON—C-polypeptides (the term "polypeptide" includes proteins and polyamino acids that do not possess an ascertained biological function, and derivatives thereof); ON—O—, ON—N— or ON—C-amino acids (including natural and synthetic amino acids and their stereoisomers and racemic mixtures); ON—O—, ON—N— or ON—C- sugars; ON—O—, ON—N— or ON—C-modified or unmodified oligonucleotides (comprising at least 5 nucleotides, preferably 5–200 nucleotides); ON—O—, ON—N— or ON—C-straight or branched, saturated or unsaturated, aliphatic or aromatic, substituted or unsubstituted hydrocarbons; and ON—O—, ON—N— or ON—C-heterocyclic compounds.

Another group of NO adducts for use in the present invention include nitrates that donate, transfer or release nitric oxide, such as compounds comprising at least one $O_2N$—O—, $O_2N$—N—, $O_2N$—S— or $O_2N$—C-group. Preferred among these are $O_2N$—O—, $O_2N$—N—, $O_2N$—S— or $O_2N$—C-polypeptides (the term "polypeptide" includes proteins and also polyamino acids that do not possess an ascertained biological function, and derivatives thereof); $O_2N$—N—, $O_2N$—N—, $O_2N$—S— or $O_2N$—C-amino acids (including natural and synthetic amino acids and their stereoisomers and racemic mixtures); $O_2N$—N—, $O_2N$—N—, $O_2N$—S— or $O_2N$—C-sugars; $O_2N$—N—, $O_2N$—N—, $O_2N$—S— or $O_2N$—C-modified and unmodified oligonucleotides (comprising at least 5 nucleotides, preferably 5–200 nucleotides); $O_2N$—O—, $O_2N$—N—, $O_2N$—S— or $O_2N$—C-straight or branched, saturated or unsaturated, aliphatic or aromatic, substituted or unsubstituted hydrocarbons; and $O_2N$—O—, $O_2N$—N—, $O_2N$—S— or $O_2N$—C-heterocyclic compounds. Preferred examples of compounds comprising at least one $O_2N$—O—, $O_2N$—N—, $O_2N$—S— or $O_2N$—C-group include isosorbide dinitrate, isosorbide mononitrate, clonitrate, erythrityltetranitrate, mannitol hexanitrate, nitroglycerin, pentaerythritoltetranitrate, pentrinitrol and propatylnitrate.

Another group of NO adducts are N-oxo-N-nitrosoamines that donate, transfer or release nitric oxide and are represented by the formula: $R^1R^2$—N(O—M$^+$)—NO, where $R^1$ and $R^2$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where M$^+$ is an organic or inorganic cation, such as, for example, an alkyl substituted ammonium cation or a Group I metal cation.

Another group of NO adducts are thionitrates that donate, transfer or release nitric oxide and are represented by the formula: $R^1$—(S)—$NO_2$, where $R^1$ is a polypeptide, an amino acid, a sugar, a modified or unmodified oligonucleotide, a straight or branched, saturated or unsaturated, aliphatic or aromatic, substituted or unsubstituted hydrocarbon, or a heterocyclic group. Preferred are those compounds where $R^1$ is a polypeptide or hydrocarbon with a pair or pairs of thiols that are sufficiently structurally proximate, i.e., vicinal, that the pair of thiols will be reduced to a disulfide. Compounds which form disulfide species release nitroxyl ion (NO—) and uncharged nitric oxide (NO.). Compounds where the thiol groups are not sufficiently close to form disulfide bridges generally provide nitric oxide as the NO— form and not as the uncharged NO. form.

The present invention is also directed to agents that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine or glutamine, inhibitors of the enzyme arginase (e.g., N-hydroxy-L-arginine and 2(S)-amino-6-boronohexanoic acid) and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature*, 327:524–526 (1987); Ignarro et al, *Proc. Natl. Acad. Sci. USA*, 84:9265–9269 (1987)).

The present invention is also based on the discovery that the administration of a therapeutically effective amount of the compounds and compositions described herein is effective for treating or preventing sexual dysfunctions or enhancing sexual responses in patients, including males and females. For example, the patient can be administered a therapeutically effective amount of at least one nitrosated and/or nitrosylated α-adrenergic receptor antagonist of the present invention. In another embodiment, the patient can be administered a therapeutically effective amount of at least one α-adrenergic receptor antagonist, optionally substituted with at least one NO and/or $NO_2$ group, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one α-adrenergic receptor antagonist, optionally substituted with at least one NO and/or $NO_2$ group, and at least one vasoactive agent, and, optionally, at least one compound that donates, transfers or releases nitric oxide, or elevates levels of endogenous EDRF or nitric oxide, or is a substrate for nitric oxide synthase. The compounds can be administered separately or in the form of a composition.

A vasoactive agent is any therapeutic agent capable of relaxing vascular smooth muscle. Suitable vasoactive agents include, but are not limited to, potassium channel activators (such as, for example, nicorandil, pinacidil, cromakalim, minoxidil, aprilkalim, loprazolam and the like); calcium blockers (such as, for example, nifedipine, veraparmil, diltiazem, gallopamil, niludipine, nimodipins, nicardipine, and the like);β-blockers (such as, for example, butixamine, dichloroisoproterenol, propanolol, alprenolol, bunolol, nadolol, oxprenolol, perbutolol, pinodolol, sotalol, timolol, metoprolol, atenolol, acebutolol, bevantolol, pafenolol, tolamodol, and the like); phosphodiesterase inhibitors (such as, for example, papaverine, zaprinast, sildenafil, and the like); adenosine, ergot alkaloids (such as, for example, ergotamine, ergotamine analogs, including, for example, acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride); vasoactive intestinal peptides (such as, for example, peptide histidine isoleucine, peptide histidine methionine, substance P, calcitonin gene-related peptide, neurokinin A, bradykinin, neurokinin B, and the like); dopamine agonists (such as, for example, apomorphine, bromocriptine, testosterone, cocaine, strychnine, and the like); opioid antagonists (such as, for example, naltrexone, and the like); prostaglandins (such as, for example, alprostadil, prostaglandin $E_2$, prostaglandin $F_2$, misoprostol, enprostil, arbaprostil, unoprostone, trimoprostil, carboprost, limaprost, gemeprost, lantanoprost, ornoprostil, beraprost, sulpostrone, rioprostil, and the like); endothelin antagonists (such as, for example, bosentan, sulfonamide endothelin antagonists, BQ-123, SQ 28608, and the like) and mixtures thereof.

Another embodiment of the present invention provides methods to prevent or treat benign prostatic hyperplasia, hypertension, congestive heart failure, variant (Printzmetal) angina, glaucoma, neurodegenerative disorders, vasospastic diseases, cognitive disorders, urge incontinence, and overactive bladder, and for reversing the state of anesthesia by administering to a patient in need thereof a therapeutically effective amount of the compounds and/or compositions described herein. For example, the patient can be administered a therapeutically effective amount of at least one nitrosated and/or nitrosylated α-adrenergic receptor antagonist of the present invention. In another embodiment, the patient can be administered a therapeutically effective amount of at least one α-adrenergic receptor antagonist, optionally substituted with at least one NO and/or $NO_2$ group, and at least one compound that donates, transfers or releases nitric oxide, or elevates levels of endogenous EDRF or nitric oxide or is a substrate for nitric oxide synthase. In yet another embodiment, the patient can be administered a therapeutically effective amount of at least one α-adrenergic receptor antagonist, optionally substituted with at least one NO and/or $NO_2$ group, and at least one vasoactive agent, and, optionally, at least one compound that donates, transfers or releases nitric oxide, or elevates levels of endogenous EDRF or nitric oxide, or is a substrate for nitric oxide synthase. The compounds and compositions of the present invention can also be administered in combination with other medications used for the treatment of these disorders.

When administered in vivo, the compounds and compositions of the present invention can be administered in combination with pharmaceutically acceptable carriers and in dosages described herein. When the compounds and compositions of the present invention are administered as a mixture of at least one nitrosated and/or nitrosylated α-adrenergic receptor antagonist or at least one α-adrenergic receptor antagonist and at least one nitric oxide donor, they can also be used in combination with one or more additional compounds which are known to be effective against the specific disease state targeted for treatment (e.g., vasoactive agents). The nitric oxide donors and/or vasoactive agents can be administered simultaneously with, subsequently to, or prior to administration of the α-adrenergic receptor antagonists, including those that are substituted with one or more NO and/or $NO_2$ groups, and/or other additional compounds.

The compounds and compositions of the present invention can be administered by any available and effective delivery system including, but not limited to, orally, bucally, parenterally, by inhalation spray, by topical application, by injection into the corpus cavernosum tissue, by transurethral drug delivery, transdermally, vaginally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques. Transdermal drug administration, which is known to one skilled in the art, involves the delivery of pharmaceutical agents via percutaneous passage of the drug into the systemic circulation of the patient. Topical administration can also involve transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the present invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Dosage forms for topical administration of the compounds and compositions of the present invention can include creams, sprays, lotions, gels, ointments, coatings for condoms and the like. Administration of the cream or gel can be accompanied by use of an applicator or by transurethral drug delivery using a syringe with or without a needle or penile or vaginal insert or device, and is within the skill of the art. Typically a lubricant and/or a local anesthetic for desensitization can also be included in the formulation or provided for use as needed. Lubricants include, for example, K-Y jelly (available from Johnson & Johnson) or a lidocaine jelly, such as Xylocaine 2% jelly (available from Astra Pharmaceutical Products). Local anesthetics include, for example, novocaine, procaine, tetracaine, benzocaine and the like.

The compounds and compositions of the present invention will typically be administered in a pharmaceutical composition containing one or more selected carriers or excipients. Examples of suitable carriers include, for example, water, silicone, waxes, petroleum jelly, polyethylene glycol, propylene glycol, liposomes, sugars, and the like. The compositions can also include one or more permeation enhancers including, for example, dimethylsulfoxide (DMSO), dimethyl formamide (DMF), N,N-dimethylacetamide (DMA), decylmethylsulfoxide (C10MSO), polyethylene glycol monolaurate (PEGML), glyceral monolaurate, lecithin, 1-substituted azacycloheptan-2-ones, particularly 1-N-dodecylcyclazacylcoheptan-2-ones (available under the trademark Azone™ from Nelson Research & Development Co., Irvine, Calif.), alcohols and the like.

Suppositories for vaginal or rectal administration of the compounds and compositions of the invention can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compounds and compositions of the present invention can be formulated as pharmaceutically acceptable neutral or acid salts, including, for example, those formed with free amino groups such as those derived from hydrochloric, hydrobromic, hydroiodide, phosphoric, sulfuric, acetic, citric, benzoic, fumaric, glutamic, lactic, malic, maleic, succinic, tartaric, p-toluenesulfonic, methanesulfonic acids, gluconic acid, and the like, and those formed with free carboxyl groups, such as those derived from sodium, potassium, ammonium, calcium, ferric hydroxides, isopropylamine, triethylamine, 2-ethylamino ethanol, histidine, procaine, and the like.

"Therapeutically effective amount" refers to the amount of the α-adrenergic receptor antagonist, nitrosated and/or nitrosylated α-adrenergic receptor antagonist, nitric oxide donor and/or vasoactive agent that is effective to achieve its intended purpose. While individual patient needs may vary, determination of optimal ranges for effective amounts of each of the compounds and compositions is within the skill of the art. Generally, the dosage required to provide an effective amount of the composition, and which can be adjusted by one of ordinary skill in the art will vary, depending on the age, health, physical condition, sex, weight, extent of the dysfunction of the recipient, frequency of treatment and the nature and scope of the dysfunction or disease.

The amount of a given α-adrenergic receptor antagonist (including nitrosated and/or nitrosylated α-adrenergic receptor antagonists) or vasoactive agent which will be effective in the prevention or treatment of a particular dysfunction or disease will depend on the nature of the dysfunction or disease, and can be determined by standard clinical techniques, including reference to Goodman and Gilman, supra; The Physician's Desk Reference, supra; Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the dysfunction or disorder, and should be decided by the physician and the patient's circumstances.

The usual doses of α-adrenergic receptor antagonists (including nitrosated and/or nitrosylated α-adrenergic receptor antagonists) are about 1 mg to about 100 mg per day, preferably about 0.5 mg to about 10 mg per day. The oral dose of α-adrenergic receptor antagonists (including nitrosated and/or nitrosylated α-adrenergic receptor antagonists) are about 1 mg to about 100 mg per day preferably about 5 mg to about 80 mg per day.

The doses of nitric oxide donors in the pharmaceutical composition can be in amounts of about 0.001 mg to about 20 g, although the actual amount administered will be dependent on the specific nitric oxide donor. For example, when L-arginine is the nitric oxide donor, the dose is about 2 g/day to about 6 g/day, preferably about 3 g/day, administered orally at least one hour prior to sexual activity or sexual intercourse. Effective doses can be extrapolated from dose-response curves derived from in vitro or animal model test systems and are in the same ranges or less than as described for the commercially available compounds in the Physician's Desk Reference, supra.

The nitrosated and/or nitrosylated α-adrenergic receptor antagonists of the invention are used at dose ranges and over a course of dose regimen and are administered in the same or substantially equivalent vehicles/carrier by the same or substantially equivalent as their non-nitrosated/nitrosylated counterparts. The nitrosated and/or nitrosylated compounds of the invention can also be used in lower doses and in less extensive regimens of treatment. The amount of active ingredient that can be combined with the carrier materials to produce a single dosage form will vary depending upon the host treated and the particular mode of administration.

The dosage regimen for treating a condition with the compounds and/or compositions of this invention is selected in accordance with a variety of factors, including the type, age, weight, sex, diet and medical condition of the patient, the severity of the dysfunction, the route of administration, pharmacological considerations such as the activity, efficacy, pharmacokinetic and toxicology profiles of the particular compound used, whether a drug delivery system is used, and whether the compound is administered as part of a drug combination. Thus, the dosage regimen actually used can vary widely and therefore may deviate from the preferred dosage regimen set forth herein.

Particularly preferred methods of administration of the contemplated α-adrenergic receptor antagonist compositions (including nitrosated and/or nitrosylated α-adrenergic receptor antagonist compositions) for the treatment of male sexual dysfunction are by oral administration, by transdermal application, by injection into the corpus cavemosum, by transurethral administration or by the use of suppositories. The preferred methods of administration for female sexual dysfunction are by oral administration, topical application, transdermal application or by the use of suppositories.

The present invention also provides pharmaceutical kits comprising one or more containers filled with one or more of the ingredients of the pharmaceutical compounds and/or compositions of the present invention, including, one or more α-adrenergic receptor antagonists, optionally substituted with one or more NO and/or $NO_2$ groups, one or more of the NO donors, and one or more vasoactive agents. Such kits can also include, for example, other compounds and/or compositions (e.g., permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

EXAMPLES

The following examples are presented for illustration only, and are not intended to limit the scope of the invention or appended claims.

Examples 1

4-(N-{(1R)-1-[N-(carboxymethyl)carbamoyl]-2-(nitrosothio)ethyl}carbamoyl)(2S)-2-aminobutanoic Acid N-(N-L-γ-glutamyl-L-cysteinyl)glycine (100 g, 0.325 mol) was dissolved in deoxygenated water (200 ml) and 2N HCl (162 ml) at room temperature and then the reaction mixture was cooled to 0° C. With rapid stirring, a solution of sodium nitrite (24.4 g, 0.35 mol) in water (40 ml) was added. Stirring with cooling of the reaction mixture was continued for approximately 1 hour after which time the pink precipitate which formed was collected by vacuum filtration. The filter cake was resuspended in chilled 40% acetone-water (600 ml) and collected by vacuum filtration. The filter cake was washed with acetone (2×200 ml) and ether (100 ml) and then dried under high vacuum at room temperature in the dark to afford the title compound as a pink powder. $^1$H NMR (D$_2$O): δ1.98 (m, 2H), 2.32 (t, 2H), 3.67 (t, 1H), 3.82 (s 2H), 3.86 (dd, 1H), 3.98 (dd, 1H), 4.53 (m,1H).

Example 2
2-Acyl-17α3-methyl-3-nitrosothiolbutoxy)yohimban-16α-carboxylic Acid Methyl Ester Hydrochloride Salt 2a. 3-Methyl-3-perhydro-2H-pyran-2-ylthiobutanoic Acid
3-Methyl-3-sulfanylbutanoic acid (4.2 g, 31 mmol), dihydropyran (2.8 ml, 31 mmol), and 200 μl of 4 N HCl/Et$_2$O were allowed to stand at room temperature overnight. The volatiles were evaporated in vacuo (2 mm Hg) yielding 6.6 g (30 mmol) of material which was used without further purification. $^1$H-NMR (CDCl$_3$): δ4.92 (d, J=8.1 Hz, 1H), 4.09 (d, J=10.5 Hz, 1H), 3.49–3.56 (mult, 1H), 2.73 (dd, J=1.2 and 13.7 Hz, 1H),2.64 (d, J=13.8 Hz, 1H), 1.84–1.89 (mult 2H), 1.55–1.69 (mult, 4H), 1.51 (s, 3H).

2b. 3-Methyl-3-perhydro-2H-pyran-2-ylthiobutanoyl 3-methyl-3-perhydro-2H-pyran-2-ylthiobutanoate
The product of Example 2a (1.1 g, 5 mmol) and triethylamine (710 μl, 5 mmol) was dissolved in ethyl acetate (50 ml) and cooled to 0° C. Triphosgene (250 mg, 0.85 mmol) was added all in one portion and the reaction was stirred at 0° C. for 15 minutes then warmed to room temperature with continued stirring for 30 minutes. The precipitate which formed was removed by filtration and the filtrate was concentrated by rotary evaporation to afford 1.0 g (5 mmol) of the title compound. $^1$H-NMR (CDCl$_3$): δ5.03–5.06 (mult, 2H), 4.04–4.08 (mult, 2H), 3.46–3.51 (mult, 2H), 2.89 (d, J=15.7 Hz, 2H), 2.77 (d, J=15.6 Hz, 2H), 1.79–1.88 (mult, 4H), 1.51–1.67 (mult, 8H), 1.54 (s, 6H).

2c. 17α(3-Methyl-3-perhydro-2H-pyran-2-ylthiobutanoxy) yohimban-16α-carboxylic Acid Methyl Ester
To a solution of yohimbine (1.6 g, 4.5 mmol) in pyridine (6 ml) was added the product of Example 2b (2.5 g, 6 mmol) and 4-dimethylaminopyridine (730 mg, 6 mmol). The reaction mixture was stirred at room temperature for 6 days. Acetonitrile (50 ml) was added to the reaction and then all of the volatile components were evaporated in vacuo. The residue was dissolved in ethyl acetate (100 ml) and washed with a 10% solution of aqueous sodium carbonate. The aqueous wash was then back extracted once with ethyl acetate. The combined organic extracts were washed with H$_2$O, brine, and then dried over anhydrous sodium sulfate. Treatment of the solution with activated charcoal followed by filtration and concentration of the filtrate in vacuo gave 2.8 g of a dark syrup.

Chromatography on silica gel eluting with 1:1 hexane/ethyl acetate containing 1% by volume triethylamine afforded 670 mg (20%) of the title compound. $^1$H-NMR (CDCl$_3$): δ7.76 (s, 1H), 7.46 (d, J=7.2 Hz, 1H), 7.29 (dd, J=1.0 and 7.0 Hz, 1H),7.12 (ddd; J=1.3, 7.1, and 7.1 Hz; 1H), 7.07 (ddd; J=1.1, 7.2, and 7.2 Hz; 1H), 5.46 (d, J=2.6 Hz, 1H), 5.07–5.11 (mult, 1H), 4.06–4.11 (mult, 1H), 3.69 (s, 3H), 3.47–3.55 (mult, 1H), 3.39 (d, J=10.4 Hz, 1H), 3.02–3.12 (mult, 2H), 2.97 (dd, J=4.5 and 12.2 Hz, 1H), 2.80 (d,J=14.3 Hz, 1H), 2.71 (mult, 1H), 2.69 (d, J=13.2 Hz, 1H), 2.61–2.65 (mult, 1H), 2.39 (dd, J=2.6 and 11.6 Hz, 1H), 2.23–2.33 (mult, 2H), 1.71–2.07 (mult, 5H), 1.58–1.69 (mult, 8H), 1.51 (s, 3H), 1.49 (s, 3H). Anal Calcd for (C$_{31}$H$_{42}$N$_2$O$_5$S.1/2 H$_2$O): C, 66.05; H, 7.69; N, 4.97; S, 5.69. Found C, 65.74; H, 7.33; N, 4.88; S, 5.57.

2d. 2-Acyl-17α(3-methyl-3-sulfanylbutanoxy)yohimban-16α-carboxylic Acid Ester
The product of Example 2c (620 mg, 1.1 mmol) was refluxed in a mixture of acetic acid (5 ml) and acetyl chloride (5 ml) for 4 hours. The solvent was evaporated in vacuo (2 mm Hg). The residue was partitioned between 5% aqueous ammonium hydroxide and ethyl acetate. The aqueous wash was extracted with ethyl acetate. The combined organic extracts were washed with brine and dried over anhydrous sodium sulfate. The solvent was evaporated in vacuo and the residue was chromatographed on silica gel eluting with 1:1 hexane/ethyl acetate containing 1% by volume triethylamine to afford 210 mg (34%) of 2-acyl-17α(3-methyl-3-thioacetyl-butoxy)yohimban-16α-carboxylic acid methyl ester. This diacetate (180 mg, 0.32 mmol) was dissolved in acetic acid (4 ml) to which was added mercuric trifluoro-acetate (190 mg, 0.45 mmol) and the reaction mixture was stirred at room temperature for 2 hours. The volatiles were evaporated in vacuo leaving a gum which was triturated with 1N HCl (6 ml) to afford a yellow powder. The powder was partitioned between ethyl acetate and 10% aqueous ammonium hydroxide. The organic phase was filtered through Celite to remove the gray solid which was present and then the filtrate was washed with brine and then dried over anhydrous sodium sulfate.

Evaporation of the volatiles in vacuo afforded a solid which was chromatographed on silica gel eluting with a gradient of with 1:1 hexane/ethyl acetate containing 1% by volume triethylamine to ethyl acetate containing 1% by volume triethylamine to yield 60 mg (37%) of the title compound as a white powder. $^1$H-NMR (CDCl$_3$): δ7.81 (d, J=7.0 Hz, 1H), 7.41 (d, J=6.8 Hz, 1H), 7.23–7.29 (mult, 2H),5.46 (s, 1H), 4.17 (d, J=9.9 Hz, 1H), 3.64 (s, 3H), 3.11–3.15 (mult, 1H), 3.00 (dd, J=3.5 and 12.4 Hz, 1H), 2.64–2.84 (mult, 10H), 2.31 (dd, J=2.6 and 11.7 Hz, 1H), 2.24 (d, J=12.7 Hz, 1H), 2.04–2.08 (mult, 2H), 1.41–1.62 (mult, 11H). $^{13}$C-NMR (CDCl$_3$): δ171.6, 170.7, 169.5, 137.3, 136.4, 129.6, 124.1, 122.9, 118.3, 117.2, 114.6, 70.0, 61.0, 59.8, 51.9, 51.8, 50.9, 47.7, 45.6, 37.8, 37.6, 36.22, 36.2, 33.2, 29.9, 27.1, 23.8, 22.3.

2e. 2-Acyl-17α(3-methyl-3-(nitrosothio)butanoxy) yohimban-16α-carboxylic Acid methyl ester hydrochloride Salt
To a slurry of the compound of Example 2d (40 mg, 0.078 mmol) in 1:1 methanol/1 N HCl (4 mL) with dimethylformamide (400 μl) was added a solution of sodium nitrite (11 mg, 0.16 mmol) in H$_2$O (200 μl). The white powder turned green as the slurry was stirred at room temperature for 25 minutes. At this juncture dimethylformamide (600 μl) and additional aqueous sodium nitrite (11 mg in 200 μl of H$_2$O) was added and stirring at room temperature was continued for an additional 15 minutes. The reaction mixture was partitioned between CHCl$_3$ and H$_2$O adding 10% aqueous ammonium hydroxide to the aqueous phase until basic to pH paper. The aqueous layer was extracted with CHCl$_3$ and the combined organic extracts were washed with brine and then dried over anhydrous sodium sulfate. The volatiles were evaporated in vacuo and the residue was dissolved in ether. The product was precipitated with ethereal HCl to afford 19 mg of the title compound as a green solid. $^1$H-NMR (CDCl$_3$): δ7.81 (dd; J=1.7 and 6.8 Hz, 1H), 7.42 (d, J=6.8 Hz, 1H), 7.23–7.29 (mult, 2H), 5.43 (d, J=2.6 Hz, 1H), 4.15 (d, J=9.8 Hz, 1H), 3.63 (s, 3H), 3.36 (d, J=15.1 Hz, 1H), 3.30 (d, J=15.1 Hz, 1H), 3.12 (dd, J=4.9 and 11.0 Hz, 1H), 3.00 (dd, J=3.7 and 12.3 Hz, 1H), 2.72 (s, 3H), 2.63–2.82 (mult, 3H), 2.31 (dd, J=2.6 and 11.7 Hz, 1), 2.03 (s, 3H), 2.00 (s, 3H), 1.0–2.0 (mult, 9H).

Example 3
4-(2-{[(1-Oxo-2,2,3,4-trihydronaphthyl)methyl]amino}ethyl)phenyl 3-methyl-3-(nitrosothio)butanoate Hydrochloride 3a. (Tert-butoxy)-N-[2-(4-hydroxyphenyl)ethyl]-N-[(1-oxo (2-2,3,4 trihydro naphthyl))methyl]carboxamide 2-({[2-(4-Hydroxyphenyl)ethyl]amino}methyl)-2,3,4-trihydronaphthalen-1-one (3.39 g, 11.5 mmol) was dissolved in dichloromethane (50 mL) and di-tert-butyldicarbonate (2.50 g, 11.5 mmol) was added. The reaction mixture was stirred for 100 minutes at room temperature. The solvent was evaporated, and the residue was purified by flash chromatography on silica-gel, eluting with hexane/ethyl acetate (3:1) to give 2.32 g (51%) of the title compound. $^1$H NMR (CDCl$_3$, 300 MHz): δ1.44 (s, 9H), 1.61–1.89 (m, 1H), 2.15–2.29 (m, 1H), 2.50–2.85 (m, 4H), 2.90–3.08 (m, 2H), 3.29–3.45 (m, 3H), 3.49–3.64 (m, 1H), 6.76 (d, 2H), 7.04 (d, 2H), 7.19–7.32 (m, 2H), 7.39–7.50 (m, 1H), 8.01 (d, 1H).

3b. 4-(2-{(Tert-butoxy)-N-[(1-oxo(2-2,3,4-trihydronaphthyl))methyl]carbonylamino}ethyl)phenyl 3-methyl-3-perhydro--2H-pyran-2-ylthiobutanoate The product of Example 3a (0.300 g, 0.76 mmol) was dissolved in pyridine (0.5 mL) and a solution of the product of Example 2b (0.397 g, 0.95 mmol) in pyridine (0.5 mL) was added. The resulting solution was stirred for 18 hours at room temperature. The solvent was evaporated, and the residue was purified by flash chromatography on silica-gel, eluting with hexane/ethyl acetate (4:1) to give 0.332 g (73%) of the title compound. $^1$H-NMR (CDCl$_3$, 300 MHz): δ1.44 (s, 9H), 1.56 (d, 6H), 1.52–1.78 (m, 6H), 1.66–1.97 (m, 1H), 2.16–2.31 (m, 1H), 2.73–3.06 (dd, overlapping with multiplet, 7H), 3.33–3.67 (m, 5H), 4.05–4.17 (m, 1H), 5.09–5.17 (m, 1H), 7.01 (d, 2H), 7.13–7.36 (m, 4H), 7.47 (t, 1H), 8.01 (d, 1H).

3c. 4-(2-{(Tert-butoxy)-N-[(1-oxo(2-2,3,4-trihydronaphthyl))methyl]carbonylamino}ethyl)phenyl 3-methyl-3-sulfanylbutanoate The product of Example 3b (0.192 g, 0.32 mmol) was dissolved in methanol (2 mL) and a solution of silver nitrate (0.117 g, 0.69 mmol) in water (0.4 mL) was added. The resulting mixture was stirred for 1 hour at room temperature. The solvent was evaporated, the residue was suspended in acetone/water (1:10) and 1N HCl (1 mL) was added. After stirring for 18 hours at room temperature, the precipitate was filtered and filtrate was extracted with dichloromethane. The organic layer was washed with brine, dried over anhydrous sodium sulfate and concentrated in vacuo to give 0.085 g (51%) of the title compound. $^1$H NMR (CDCl$_3$, 300 MHz): δ1.44 (s, 9H), 1.58 (d, 6H), 1.73–1.96 (m, 1H), 2.17–2.31 (m, 1H), 2.38 (s, 1H), 2.64–2.93 (m, 5H), 2.94–3.07 (m, 2H),3.45 (t,3H, 3.58–3.67 (m, 1H), 7.02 (d, 2H), 7.15–7.36 (m, 4H), 7.47 (t, 1H), 8.01 (d, 1H).

3d. 4-(2-{[(1-Oxo-2-2,3,4-trihydronaphthyl)methyl]amino}ethyl)phenyl 3-methyl-3-sulfanylbutanoate The product of Example 3c (0.149 g, 0.29 mmol) was dissolved in dichloromethane (3 mL) and trifluoroacetic acid (3 mL) was added. The resulting solution was stirred for 15 minutes at room temperature. The solvent was evaporated and the residue was dissolved in dichloromethane (10 mL). Water (5 mL) was added and pH was made basic with saturated sodium bicarbonate solution. Organic layer was separated and aqueous fraction was extracted with dichloromethane. The combined organic phase was washed with brine, dried over anhydrous sodium sulfate and concentrated in vacuo to give 0.098 g (82%) of the title compound. $^1$H NMR (CDCl$_3$, 300 MHz): δ159 (s, 6H), 1.84–2.03 (m, 1H), 2.15–2.26 (m, 1H), 2.39 (s, 1H), 2.82–3.16 (m, 11H), 7.06 (d, 2H), 7.18–7.35 (m, 4H), 7.49 (t, 1H), 8.00 (1H).

3e. 4-(2-{[(1-Oxo-2-2,3,4-trihydronaphthyl)methyl]amino}ethyl)phenyl 3-methyl-3-(nitrosothio)butanoate Hydrochloride The product of Example 3d (0.081 g, 0.20 mmol) was dissolved in methanol (4 mL) and 1N HCl was added. A solution of sodium nitrite (0.045 g, 0.65 mmol) in water (0.25 mL) was added. After stirring for 15 minutes at room temperature an additional sodium nitrite (0.045 g, 0.65 mmol) in water (0.25 mL) was added. The reaction mixture was stirred for 15 more minutes, and was then extracted with dichloromethane. The organic layer was dried over anhydrous sodium sulfate and the solvent was evaporated to give 0.072 g (81%) of the title compound as a green solid. $^1$H NMR (CDCl$_3$, 300 MHz):δ1.72–1.93 (m, 1H), 2.09 (s, 6H), 2.18–2.30 (m, 1H), 2.84–3.11 (m, 1H), 3.14–3.33 (m, 6H), 3.36–3.57 (m, 4H), 7.03 (d, 2H), 7.18–7.42 (m, 4H), 5.53 (t, 1H), 7.94 (d, 1H).

Examples 4
2-[4-(2-Methoxyphenyl)piperaziny]-1-(naphthyloxymethyl) ethyl 3-methyl-3-(nitrosothio) butanoate Hdrochloride 4a. 3-Methyl-3-(2,4,6-trimethoxyphenylthio)butanoic Acid To a solution of 3-methyl-3-sulfanylbutanoic acid (Sweetman et al, *J. Med Chem.*,14:868 (1971), the disclosure of which is incorporated herein by reference in its entirety) (4.6 g, 34 mmol) in methylene chloride (250 mL) under nitrogen and cooled over ice/salt to 5° C. (internal temperature) was added trifluoroacetic acid (82 g, 0.72 mol). No significant temperature rise was noted during the addition. To this was then added dropwise a solution of 2,4,6-trimethoxybenzyl alcohol (Munson et al.,*J. Org. Chem.*, 57, 3013 (1992), the disclosure of which is incorporated herein by reference in its entirety) (6.45 g, 32 mmol) in methylene chloride (150 mL) such that the reaction temperature does not rise above 5° C. After the addition was complete, the mixture was stirred for an additional 5 minutes at 5° C. and the volatiles were evaporated in vacuo (toluene or ethyl acetate can be used to assist in the removal of volatile material). The residue was partitioned between diethyl ether and water and the organic phase dried over anhydrous sodium sulfate, filtered and the volatile material evaporated in vacuo. The residue was treated with activated charcoal and recrystalized from diethyl ether/hexane. The product was isolated as a white solid in 70% yield (7 g). mp 103–105° C.; $^1$H NMR(CDCl$_3$): δ6.12 (s, 2H), 3.80–3.85 (m, 11H), 2.74 (s, 2H), 1.47 (s, 6H). $^{13}$C NMR (CDCl$_3$): δ173.9, 160.6, 158.6, 105.6, 90.5, 55.7, 55.3, 45.9, 43.6, 28.4, 21.0.

4b. 2-[4-(2-Methoxyphenyl)piperazinyl]-1-(naphthyloxymethyl)ethyl 3-methyl-3-(2,4,6-trimethoxyphenylthio)butanoate Under a nitrogen atmosphere, 3-[4-(2-methoxyphenyl)piperazinyl]-1-naphthyloxypropan-2-ol (0.130 g, 0.35 mmol) was dissolved in anhydrous dimethylformamide (2 mL) and 4-dimethylaminopyridine (0.017 g, 0.14 mmol) was added, followed by the product of Example 4a (0.211 g, 0.69 mmol) and 1-ethyl-3-(3-dimethylaminopropyl) carbodimide (0.132 g, 0.69 mmol). The resulting mixture was stirred 2 hours at room temperature and then 24 hours at 50° C. The solvent was evaporated in vacuo and the residue was purified by flash chromatography on silica gel eluting with hexane/ethyl acetate (3:1) to (2:1) to give the title compound (0. 133 g, 56% yield). $^1$H NMR (CDCl$_3$, 300 MHz): δ1.49–1.53 (d, 6H, J=2.42 Hz). 2.70–2.84 (m, 8H), 2.98–3.09 (m, 4H), 3.75–3.85 (m, 11H), 3.86 (s, 3H), 4.31–4.36 (m, 2H), 5.43–5.52 m, 1H), 6.08 (s, 2H), 6.81–6 86 (m, 2H), 6.90–6.93 (m. 2H), 6.97–7.01 (m, 1H), 7.33–7.7 (m, 4H), 7.77–7.82 (m, 1H), 8.23–8.27 (m, 1H).

4c. 2-[4-(2-Methoxyphenyl)piperazinyl]-1-(naphthyloxymethyl)ethyl 3-methyl-3-sulfanylbutanoate The product of Example 4b (0.128 g, 0.186 mmol) was dissolved in methylene chloride (0.50 mL), and then anisole (0.13 mL, 1.20 mmol), phenol (0.013 g, 0.14 mmol), water (0.13 mL), and trifluoroacetic acid (0.80 mL, 10.4 mmol) were added. After 1 hour of stirring at room temperature, toluene (2 mL) was added and volatiles were evaporated. The residue was purified by flash chromatography on silica gel eluting with hexane/ethyl acetate (2:1) to give the title compound (0.055 g, 60% yield) as a solid. $^1$H NMR (CDCl$_3$, 300 MHz): δ1.49–1.53 (d, 6H, J=2.42 Hz), 2.59 (s, 1H), 2.69–2.86 (m, 8H), 3.01–3.09 (m, 4H), 3.86 (s, 3H), 4.26–4.39 (m, 2H), 5.53–5.63 (m, 1H), 6.81–6.88 (d, 2H, J=7.5 Hz), 6.90–6 95 (m, 2H), 6.98–7.04 (m, 1H), 7.34–7.40 (t, 1H, J=7.5 Hz), 7.43–7.78 (m, 3H), 7.79–7.82 (m, 1H), 8.23–8.26 (m, 1H).

4d. 2-[4-(2-Methoxyphenyl)piperazinyl]-1-(naphthyloxymethyl)ethyl 3-methyl-3-(nitrosothio)butanoate Hydrochloride The product of Example 4c (0.048 g, 0.097 mmol) was dissolved in methanol (5 mL) and 1N solution of hydrochloric acid (1.5 mL) was added. The resulting mixture was cooled to 0° C. and a solution of sodium nitrite (0.040 g, 0.058 mmol) in water (0.5 mL) was added. After 1 hour stirring at 0° C. the reaction mixture was extracted with methylene chloride, washed with brine and dried over anhydrous sodium sulfate. The solvent was evaporated in vacuo to give the title compound (0.045 g, 82% yield) as a green solid. $^1$H NMR(CDCl$_3$, 300 MHz): δ2.00 (s, 6H), 3.38–3.50 (m, 13H), 3.88 (s, 3H), 4.31–4.40 (m, 2H), 5.91 (s, 1H), 6.79–6.95 (m, 5H), 7.33–7.70 (m, 4H), 7.79–7.82 (m, 1H), 8.09–8.12 (m, 1H).

Example 5

N-{2-[4-(2-furylcarbonyl)piperazinyl]-6,7-dimethoxyguinazolin-4-yl}-3-methyl-3(nitrosothio)butanamide 5a. N-{2-[4-(2-furylcarbonyl)piperazinyl]-6,7-dimethoxyquinazolin-4-yl}-3-methyl-3-(2,4,6-trimethoxyphenylthio)butanamide Under a nitrogen atmosphere 4-(4-amino-6,7-dimethoxyquinazolin-2-yl)piperazinyl 2-furyl ketone (0.200 g, 0.52 mmol) was dissolved in anhydrous dimethylformamide (5 mL) and 4-dimethylaminopyridine (0.025 g, 0.21 mmol) was added, followed by the product of Example 4a (0.319 g, 1.04 mmol) and 1-ethyl-3-(3-dimethylaminopropyl)carbodiimide (0.199 g, 1.04 mmol). The resulting mixture was stirred at 50° C. for 48 hours. The solvent was evaporated in vacuo and the residue was purified by flash chromatography on silica gel eluting with hexane/ethyl acetate (3:1) to (1:5) to give 0.072 g (20% yield) of the title compound as a white solid. $^1$H NMR (CDCl$_3$, 300 MHz): δ1.52 (s, 6H), 2.88 (s, 1H), 2.90 (s, 2H), 2.96 (s, 1), 3.56 (s, 6H), 3.72 (2, 3H), 3.90–4.01 (m, 16H), 6.48–6.52 (dd, 1H, J=1.69 and 3.32 Hz), 6.94 (s, 1H), 7.01–7.05 (d, 1H, J=3.45 Hz), 7.19 (s, 1H), 7.50–7.53 (m, 1H).

5b. N-{2-[4-(2-furylcarbonyl)piperazinyl]-6,7-dimethoxyquinazolin-4-yl}-3-methyl-3-sulfanylbutanamide The product of Example 5a (0.160 g, 0.24 mmol) was dissolved in methylene chloride (0.67 mL), and then anisole (0.16 mL, 1.47 mmol), phenol (0.007 g, 0.047 nmol), water (0.16 mL), and trifluoroacetic acid (0.67 mL, 8.63 mmol) were added. After 45 minutes of stirring at room temperature, toluene (5 mL) was added and volatiles were evaporated. The residue was purified by flash chromatography on silica gel eluting with methylene chloride/methanol (30:1) to (15:1) to give the title compound (0.043 g, 36% yield) as a solid. $^1$HNMR (CDCl$_3$, 300 MHz): δ1.58 (s, 6H), 2.45 (s, 1H), 3.00 (s, 2H), 3.87–3.94 (d, 6H, J=6.28 Hz), 3.92–4.06 (m, 8H), 6.53–6.57 (dd, 1H, J=6.98 (s, 1H), 7.15–7.18 (d, 1H, J=3.48 Hz), 7.49 (s, 1H), 7.54–7.59 (m, 1H).

5c. N-{2-[4-(2-furylcarbonyl)piperazinyl]-6,7-dimethoxyquinazolin-4-yl}-3-methyl-3-(nitrosothio)butanamide The product of Example 5b (0.036 g, 0.080 mmol) was dissolved in methanol and 1N solution of hydrochloric acid (1 mL) was added. The resulting mixture was cooled to 0° C. and a solution of sodium nitrite (0.067 g, 0.97 mmol) in water (0.5 mL) was added. After 40 minutes stirring at 0° C. the reaction mixture was extracted with methylene chloride, washed with brine and dried over anhydrous sodium sulfate. The solvent was evaporated in vacuo to give the title compound (0.023 g, 55% yield) as a green solid. $^1$H NMR (CDCl$_3$, 300 MHz): δ2.12 (s, 6H), 3.49 (s, 2H), 3.85–3.99 (m, 14H), 6.51–6.55 (dd, 1H, J=1.74 and 3.45 Hz), 6.79–6.98 (m, 2H), 7.06–7.09 (d, 1H, J=3.23 Hz), 7.34–7.58 (m, 1H).

Example 6

4-[2-(Dimethylamino)ethoxy]-2-methyl-5-(methylethyl)phenyl 3-methyl-3-(nitrosothio)butanoate Hydrochloride 6a. 4-[2-(Dimethylamino)ethoxy]-2-methyl-5-(methylethyl)phenol 4-[2-(Dimethylamino)ethoxy]-2-methyl-5-(methylethyl)phenyl acetate (1.00 g, 3.20 mmol) was dissolved in methanol (10 mL) and sodium hydroxide (0.317 g, 7.92 mmol) was added. The reaction mixture was stirred at room temperature for 10 minutes, diluted with ethyl ether (10 mL) and washed with sodium bicarbonate solution. The organic layer was dried over anhydrous sodium sulfate, filtered and concentrated in vacuo to give the title compound (0.71 g, 93% yield) as a white solid. $^1$H NMR (CDCl$_3$, 300 MHz): δ1.10–1.13 (d, 6H, J=6.9 Hz), 2.19 (s, 3H), 2.41 (s, 6H), 2.80–2.85 (t, 2H, J=3.9 Hz), 3.19–3.26 (m, 1H), 4.02–4.07 (t, 2H, J=5. Hz), 6.37–6.59 (d, 2H, J=3.72 Hz).

6b. 4-[2-(Dimethylamino)ethoxy]-2-methyl-5-(methylethyl)phenyl 3-methyl-3(2,4,6-trimethoxyphenylthio)butanoate Under a nitrogen atmosphere, the product of Example 6a (0.270 g, 1.14 mmol) was dissolved in anhydrous dimethylformamide (2 mL) and 4-dimethylamino-pyridine (0.028 g, 0.23 mmol) was added, followed by the product of Example 4a (0.418 g, 1.36 mmol) and 1-ethyl-3-(3-dimethylaminopropyl)carbodiimide (0.260 g, 1.36 mmol). The resulting mixture was stirred at 55° C. for 24 hours. The solvent was evaporated in vacuo and the residue was purified by flash chromatography on silica gel, eluting with methylene chloride/methanol (20:1) to give 0.232 g (39% yield) of the title compound. $^1$H NMR (CDCl$_3$, 300MHz): δ1.14–1.18 (d, 6H, J=6.9 Hz), 1.59 (s, 6H), 2.15 (s, 3H), 2.35 (s, 6H), 2.72–2.77 (t, 2H, J=5.9 Hz), 2.93–2.96 (m, 2H), 3.23–3.28 (m, 11H), 4.03–4.07 (t, 2H, J=5.9 Hz), 6.11 (s, 2H), 6.67 (s, 1H), 6.81 (s, 1H).

6c. 4-[2-(Dimethylamino)ethoxy]-2-methyl-5-(methylethyl)phenyl 3-methyl-3-sulfanylbutanoate The product of Example 6b (0.220 g, 0.42 mmol) was dissolved in methylene chloride (0.3mL) and anisole (0.22 mL, 2.02 mmol), phenol (0.022 g, 0.23 mmol), water (0.22 mL) and trifluoroacetic acid (1.0 mL, 13.0 mmol) were added. After 1 hour of stirring at room temperature, toluene (5 mL) was added and volatiles were evaporated. The residue was purified by flash chromatography on silica gel, eluting with methylene chloride/methanol (20:1) to give the title compound (0.095 g, 64% yield). $^1$H NMR (CDCl$_3$, 300 MHz): δ1.14–1.16 (d, 6H, J=6.9 Hz), 1.58 (s, 6H), 2.14 (s, 3H), 240 (s, 1H), 2.87–2.94 (m, 8H), 3.14–3.20 (m, 1H), 3.50–3.53 (m, 2H), 4.31–4.34 (m, 2H), 6.67 (s, 1H), 6.84 (s, 1H).

6d. 4-[2-(Dimethylamino)ethoxy]-2-methyl-5-(methylethyl) phenyl 3-methyl-3-(nitrosothio)butanoate Hydrochloride The product of Example 6c (0.035 g, 0.10 mmol) was dissolved in methanol (5 mL) and 1N solution of hydrochloric acid (1 mL) was added. The resulting mixture was cooled to 0° C. and a solution of sodium nitrite (0.014 g. 0.20 mmol) in water (0.7 mL) was added. After 20 minutes stirring at 0° C., an additional sodium nitrite (0.032 g, 0.46 mmol) in water (0.7 mL) was added and the resulting mixture was stirred for 30 minutes. The reaction mixture was extracted with methylene chloride, washed with brine and dried over anhydrous sodium sulfate. The solvent was evaporated in vacuo to afford the product (0.028 g, 67% yield) as a green solid. $^1$H NMR (CDCl$_3$, 300 MHz): δ1.13–1.17 (d, 6H, J=6.9 Hz), 2.08–2.11 (m, 9H), 2.95 (s, 6H), 3.13–3.20 (m, 1H), 3.45–3.51 (m, 4H), 4.43–4.46 (m, 2H), 6.23 (s, 1H), 6.70 (s, 1H), 6.76 (s, 1H).

Example 7

3-Methyl-3-(nitrosothio)butyl(3-{[(1-{[3-methyl-3-(nitrosothio)butyl]oxycarbonyl}(2-imidazolin-2-yl)) methyl](methylphenyl)amino}phenoxy)formate 7a. 3-Methyl-3-sulfanylbutyl Acetate 3-Methyl-3-sulfanylbutan-1-ol (Sweetman et al, *J. Med. Chem.* 14:868 (1971), the disclosure of which is incorporated by reference herein in its entirety) (5 g, 42 mmol) and pyridine (3.6 mL, 43 mmol) were dissolved in methylene chloride (50 mL) and cooled to –78° C. Acetyl chloride (3.1 mL, 43 mmol) was added dropwise. The solution was kept cold for 30 min then allowed to warm to room temperature. Stirring was continued for 1.5 hours. The reaction mixture was diluted with methylene chloride, washed with 1 N HCl and brine, and dried over sodium sulfate. Evaporation of the solvent gave 6.6 g of the title compound which was used without further purification. $^1$H-NMR (CDCl$_3$): δ1.41 (s, 3H), 1.92 (t, J=7.2 Hz, 2H), 2.03 (s, 3H), 2.21 (s, 1H), 4.25 (t, J=7.1 Hz, 2H).

7b. 3-Methyl-3-perhydro-2H-pyran-2-ylthiobutyl Acetate

The product of Example 7a (6.6 g, 41 mmol), dihydropyran (4 mL, 44 mmol), and 4 N HCl/Et$_2$O (1 mL) were allowed to stand at room temperature for 24 hours. The volatiles were evaporated in vacuo to leave the title compound as a viscous oil which was used without further purification. $^1$H-NMR (CDCl$_3$): δ1.36 (s, 3H), 1.37 (s, 3H), 1.42–1.88 (mult, 6H), 1.93 (t, J=7.5 Hz, 2H), 2.03 (s, 3H), 3.46–3.52 (mult, 1H), 4.04–4.09 (mult, 1H), 4.24 (t, J=7.1 Hz, 2H), 4.97 (dd, J=3.4 and 6.6 Hz, 1H).

7c. 3-Methyl-3-perhydro-2H-pyran-2-ylthiobutan-1-ol

The product of Example 7b (800 mg, 3.3 mmol) and sodium bicarbonate (1.4 g, 16 mmol) were dissolved in methanol (10 mL) and stirred at room temperature for 18 hours. The reaction mixture was diluted with ether (30 mL) to precipitate the salts and filtered through Celite. Evaporation of the solvent and chromatography on silica gel eluting with 3:1 hexane/ethyl acetate gave 340 mg (51%) of the title compound. $^1$H NMR (CDCl$_3$): δ1.55 (s, 3H), 1.56 (s, 3H), 1.60–1.67 (mult, 4H), 1.79–1.89 (mult, 4H), 3.49 (ddd; J=3.8, 7.7, and 11.8 Hz, 1H), 3.78 (ddd; J=6.3, 6.3 and 12.6 Hz, 1H), 3.81 (ddd; J=6.3, 6.3, and 12.6 Hz, 1H), 4.05 (ddd; J=4.0, 4.0, and 11.6 Hz, 1H), 4.92 (dd, J=3.1 and 7.6 Hz, 1H). Anal calcd for C$_{10}$H$_{20}$O$_2$S: C; 58.78 H; 9.87, S; 15.69. Found C; 58.42, H; 9.73, S; 15.58.

7d. 3-Methyl-3-perhydro-2H-pyran-2-ylthiobutyl {3-[({1-[(3-methyl-3-perhydro-2H-pyran-2-ylthiobutyl) oxycarbonyl](2-imidazolin-2-yl)}methyl)(4-methylphenyl) amino]phenoxy}formate The product of Example 7c (700 mg, 3.5 mmol) was dissolved in tetrahydrofuran (5 mL) and cooled to –78° C.

To this solution was added 2.5 M BuLi (1.38 mL, 3.5 mmol), and the reaction mixture was stirred at –78° C. for 20 minutes. A solution of 1.93 M phosgene in toluene (3.6 mL, 7.0 mmol) was cooled to –78°C. and the cold solution of lithium alkoxide was rapidly cannulated into the phosgene solution. The reaction mixture was stirred at –78° C. for 30 minutes and then warmed to room temperature and stirred for 2 hours. The solution was filtered through a cotton plug and concentrated to give the chloroformate as a syrup. A slurry of 3-[(2-imidazolin-2-ylmethyl)(4-methylphenyl) amino]phenol hydrochloride (500 mg, 1.6 mmol) and triethylamine (650 μL, 4.7 mmol) in methylene chloride (10 mL) was cooled to –78° C. The chloroformate was dissolved in methylene chloride (4 mL) and this solution was added to the slurry. The resulting reaction mixture was stirred at –78° C. for 30 minutes and was then warmed to room temperature and stirred for 20 hours. The reaction mixture was diluted with methylene chloride and then washed successively with 0.1 N HCl, saturated aqueous sodium bicarbonate, and brine; followed by drying over sodium sulfate. Evaporation of the solvent and chromatography on silica gel eluting with 2:1 hexane/ethyl acetate gave 540 mg (46%) of the title compound. $^1$H NMR (CDCl$_3$): δ1.51–2.05 (mult, 16H), 2.32 (s, 3H), 3.46–3.52 (mult, 2H), 3.79 (s, 4H), 4.03–4.08 (mult, 2H), 4.32 (t, J=7.1 Hz, 2H), 4.38 (t, J=7.3 Hz, 2H), 4.89 (s, 2H), 4.94–4.99 (mult. 2H), 6.51 (t, J=2.2 Hz, 1H), 6.57–6.62 (mult, 2H), 7.12 (t, J=8.2 Hz. 1H), 7.13 (d, J=8.0 Hz, 2H), 7.18 (d, J=8.6 Hz, 2H).

7e. 3-Methyl-3-sulfanylbutyl {3-[(4-methylphenyl)({1-[(3-methyl-3-sulfanylbutyl)oxycarbonyl](2-imidazolin-2-yl) }methyl)amino]phenoxy}formate Hydrochloride The product of Example 7d (400 mg, 0.54 mmol), mercaptoethanol (760 μL, 10 mmol), and 4 N HCl in ether (250 μL, 1 mmol) were kept at room temperature for 24 hours. The reaction mixture was diluted with ethyl acetate and then washed with saturated aqueous sodium bicarbonate, water, and brine, and then dried over sodium sulfate. Hydrochloric acid was added and the solvent was evaporated to leave a syrup. The syrup was triturated with ethanol and ether. Decantation of the solvents and subjecting the residue to high vacuum overnight afforded 130 mg of solid. The solid was chromatographed on silica gel eluting with 3:1 hexane/ ethyl acetate to give 30 mg (10%) of the title compound. $^1$H NMR (CDCl$_3$): δ1.43 (s, 12H), 1.75 (s, 1H), 1.76 (s, 1H), 1.97 (t, J=7.1 Hz, 2H), 2.02 (t, J=7.1 Hz, 2H), 2.33 (s, 3H), 3.80 (s, 4H), 4.35 (t, J=7.0 Hz, 2H), 4.41 (t, J=7.3 Hz, 2H), 4.90 (s, 2H), 6.52 (t, J=2.2 Hz, 1H), 6.59 (dd, J=2.1 and 7.9 Hz, 1H), 6.61 (dd, J=2.4 and 8.3 Hz, 1H), 7.13 (t, J=8.2 Hz, 1H), 7.14 (d, J=7.9 Hz, 2H), 7.18 (d, J=8.6 Hz, 2H).

7f. 3-Methyl-3-(nitrosothio)butyl(3-{[(1-{[3-methyl-3-(nitrosothio)butyl]oxycarbonyl}(2-imidazolin-2-yl)) methyl](4-methylphenyl)amino}phenoxy)formate Hydrochloride The product of Example 7e (18 mg, 0.033 mmol) was dissolved in dimethylforamide (200 μL) and 4 N HCl in ether (25 μL, 0.1 mmol) was added. The reaction mixture was cooled to 0° C. and tert-butyl nitrite (12 μL, 0.12 mmol) was added and then the reaction mixture was stirred at for 0° C. for 20 minutes. The solvent was evaporated in vacuo and the solid residue obtained was azeotroped with chloroform to afford the title compound as a foam. $^1$H NMR (DMSO-d$_6$): δ1.89 (s, 6H), 1.92 (s, 6H), 2.30 (s, 3H), 2.62 (t, J=6.6 Hz, 2H), 2.65 (t, J=6.5 Hz, 2H), 3.89–4.00 (mult, 2H), 4.00–4.10 (mult, 2H), 4.38 (t, J=6.7 Hz, 2H), 4.44 (t. J=6.7 Hz, 2H), 5.10 (br s, 2H), 6.61–6.72 (mult, 6H), 6.89 (d, J=8.2 Hz, 1H), 7.09 (d J=8.0 Hz, 1H).

Example 8
4-[2-(Dimethylamino)ethoxy]-2-methyl-5-(methylethyl) phenyl 4-(N-{[(nitrosothio)cyclohexyl]methyl}carbamoyl) butanoate

8a. 4-({4-[2-(Dimethylamino)ethoxy]-2-methyl-5-(methylethyl)phenyl}oxycarbonyl)butanoic Acid The product of Example 6a was dissolved in anhydrous chloroform (32 mL) and glutaric anhydride (0.886 g, 7.77 mmol) was added, followed by DMAP (0.190 g, 1.56 mmol) and triethylamine (0.820 mL, 5,84 mmol). The resulting mixture was stirred at 55° C. for 42 hours. The mixture was cooled down to room temperature and poured into dichloromethane/water mixture. The organic fraction was separated, washed with brine, dried over anhydrous sodium sulfate and concentrated in vacuo to give (1.42 g, 94% yield) of the title compound as a clear oil. $^1$H NMR (CDCl$_3$, 300 MHz): δ1.13–1.18 (d, 6H), 2.04 (s, 3H), 2.04–2.13 (m, 2H), 2.38–2.44 (t, 2H), 2.50 (s, 6H), 2.60–2.66 (t, 2H), 2.96–3.07 (t, 2H), 3.17–3.26 (m, 1H), 4.11–4.16 (t, 2H), 6.65 (s, 1H), 6.79 (s, 1H).

8b. 4-[2-(Dimethylamino)ethoxy]-2-methyl-5-(methylethyl) phenyl 4-{N-[sulfanylcyclohexyl) methyl] carbamoyl}butanoate Under a nitrogen atmosphere, the product of Example 8a (1.4 g, 3.62 mmol) was dissolved in anhydrous chloroform (20 mL) and 1-(aminomethyl)cyclohexane-1-thiol (0.71 g, 4.8 mmol) was added, followed by DMAP (0.195 g, 1.6 mmol). A solution of EDAC (0.764 g, 4.00 mmol) in chloroform (10 mL) was added dropwise and the resulting mixture was stirred at 55° C. for 40 hours. Volatiles were evaporated and the residue was purified by chromatography on silica-gel, eluting with methylene chloride/methanol (15:1) to give (0.930 g, 54% yield) of the title compound as a clear oil. $^1$H NMR (CDCl$_3$,300 MHz):: δ1.13–1.18 (d, 6H), 1.42–1.68 (m, 10H), 2.10 (s, 3H), 2.10–2.13 (m, 2H), 2.36 (s, 6H), 2.34–2.38 (m, 2H), 2.61–2.66 (t, 2H), 2.72–2.78 (t, 2H), 3.17–3.26 (m, 1H), 3.39–3.43 (d, 2H), 4.02–4.07 (t, 2H), 6.05 (s, 1H), 6.66 (s, 1H), 6.79 (s, 1H).

8c. 4-[2-(Dimethylamino)ethoxy]-2-methyl-5-(methylethyl) phenyl 4-(N-{[(nitrosothio)cyclohexyl]methyl}carbamoyl) butanoate Hydrochloride The product of Example 8b (0.285 g, 0.60 mmol) was dissolved in dichloromethane (9 mL) and 2.9 N HCl in ether (0.06 mL) was added. The resulting mixture was cooled to 0° C. and tert-butyl nitrite (0.300 mL, 2.53 mmol) was added, followed by 2.9 NH$_4$Cl in ether (0.05 mL). The reaction mixture was stirred on ice for 45 minutes (0.13 mL, 1.20 mmol), phenol (0.013 g, 0.14 mmol), water (0.13 mL), and trifluoroacetic acid (0.80 mL, 10.4 mmol) were added. After 1 hour of stirring at room temperature, toluene (2 mL) was added and volatiles were evaporated. The residue was purified by flash chromatography on silica gel eluting with hexane/ethyl acetate (2:1) to give the title compound (0.055 g, 60% yield) as a solid. $^1$H NMR (CDCl$_3$, 300 MHz): δ1.49–1.53 (d, 6H, J=2.42 71–1.77 (m, 3H), 2.02–2.09 (m, 7H), 2.27–2.34 (t, 2H), 2.41–2.50 (m, 2H), 2.57–2.74 (t, 2H), 2.74 (s, 6H), 3.17–3.26 (m, 1H), 4.14–4.18 (d, 2H), 4.30–4.34 (t, 2H), 5.75 (s, 1H), 6.68 (s, 1H), 6.80 (s, 1H).

Example 9
4-[2-(Dimethylamino)ethoxy]-2-methyl-5-(methylethyl) phenyl2-({N-[2-methyl-2-(nitrosothio)propyl] carbamoyl}methoxy)acetate, Fumaric Acid Salt

9a. 2-{[N-(2-methyl-2-sulfanylpropyl)carbamoyl] methoxy}acetic Acid

To an ice-cooled suspension of 1-amino-2-methylpropane-2-thiol hydrochloride (4.21 g, 29.72 mmol) in methylene chloride (50 mL) was added triethylamine (4.56 mL, 32.72 mmol), followed by diglycolic anhydride (3.43 g, 29.55 mmol). After stirring at room temperature for 30 minutes, the reaction was concentrated in vacuo and cold 2 N HCl (50 mL) was added to the residue. The mixture was extracted with ethyl acetate (5×30 mL). The combined extracts were washed with brine (30 mL) and dried over anhydrous sodium sulfate. Volatiles were evaporated and the residue was triturated with ether/hexane to afford 5.50 g (84%) of the title compound as a white solid. mp 81–82° C.; $^1$H NMR (CDCl$_3$, 300 MHz): δ1.38 (s, 6H), 1.59 (s, 1H), 3.41 (d, 2H, J=6.4 Hz), 4.20 (s, 2H), 4.24 (s, 2H), 7.48 (br s, 1H), 8.80 (br s, 1H); $^{13}$C NMR (CDCl$_3$, 75 MHz) δ29.83, 44.91, 51.90, 68.39, 70.77, 170.40, 172.84; LCMS (m/e): 239 (M+H$_2$O), 222 (M+1).

9b. 2-({N-[2-methyl-2-(nitrosothio)propyl] carbamoyl}methoxy)acetic Acid

The product of Example 9a (5.76 g, 26.03 mmol) was dissolved in methylene chloride (100 mL) and t-butyl nitrite (3.2 mL, 27.37 mmol) was added. After stirring for 30 minutes at room temperature, the reaction mixture was concentrated in vacuo and the residue was solidified upon cooling. Washing with ether/hexane gave 6.41 g (98%) of the title compound as a green solid. mp 81–83° C.; $^1$H NMR (CDCl$_3$, 300 MHz): δ1.90 (s, 6H), 4.12 (d, 2H, J=6.5 Hz), 4.17 (s, 2H), 4.18 (s, 2H), 7.28 (br s, 1H), 8.49 (br s, 1H); $^{13}$C NMR (CDCl$_3$, 75 MHz,) δ26.75, 49.05, 56.68, 68.41, 70.86, 170.66, 173.04 ; LCMS (m/e): 268 (M+H$_2$O), 251 (M+1). Anal. Calcd for C$_8$H$_{14}$N$_2$O$_5$S: C, 38.39; H, 5.64; N, 11.19; S,12.81, Found: C, 38.56; H,5.76; N, 10.88; S, 12.96.

9c. 4-[2-(Dimethylamino)ethoxy]-2-methyl-5-(methylethyl) phenyl 2-({N-[2-methyl-2-(nitrosothio)propyl] carbamoyl}methoxy)acetate Under a nitrogen the product of Example 6a (4.52 g, 19.1 mmol) was dissolved in anhydrous methylene chloride (60 mL) and 4-dimethylaminopyridine (0.932 g, 7.64 mmol) was added. The resulting solution was cooled to 0° C. and the product of Example 9b (4.77 g, 19.1 mmol) was added, followed by a solution of 1,3-dicyclohexylcarbodiimide (3.93 g, 19.1 mmol) in methylene chloride (30 mL). The resulting mixture was stirred at 0° C. for 1 hour and then at room temperature for 4 hours. The precipitate was filtered, the solvent was evaporated and the residue was purified by flash chromatography on silica gel, eluting with methylene chloride/methanol (40:1) to give 4.18 g (47%) of the title compound as a green oil. $^1$H NMR (CDCl$_3$, 300 MHz): δ1.17 (d, 6H), 1.89 (s, 6H, J=6.9 Hz), 2.09 (s, 3H), 2.35 (s, 6H), 2.76 (t, 2H, J=5.9 Hz), 3.12–3.28 (m, 1H), 4.02–4.10 (m, 4 H), 4.18 (s, 2H), 4.39 (s, 2H), 6.67 (s, 1H), 6.80 (s, 1H), 7.24 (br s, 1H)

9d. 4-[2-(Dimethylamino)ethoxy]-2-methyl-5-(methylethyl) phenyl 2-({N-[2-methyl-2-(nitrosothio)propyl] carbamoyl}methoxy)acetate, Fumaric Acid Salt The product of Example 9c (0.259 g, 0.55 mmol) was dissolved in methanol (3 mL) and fumaric acid (0.064 g, 0.55 mmol) was added. The solvent was evaporated and the residue was recrystallized from the mixture of acetone (1.5 mL), ethyl ether (0.5 mL) and methanol (0.1 mL) to afford 0.156 g (48%) of the title compound as a green crystalline solid. mp 106–107° C.; $^1$H NMR (DMSO, 300 MHz,) δ1.13 (d, 6H), 1.85 (s, 6H), 2.07 (s, 3H), 2.40 (s, 6H), 2.88 (t, 2H), 3.17–3.25 (m, 1H), 3.90 (d, 2H), 4.08–4.15 (m, 4H), 4.50 (s, 2H), 6.59 (s, 2H), 6.89 (d, 2H), 8.22 (t, 1H).

9e. 4-[2-(Dimethylamino)ethoxy]-2-methyl-5-(methylethyl) phenyl 2-({N-[2-methyl-2-(nitrosothio)propyl] carbamoyl}methoxy)acetate, Succinic Acid Salt The product of Example 9c (1.01 g, 2.15 mmol) was dissolved in methanol (6 mL) and succinic acid (0.254 g, 2.15 mmol) was added. The solvent was evaporated and the residue was recrystallized from the mixture of acetone (4.5 mL), ethyl ether (1.5 mL) and methanol (0.2 mL) to afford 0.812 g (64%) of the title compound as a green crystalline solid. mp 72–75° C.; $^1$H NMR (DMSO, 300 MHz): δ1.13 (d, 6H, J=6.9 Hz), 1.85 (s, 6H), 2.07 (s, 3H), 2.31 (s, 6H), 2.41 (s, 4H), 2.76 (t, 2H, J=5.9 Hz), 3.12–3.29 (m, 1H), 3.90 (d, 2H, J=6.5 Hz), 4.06–4.12 (m, 4H), 4.49 (s, 2H), 6.88 (d, 2H, J=2.4 Hz), 8.22 (br t, 1H).

Example 10
4-[2-(dimethylamino)ethoxy]-2-methyl-5-(methylethyl) phenyl 2-[2-(nitrosothio)adamantan-2-yl]ethyl butane-1,4-dioate, Fumaric Acid Salt 10a. Adamantane-2-thione Adamantan-2-one (48.46 g, 322.6 mmol) in pyridine (300 mL) was heated to 90° C. and phosphorous pentasulfide (17.84 g, 40.13 mmol) was added. The reaction was maintained at 90° C. for two hours and at room temperature overnight during which time a precipitate formed. The pyridine solution was decanted and concentrated to dryness. The residual semisolid was treated with hexane (400 mL) to give an orange solution with a light brown suspension. The suspension was removed by filtration. The filtrate was concentrated to dryness and dried to vacuum to give an orange solid (50.36 g). This crude product was purified by filtration through a pad of silica gel (hexane). $^1$H NMR (CDCl$_3$, 300 MHz): δ3.43 (s, 2H), 2.1–1.9 (m, 12H); $^{13}$C NMR (75 MHz, CDCl$_3$): δ222.4, 57.5, 41.1, 36.5, 27.4.

10b. tert-Butyl 2-(2-sulfanyladamantan-2-yl)acetate

To t-butyl acetate (25 mL, 21.6 g, 186 mmol) in dry THF (400 mL) at −78° C. was added lithium diisopropylamide monotetrahydrofuran (1.5 M solution in cyclohexane, 100 mL, 150 mmol) under nitrogen and the reaction mixture was stirred at −78° C. for 40 minutes. The product of Example 10a (21.88 g, 131.57 mmol) in THF (400 mL) was added. The cold bath was removed and the reaction was stirred at room temperature for two hours. The reaction was diluted with methylene chloride and 2 M HCl (75 mL) was added. The organic phase was separated, washed with brine (4×40 mL), dried (MgSO$_4$), filtered, and concentrated. The crude product was purified by filtration through a pad of silica gel (5% EtOAc/95% hexane) to give the title compound (34.67 g, 122.7 mmol, 93%). R$_f$=0.48 (EtOAc/hexane 1:19); $^1$H NMR (CDCl$_3$, 300 MHz): δ2.87 (s, 2H), 2,47 (d, J=11.5, 2H), 2.38 (s, 1H), 2.11 (d, J=11.9, 2H), 1.98 (s, 2H), 1.96(m, 2H), 1.84–1.62 96 (m, 6H), 1.47 (s, 9H); $^{13}$C NMR (75 MHz, CDCl$_3$): δ170.8, 80.7, 54.1, 47.3, 39.0, 38.2, 37.2, 36.6, 34.0, 33.3, 28.2, 27.5, 26.9. APIMS (IS, NH$_4$OAc) m/e 283 (MH$^+$); Anal. Calcd for C$_{16}$H$_{26}$O$_2$S (282.44): C, 68.04; H, 9.28 Found: C, 68.14; H, 9.30.

10c. 2-(2-Sulfanyladamantan-2-yl)ethan-1-ol

To a 0° C. cooled solution tert-butyl 2-(2-sulfanyladamantan-2-yl)acetate (4.1 g, 24.1 mmol) in anhydrous dichloromethane (40 mL) lithium aluminum hydride (1 M solution in THF) (40 mL) was added dropwise over a period of 20 minutes. The reaction mixture was stirred at 0° C. for further 15 minutes and then at room temperature for 30 minutes. The excess LiAlH$_4$ was destroyed by the addition of ethyl acetate. The reaction mixture was then poured over ice cold water, acidified with 1 N HCl and extracted with dichloromethane (2×200 mL). The combined extracts were washed with brine (1×75 mL), dried over sodium sulfate, filtered and solvent evaporated at reduced pressure to give the title compound (3.1 g), mp 68–70° C.; $^1$H NMR (CDCl$_3$): δ1.16–1.9 (m, 11H), 2.1 (m, 2H), 2.22 (t, J=6.9 Hz, 3H), 2.43 (m, 2H), 3.93 (t, J=6.9 Hz, 2H); $^{13}$C NMR (CDCl$_3$): δ26.8, 27.7, 33.2, 33.9, 38.2, 39.1, 43.4, 55.8, 59.4; LRMS (APIMS) (m/z) 230 (M+18) (M+NH$_4$).

10d. 3-{[2-(2-sulfanyladamantan-2-yl)ethyl] oxycarbonyl}propanoic Acid

A solution of succinic anhydride (10 mmol, 1.00 g) and 2-(2-sulfanyladamantan-2-yl)ethan-1-ol (2.214 g, 10.4 mmol) in toluene (30 mL) was heated at 70° C. for 16 hours. Removal of the solvent under vacuum provided a low-melting solid, 3.12 g, 10 mmol. $^1$H NMR (CDCl$_3$, 300 MHz): δ4.44 (t, J=7.4 Hz, 2H), 2.68 (m, 2H), 2.63 (m, 2H), 2.43 (m, 2H), 2.25 (t, J=7.4 Hz, 2H), 2.11 (m, 2H), 1.88–1.62 (m, 10H); MS (CI/NH$_3$) (m/e) 330 (M+NH$_4$), 279 (M-SH), 195, 161.

10e. 3-({2-[2-(nitrosothio)adamantan-2-yl] ethyl}oxycarbonyl)propanoic Acid

To a solution of the product of Example 10a (3.12 g, 10 mmol) and HCl/isopropanol (5.3 M, 0.2 mL) in 100 mL dichloromethane at 0° C. was added tert-butylnitrite (11 mmol, 1.260 g, 1.45 mL). The ice bath was removed, and the solution was stirred for an additional 1.5 hours at room temperature. The reaction mixture was washed with water, and dried over magnesium sulfate. After rotary evaporation, the crude material was purified via column chromatography (5% methanol/chloroform) to yield a green oil. The oil solidified upon cooling overnight, and was triturated with hexane to give a green solid. The compound was filtered and dried under vacuum, 1.93 g, 5.65 mmol, 57%, yield. mp 63–70° C.; $^1$H NMR (CDCl$_3$, 300 MHz): δ4.28 (t, J=7.3 Hz, 2H), 3.07 (t, J=7.3 Hz, 2H), 2.65 (m, 2H), 2.59 (m, 2H), 2.55 (m, 2H), 2.44 (m, 2H), 2.07 (m, 3H), 1.93 (m, 2H), 1.86 (m, 3H), 1.74 (m, 2H); MS (CI, NH$_3$) (m/e) 359 (M+NH$_4$), 329 (M+NH$_4$-NO).

10f. 4-[2-(dimethylamino)ethoxy]-2-methyl-5-(methylethyl)phenyl 2-[2-(nitrosothio)adamantan-2-yl]ethyl butane-1,4-dioate To a solution of the product of Example 6a (1.117 g, 4.71 mmol) and the product of Example 10b (1.93 g, 5.65 mmol) in anhydrous dichloromethane (100 mL) were added 1-ethyl-3-(3-dimethylaminopropyl)carbamide hydrochloride (EDAC) (1.083 g, 5.65 mmol) and dimethylaminopyridine (DMAP) (0.23 g, 1.88 mmol) at room temperature under nitrogen atmosphere. The reaction mixture was stirred at room temperature overnight. After dilution with dichloromethane organic layer was washed with water, brine, dried over sodium sulfate, filtered, and solvent was evaporated at reduced temperature to give the crude product that was purified by column chromatography on silica gel using 10% methanol in chloroform to give the pure product 2.63 g in 99% yield. $^1$H NMR (CDCl$_3$, 300 MHz): δ6.82 (s, 1H), 6.69 (s, 1H), 4.32 (t, J=7.4 Hz, 2H), 4.08 (t, J=5.9 Hz, 2H), 3.28 (sept., J=6.9 Hz, 1H), 3.10 (t, J=7.3 Hz, 2H), 2.90 (t, J=6.9 Hz, 2H), 2.79 (t, J=5.9 Hz, 2H), 2.73 (t, J=6.9 Hz, 2H), 2.45 (m, 1H), 2.38 (s, 6H), 2.13 (s, 3H), 2.08 (m, 4H), 2.00–1.86 (m, 5H), 1.75 (m, 2H), 1.19 (d, J=6.9 Hz, 6H); MS (CI/NH$_3$) (m/e) 561 M+H), 531 (M+1-NO, 498, 428, 366, 295.

10g. 4-[2-(dimethylamino)ethoxy]-2-methyl-5-(methylethyl)phenyl 2-[2-(nitrosothio)adamantan-2-yl]ethyl butane-1,4-dioate, Fumaric Acid Salt A mixture of the product of Example 10c (2.627 g, 4.68 mmol), fumaric acid (4.68 mmol, 0.534 g) and butylated hydroxytoluene (BHT, 26 mg) in acetone was concentrated under vacuum, and addition of ether caused a green solid to separate. The compound was collected and dried to provide the title material, 1.781 g, 56% yield. mp 87–88° C. (dec.); $^1$H NMR (DMSO-d$_6$, 300 MHz): δ6.86 (s, 1H), 6.78 (s, 1H), 6.58 (s, 2H), 4.21 (t, J=7.1 Hz, 2H), 4.11 (t, J=5.5 Hz, 2H), 3.20 (sept., J=6.9 Hz, 1H), 3.00 (t, J=7.2 Hz, 2H), 2.89 (t, J=5.4 Hz, 2H), 2.81 (m, 2H), 2.62 (m, 2H), 2.41 (s, 6H), 2.39 (m, 2H), 2.04–1.55 (m, 12H), 2.02 (s, 3H), 1.10 (d, J=6.9 Hz, 6H).

Example 11
4-[2-(Dimethylamino)ethoxy]-2-methyl-5-(methylethyl)phenyl 2-[({2-[2-(nitrosothio)adamantan-2-yl]ethyl}oxycarbonyl)methoxlyacetate, Succinic Acid Salt 11a. 2-{[Benzyloxycarbonyl]methoxy}acetic Acid Diglycolic anhydride (4.11 g, 31.9 mmol) was dissolved in methylene chloride and benzyl alcohol (3.3 g, 31.9 mmol) was added, followed by triethylamine (3.22 g, 31.9 mmol). The reaction mixture was stirred at room temperature for 4 hours. Toluene (20 mL) was added, volatiles were evaporated and the residue was dried on vacuum pump overnight to afford 7.17 g of the title compound as a colorless oil. $^1$H NMR (CDCl$_3$, 300 MHz): δ4.17 (s, 2H), 4.26 (s, 2H), 5.18 (s, 2H), 7.21–7.42 (m, 5H).

11b. 4-[2-(Dimethylamino)ethoxy]-2-methyl-5-(methylethyl)phenyl 2-{[benzyloxycarbonyl]methoxy}acetate Under a nitrogen atmosphere the product of Example 11a (7.15 g, 31.9 mmol) was dissolved in anhydrous chloroform (30 mL) and the product of Example 6a (7.56 g, 31.9 mmol) was added, followed by 4-dimethylaminopyridine (3.89 g, 31.9 mmol). A solution of EDAC (6.09 g, 31.9 mmol) in chloroform (15 mL) was added dropwise and the resulting mixture was stirred at room temperature for 22 hours. Volatiles were evaporated and the residue was purified by flash chromatography on silica gel, eluting with methylene chloride/methanol (20:1) to give 2.9 g of the title compound as a colorless oil. $^1$H NMR (CDCl$_3$, 300 MHz): δ1.14 (d, 6H, J=6.9Hz), 2.10 (s, 3H), 2.93 (s, 6H), 3.08–3.18 (m, 1H), 3.49 (br t, 2H), 4.35 (s, 2H), 4.45–4.52 (m, 4H), 5.21 (s, 2H), 6.71 (s, 1H), 6.85 (s, 1H), 7.27–7.37 (m, 5H).

11c. 2-[({4-[2-(Dimethylamino)ethoxy]-2-methyl-5-(methylethyl)phenyl}oxycarbonyl)methoxy]acetic Acid Under the nitrogen atmosphere the product of Example 11b (2.9 g, 6.55 mmol) was dissolved in methanol (60 mL) and palladium on activated carbon (0.20 g) was added. The nitrogen atmosphere line was exchanged with 1 atmosphere hydrogen and the resulting mixture was stirred at room temperature for 2 hours 30 minutes. The reaction mixture was filtered through celite and volatiles were evaporated to give 2.25 g (97%) of the title compound as a white solid. $^1$H NMR (CDCl$_3$, 300 MHz): δ1.15 (d, 6H, J=6.9 Hz), 2.05 (s, 3H), 2.79 (s, 6H), 3.07–3.19 (m, 1H), 3.34 (br s, 2H), 4.20 (s, 2H), 4.33 (br s, 2H), 4.46 (s, 2H), 6.66 (s, 1H), 6.84 (s, 1H).

11d. 4-[2-(Dimethylamino)ethoxy]-2-methyl-5-(methylethyl)phenyl 2-[({2-[2-(nitrosothio)adamantan-2-yl]ethyl}oxycarbonyl)methoxy]acetate Under a nitrogen atmosphere the product of Example 11c (0.800 g, 2.27 mmol) was dissolved in anhydrous chloroform (20 mL) and the product of Example 12a (0.614 g, 2.54 mmol) was added, followed by 4-dimethylaminopyridine (0.124 g, 1.04 mmol). A solution of EDAC (0.485 g, 2.54 mmol) in chloroform (7 mL) was added dropwise and the resulting mixture was stirred at room temperature for 4 hours. Volatiles were evaporated and the residue was purified by flash chromatography on silica gel, eluting with methylene chloride/methanol (40:1) to (20:1) to give 0.298 g of the title compound as a green oil. $^1$H NMR (CDCl$_3$, 300 MHz): δ1.13 (d, 6H, J=6.9 Hz), 1.64–1.88 (m, 7H), 1.97–2.07 (m, 3H), 2.08 (s, 3H), 2.32 (s, 6H), 2.33–2.46 (m, 2H), 2.51 (br s, 2H), 2.73 (t, 2H J=5.8 Hz), 3.07 (t, 2H, J=7.4 Hz), 3.12–3.23 (m, 1H), 4.02 (t, 2H, J=5.8 Hz), 4.25 (s, 2H), 4.33 (t, 2H, J=7.4 Hz), 4.43–4.49 (m 2H), 6.64 (s, 1H), 6.80 (s, 1H).

11e. 4-[2-(Dimethylamino)ethoxy]-2-methyl-5-(methylethyl)phenyl 2-[({2-[2-(nitrosothio)adamantan-2-yl]ethyl}oxycarbonyl)methoxy]acetate, Succinic Acid salt The product of Example 11d (0.298 g, 0.52 mmol) was dissolved in methanol (3 mL) and succinic acid (0.061 g, 0.52 mmol) was added. The solvent was evaporated and the residue was recrystallized from the mixture of acetone (1.5 mL) and ethyl ether (0.5 mL) to afford 0.220 g (68%) of the title compound as a green crystalline solid. mp 59–62° C.; $^1$H NMR (DMSO, 300 MHz): δ1.09 (d, 6H), 1.58–2.05 (m, 13H), 2.30 (s, 6H), 2.39 (s, 4H), 2.40–2.44 (m, 4H), 2.75 (t, 2H), 3.02 (t, 2H), 3.12–3.24 (m, 1H), 4.06 (t, 2H), 4.18–4.30 (m, 4H), 4.47 (s, 2H), 6.86 (d, 2H).

Example 12
4-[2-(dimethylamino)ethoxy]-2-methyl-5-(methylethyl)phenyl 2-[2-(nitrosothio)adamantan-2-yl]ethyl Pentane-1,5-dioate, Citrate Salt 12a. 2-[2-(Nitrosothio)adamantan-2-yl]ethan-1-ol To a 0° C. cooled solution of the compound from Example 10c (1.06 g, 5 mmol) in anhydrous dichloromethane (40 mL) was added t-butyl nitrite (7.5 mmol, 890 μL). The reaction mixture was stirred at 0° C. for 30 minutes and then at room temperature for 30 minutes. The solvent was removed at reduced pressure and product was recrystallized from ethyl ether/hexane to give 1.2 g (80% yield) pure product as green crystalline solid, mp 77–79° C.; $^1$H NMR (CDCl$_3$): δ1.7–1.74 (m, 2H), 1.83–1.93 (m, 5H), 2.06 (m, 3H), 2.42–2.53 (m, 4H), 2.99 (t, J=7.3 Hz, 2H), 3.83 (t, J=7.6 Hz, 2H); $^{13}$C NMR (CDCl$_3$): δ27.3, 27.4, 33.2, 33.9, 35.6, 38.97, 39.96, 59.1, 68.2; LRMS (APIMS) (m/z) 259 (M+18) (M+NH$_4$).

12b. 4-[Benzyloxycarbonyl]butanoic Acid

A mixture of glutaric anhydride (11.4 g, 0.1 mol) and benzyl alcohol (11.4 mL, 1.1 equiv.) in toluene (200 mL) was heated at 70° C. for 2 days. Solvent was evaporated at reduced pressure to give the product which was dried under high vacuum and was pure enough to use in the next step. $^1$H NMR (CDCl$_3$): δ1.96 (t, J=7.2 Hz, 2H), 2.44 (q, J=7.0 Hz, 4H), 5.13 (s, 2H), 7.33 (s, 5H).

12c. 4-[2-(Dimethylamino)ethoxy]-2-methyl-5-(methylethyl)phenyl Phenylmethyl Pentane-1,5-dioate To a solution of the product of Example 6a (2.37 g, 10 mmol) and the product of Example 12b (2.22 g, 10 mmol) in anhydrous dichloromethane (125 mL) were added 1-ethyl-3-(3-dimethylaminopropyl)carbamide hydrochloride (EDAC) (3.82 g, 20 mmol) and dimethylaminopyridine (DMAP) (2.44 g, 20 mmol) at room temperature under nitrogen atmosphere. The reaction mixture was stirred at room temperature overnight. After dilution with dichloromethane organic layer was washed with water, brine, dried over sodium sulfate, filtered, and solvent was evaporated at reduced temperature to give the crude product that was purified by column chromatography over silica gel using 5% methanol in dichloromethane to give the pure product 2.79 g in 56% yield. $^1$H NMR (CDCl$_3$): δ1.13 (d, J=6.9 Hz, 6H), 1.97–2.1 (m, 2H), 2.06 (s, 3H), 2.49 (t, =7.3 Hz, 2H), 2.61 (t, J=7.4 Hz, 2H), 2.73 (s, 6H), 3.17 (m, 1H), 3.26 (t, J=5.0 Hz, 2H) 4.33 (t, J=5.0 Hz, 2H), 5.11 (s, 2H), 6.67 (s, 1H), 6.78 (s, 1H), 7.30 (s, 5H); $^{13}$C NMR (CDCl$_3$): δ16.0, 20.0, 22.6 (2×C), 26.4, 32.9, 33.1, 43.9, 56.9, 64.2, 66.2, 113.7, 119.6, 127.7, 128.1, 128.4, 135.5, 135.7, 143.2, 152.3, 171.3, 172.5; LRMS (APIMS) (m/z) 442 (M+1).

12d. 4-({4-[2-(Dimethylamino)ethoxy]-2-methyl-5 (methylethyl)phenyl}oxycarbonyl)butanoic Acid Hydrogenation of the product of Example 12c (4.41 g, 10 mmol) in ethanol (130 mL) at 5–10 psi was performed in presence of catalyst amount of 10% Pd/C in a par hydrogenation apparatus for 3 hour. The catalyst was filtered off, washed with ethanol (10 mL) and combined filtrate was evaporated at reduced pressure to give an oily product which upon trituration with hexane/ethyl acetate (9:1) gave 3.5 g of the pure product as a white crystalline solid. mp 109–110° C.; $^1$H NMR (CDCl$_3$): δ1.10 (d, J=6.9 Hz, 6H), 1.96 (t, =7.3 Hz, 2H), 2.02 (s, 3H), 2.34 (t, J=7.3 Hz, 2H), 2.55 (t, J=7.4 Hz, 2H), 2.86 (s, 6H), 3.11 (m, 1H), 3.45 (t, J=4.3 Hz, 2H), 4.35 (t, J=4.4 Hz, 2H), 6.65 (s, 1H), 6.74 (s, 1H), 11.0 (br s, 1H); $^{13}$C NMR (CDCl$_3$): δ16.1, 20.8, 22.6 (2×C), 26.4, 33.5 34.5, 44.1 (2×C), 56.9, 65.0, 113.5, 119.5, 127.6, 128.1, 128.4, 135.5, 135.7, 143.1, 152.8, 171.7, 177.4; LRMS (APIMS) (m/z) 352 (M+1).

12e. 4-[2-(Dimethylamino)ethoxy]-2-methyl-5-(methylethyl)phenyl 2-[2-(nitrosothio)adamantan-2-yl]ethyl Pentane-1,5-dioate To a solution of the product of Example 12d (1.755 g, 5 mmol) in anhydrous dichloromethane (25 mL) were added successively 1-ethyl-3-(3-dimethylamino-propyl)carbamide hydrochloride (EDAC) (1.054 g, 5.5 mmol) and DMAP (0.671 g, 5.5 mmol) at room temperature under nitrogen atmosphere. The reaction mixture was then cooled to 0° C. temperature and a solution of the product of Example 12a (1.205 g, 5 mmol) in anhydrous dichloromethane (25 mL) was added dropwise at 0° C. The reaction mixture was stirred at 0° C. for 30 minutes and then slowly allowed to warm to room temperature and further stirred at room temperature for 5 hours. The solvent was evaporated at reduced pressure and residue was extracted with ethyl acetate and water. The organic layer was separated, washed with water, brine, dried over sodium sulfate, and solvent was evaporated at reduced pressure to give the crude product that was purified by column chromatography over silica gel using 5% methanol in dichloromethane to give the pure product 2.37 g in 86% yield. $^1$H NMR (CDCl$_3$): δ1.15 (d, J=6.9 Hz, 6H), 1.7–1.95 (m, 8H), 2.0–2.1 (m, 8H), 2.35 (s, 6H), 2.40–2.53 (m, 5H), 2.60 (t, J=7.2 Hz, 2H), 2.77 (t, J=5.8 Hz, 2H), 3.06 (t, J=7.3 Hz, 2H), 3.24 (m, 1H), 4.06 (t, J=5.7 Hz, 2H), 4.26 (t, J=7.2 Hz, 2H), 6.65 (s, 1H), 6.78 (s, 1H); $^{13}$C NMR (CDCl$_3$): δ16.2, 20.1, 22.6, 26.4, 26.6, 27.1, 27.3, 33.1, 33.2, 33.4, 35.7, 38.8, 45.9, 58.3, 61.1, 66.9, 67.7, 113.7, 119.4, 127.3, 135.9, 142.7, 153.7, 171.4, 172.7; LRMS (APIMS) (m/z ) 575 (M+1).

12f. 4-[2-(Dimethylamino)ethoxy]-2-methyl-5-(methylethyl)phenyl 2-[2-(nitrosothio)adamantan-2-yl]ethyl Pentane-1,5-dioate, Citrate Salt The product of Example 12e (460 mg, 0.8 mmol) was dissolved in acetone (5 mL), butylated hydroxytoluene (BHT) (5 mg) was added and solution was cooled to 0° C. Solution of citric acid (154 mg, 0.8 mmol) in methanol was added dropwise at 0° C. temperature under nitrogen atmosphere and stirred at 0° C. for 10 minutes. The citrate salt crystallized out from the solution was filtered off, washed with acetone/hexane, and dried under high vacuum. The pure product 300 mg was obtained as green crystalline solid in 49% yield, mp 153–162° C.; $^1$H NMR (d$_6$-DMSO): δ1.12 (d, J=6.8 Hz, 6H), 1.7–2.0 (m, 8H), 2.1 (s, 3H), 2.30–2.51 (m, 11H), 2.65 (s, 6H), 3.01 (m, 3H), 2.60 (t, J=7.2 Hz, 2H), 2.77 (t, J=5.8 Hz, 2H), 3.06 (t, J=7.3 Hz, 2H), 3.24 (m, 1H), 3.25 (m, 3H), 4.2 (m, 3H), 6.85 (s, 1H), 6.89 (s, 1H).

Example 13

4-[2-(Dimethylamino)ethoxy]-2-methyl-5-(methylethyl) phenyl 4-{N-[2-methyl-2-(nitrosothio)propyl] carbamoyl}butanoate, Citrate Salt 13a. 4-[N-(2-Methyl-2-sulfanylpropyl)carbamoyl]butanoic Acid To a suspension of 1-Amino-2-methylpropane-2-thiol hydrochloride (1.41 g, 10 mmol) in anhydrous dichloromethane (10 mL) was added triethylamine (1.5 mL) at 0° C. The mixture was stirred at 0° C. for 10 minutes and glutaric anhydride (1.14 g, 10 mmol) in anhydrous dichloromethane (20 mL) was added at 0° C. under argon atmosphere. The reaction mixture was stirred at 0° C. for 10 minutes and then at room temperature for 2 hours. The solvent was evaporated at reduced pressure and the residue was extracted with ethyl acetate and water. The combined ethyl acetate extracts were washed with 1 N HCl, dried over sodium sulfate and solvent was evaporated at reduced pressure to give colorless oil, which upon trituration with ethyl ether/hexane gave 1.57 g of the title compound as a colorless powder in 72% yield, mp 101–104° C.; $^1$H NMR (CDCl$_3$): δ1.31 (s, 6H), 1.94 (m, 2H), 2.22–2.38 (m, 4H), 3.33 (d, J=6.1 Hz, 2H), 6.28 (s, 1H), 9.2 (br s, 1H; LRMS (APIMS) (m/z) 220 (M+1).

13b. 4-{N-[2-Methyl-2-(nitrosothio)propyl] carbamoyl}butanoic Acid

To a 0° C. cooled solution of the product of Example 13a (410 mg, 1.87 mmol) in anhydrous dichloromethane (25 mL) was added t-BuONO (357 mL, 3 mmol). The reaction mixture was stirred at 0° C. for 30 minutes and then at room temperature for 30 minutes. The reaction mixture was then diluted with dichloromethane, washed with water, brine, dried over sodium sulfate and solvent was evaporated at reduced pressure to give an oily product, which was purified by column chromatography over silica gel using methanol-:dichloromethane (5:95) as an eluant to give the pure product 460 mg in 99% yield, mp 104–107° C. (dec.); $^1$H NMR (CDCl$_3$): 67 0.95–1.0 (m, 2H), 1.01 (s, 6H), 1.42 (m, 4H), 3.12 (t, J=6.2 Hz, 2H), 4.75 (s, 1H), 6.75 (br s, 1H); $^{13}$C NMR (CD$_3$COCD$_3$): δ21.2, 22.6 (2×C), 32.9, 34.9, 48.9, 57.9, 172.8, 173.9; LRMS (APIMS) (m/z) 249 (M+1).

13c. 4-[2-(Dimethylamino)ethoxy]-2-methyl-5-(methylethyl)phenyl 4-{N-[2-methyl-2-(nitrosothio)propyl] carbamoyl}butanoate To a solution of the product of Example 6a (118 mg, 0.5 mmol) in anhydrous dichloromethane (5 mL) were added successively EDAC (96 mg, 0.5 mmol) and DMAP (61 mg, 0.5 mmol). The reaction mixture was stirred at room temperature for 2 minutes and then it was cooled to 0° C. To this was then added solution of the product of Example 13b (124 mg, 0.5 mmol) in a mixture of dichloromethane (2 mL) and DMF (100 mL). The reaction mixture was then stirred at 0° C. for 30 minutes and then at room temperature for 5 hours and was then extracted with dichloromethane. The organic layer was dried over sodium sulfate, solvent was evaporated at reduced pressure and the green residue obtained was purified by column chromatography over silica gel using methanol:dichloromethane (1:9) to give 170 mg of the pure title compound as green oil in 73% yield. $^1$H NMR (CDCl$_3$): δ1.14 (d, J=6.9 Hz, 6H), 1.85 (s, 6H), 2.0 (m, 2H), 2.06 (s, 3H), 2.31 (m, 2H), 2.33 (s, 6H), 2.60 (t, J=7.1 Hz, 2H), 2.74 (t, J=5.9 Hz, 2H), 3.23 (m, 1H), 4.03 (m, 4H), 6.03 (m, 1H), 6.64 (s, 1H), 6.76 (s, 1H); $^{13}$C NMR (CDCl$_3$): δ16.2, 20.8, 22.6 (2×C), 26.5, 26.8, 31.4, 35.3, 46.2, 49.3, 53.4, 57.2, 58.4, 67.0, 113.6, 119.3, 127.3, 135.9, 142.6, 153.6, 171.8, 172.4; LRMS (APIMS) (m/z) 468 (M+1).

13d. 4-[2-(dimethylamino)ethoxy]-2-methyl-5-(methylethyl)phenyl 4-{N-[2-methyl-2-(nitrosothio)propyl] carbamoyl}butanoate, Fumaric Acid Salt To a solution of the product of Example 13c (920 mg, 1.97 mmol) in acetone (8 mL) BHT (9.3 mg) was added under nitrogen atmosphere and solution was cooled to 0° C. To this was added solution of fumaric acid (228 mg, 1.97 mmol) in methanol (3 mL). The reaction mixture was stirred at 0° C. for 5 minutes and then at room temperature for 15 minutes.

The solvents were evaporated at reduced pressure and the residue obtained was triturated with ethyl ether/hexane to a give green solid (910 mg), which was recrystallized from acetone/ethyl ether/methanol containing 1% BHT at −20° C. to give green crystalline solid. mp 105–113° C.; $^1$H NMR ($d_6$-DMSO): δ1.12 (d, J=6.9 Hz, 6H), 1.84 (s, 6H), 1.8–1.9 (m, 2H), 2.03 (s, 3H), 2.23 (t, J=7.2 Hz, 2H), 2.31 (s, 6H), 2.54 (t, J=7.4 Hz, 2H), 2.75 (t, J=5.4 Hz, 2H), 3.19 (m, 1H), 3.84 (d, J=6.4 Hz, 2H), 4.07 (t, J=5.6 Hz, 2H), 6.58 (s, 2H), 6.81 (s, 1H), 6.86 (s, 1H), 8.28 (t, J=5.4 Hz, 1H); LRMS (APIMS) (m/z) 468 (M+1).

13e. 4-[2-(Dimethylamino)ethoxy]-2-methyl-5-(methylethyl)phenyl 4-{N-[2-methyl-2-(nitrosothio)propyl]carbamoyl}butanoate, Citrate Salt To a solution of the product of Example 13c (140 mg, 0.299 mmol) in acetone (2 mL) BHT (1.5 mg) was added under nitrogen atmosphere and solution was cooled to 0° C. To this was added solution of citric acid (58 mg, 0.299 mmol) in methanol (1 mL). The reaction mixture was stirred at 0° C. for 5 minutes and then at room temperature for 15 minutes. The solvents were evaporated at reduced pressure and the green solid obtained was recrystallized from acetone/ethyl ether/methanol containing 1% BHT at −20° C. to give 110 mg of the title compound as a green solid. mp 123–127° C.; $^1$H NMR ($d_6$-DMSO): δ1.12 (d, J=6.9 Hz, 6H), 1.82–1.86 (m, 2H), 1.84 (s, 6H), 2.04 (s, 3H), 2.23 (t, J=7.5 Hz, 2H), 2.5–2.64 (m, 8H), 3.1 (m, 1H), 3.84 (d, J=6.4 Hz, 2H), 4.19 (t, J=5.2 Hz, 2H), 6.85 (s, 1H), 6.89 (s, 1H), 8.25 (t, J=5.4 Hz, 1H); LRMS (APIMS) (m/z) 468 (M+1).

Example 14

4-[2-(Dimethylamino)ethoxy]-2-methyl-5-(methylethyl) phenyl 4-{N-methyl-N-[2-methyl-2-(nitrosothio)propyl]carbamoyl}butanoate, Fumaric Acid Salt 14a. 4-[N-Methyl-N-(2-methyl-2-sulfanylpropyl)carbamoyl]butanoic Acid To a suspension of 1-N-methylmino-2-methylpropane-2-thiol hydrochloride (3.01 g, 10 mmol) in anhydrous dichloromethane (30 mL) was added triethylamine (3 mL) at 0° C. The mixture was stirred at 0° C. for 10 minutes and glutaric anhydride (2.28 g, 20 mmol) in anhydrous dichloromethane (20 mL) was added at 0° C. under argon atmosphere. The reaction mixture was stirred at 0° C. for 10 minutes and then at room temperature for 2 hours. The solvent was evaporated at reduced pressure and the residue was extracted with ethyl acetate and water. The combined ethyl acetate extracts were washed with 1 N HCl, dried over sodium sulfate and solvent was evaporated in vacuo to give colorless oil, which upon trituration with ethyl ether/hexane gave 3.1 g of the title compound as an oil in 66.5% yield. $^1$H NMR (CDCl$_3$): δ1.32 (s, 6H), 1.92 (m, 2H), 2.39 (m, 4H), 3.13 (s, 3H), 3.50 (s, 3H); $^{13}$C NMR (CDCl$_3$): δ19.9, 31.1 (2×C), 32.4 33.1, 38.7, 46.1, 60.7, 173.7, 177.7; LRMS (APIMS) (m/z) 234 (M+1).

14b. 4-{N-Methyl-N-[2-methyl-2-(nitrosothio)propyl]carbamoyl}butanoic Acid

To a 0° C. cooled solution of the product of Example 14a (2.79 g, 12 mmol) in anhydrous dichloromethane (120 mL) was added t-BuONO (3 mL, 25 mmol). The reaction mixture was stirred at 0° C. for 30 minutes and then at room temperature for 30 minutes. The reaction mixture was then diluted with dichloromethane, washed with water, brine, dried over sodium sulfate and solvent was evaporated at reduced pressure to give an oily product, which was purified by column chromatography over silica gel using methanol:dichloromethane (5:95) as an eluant to give the pure product 2.88 g in 92% yield. $^1$H NMR (CDCl$_3$): δ1.85 (s, 6H), 1.91 (m, 2H), 2.40 (m, 4H), 2.98 (s, 3H), 4.1 (s, 2H), 6.41 (br s, 1H); $^{13}$C NMR (CDCl$_3$): δ19.9, 27.4, 30.8 (2×C), 32.4, 33.0, 38.6 46.1, 58.14, 174.1, 177.2; LRMS (APIMS) (m/z) 263 (M+1).

14c. 4-[2-(Dimethylamino)ethoxy]-2-methyl-5-(methylethyl)phenyl 4-{N-methyl-N-[2-methyl-2-(nitrosothio)propyl]carbamoyl}butanoate To a solution of the product of Example 6a (3.318 g, 14 mmol) in anhydrous dichloromethane (100 mL) were added successively EDAC (2.1 g, 11 mmol) and DMAP (1.32 g, 11 mmol). The reaction mixture was stirred at room temperature for 2 minutes and then it was cooled to 0° C. To this was then added solution of the product of Example 14b (2.88 g, 11 mmol) in a mixture of dichloromethane (10 mL). The reaction mixture was then stirred at 0° C. for 15 minutes and then at room temperature overnight. The work up involved extraction with dichloromethane, washing it with 5% aqueous potassium carbonate solution, water, and brine. The organic layer was dried over sodium sulfate, solvent was evaporated at reduced pressure and the green residue obtained was purified by column chromatography over silica gel using methanol:dichloromethane (1:19) to give 3.41 g of the title compound as green oil in 51% yield. $^1$H NMR (CDCl$_3$): δ1.15 (d, J=6.8 Hz, 6H), 1.88 (s, 6H), 2.09–2.1 (m, 2H), 2.1 (s, 3H), 2.37 (s, 6H), 2.49 (t, J=7.1 Hz, 2H), 2.66 (t, J=7.1 Hz, 2H), 2.75 (t, J=5.7 Hz, 2H), 3.0 (s, 3H), 3.24 (m, 1H), 4.07 (t, J=5.6 Hz, 2H), 4.12 (s, 2H), 6.65 (s, 1H), 6.78 (s, 1H); $^{13}$C NMR (CDCl$_3$): δ16.1, 20.2, 22.5 (2×C), 26.5, 27.4, 32.4, 33.1, 38.5, 45.8, 57.91, 58.3, 66.9, 113.7, 119.4, 127.3, 135.9, 142.7, 153.5, 171.9, 173.4; LRMS (APIMS) (m/z) 482 (M+1).

14d. 4-[2-(Dimethylamino)ethoxy]-2-methyl-5-(methylethyl)phenyl 4-{N-methyl-N-[2-methyl-2-(nitrosothio)propyl]carbamoyl}butanoate, Fumaric Acid Salt To a solution of the product of Example 14c (910 mg, 1.89 mmol) in acetone (5 mL) BHT (9 mg) was added under nitrogen atmosphere and solution was cooled to 0° C. To this was added solution of fumaric acid (219 mg, 1.89 mmol) in methanol (3 mL). The reaction mixture was stirred at 0° C. for 5 minutes and then at room temperature for 15 minutes. The solvents were evaporated at reduced pressure and the residue obtained was triturated with ethyl ether/hexane to give a green solid which was recrystallized from acetone/ethyl ether containing 1% BHT at −20° C. to give 520 mg of the title compound as a green solid, mp 109–118° C.; $^1$H NMR ($d_6$-DMSO): δ1.12 (d, J=6.9 Hz, 6H), 1.82 (s, 2H), 1.88 (s, 6H), 2.04 (s, 3H), 2.40 (s, 6H), 2.45 (m, 2H), 2.59 (t, J=7.1 Hz, 2H), 2.89 (t, J=4.9 Hz, 2H), 3.06 (s, 2H), 3.20 (m, 1H), 4.07 (s, 2H), 4.11 (t, J=5.2 Hz, 2H), 6.58 (s, 2H), 6.83 (s, 1H), 6.86 (s, 1H); LRMS (APIMS) (m/z) 482 (M+1).

Example 15

4-[2-(Dimethylamino)ethoxy]-2-methyl-5-(methylethyl) phenyl 5-{4-[2-methyl-2-(nitrosothio)propyl]piperazinyl}-5-oxopentanoate, Hydrochloride Salt 15a. 2-Methyl-1-piperazinylpropane-2-thiol Piperazine (7.72 g, 89.8 mmol) was dissolved in benzene (10 mL) and 2,2-dimethylthiirane (3.16 g, 35.9 mmol) was added. The reaction mixture was stirred at 80° C. for 1 hour, poured into the water and extracted with ethyl acetate (3×100 mL). The combined organic extracts were washed with brine and dried over anhydrous sodium sulfate. Volatiles were evaporated and the residue was dried on vacuum pump overnight to afford 3.9 g of the title compound. $^1$H NMR (CDCl3, 300 MHz): δ1.29 (s, 6H), 2.34 (s, 2H), 2.58 (t, 4H), 2.63 (s, 1H), 2.85 (t, 4H).

15b. 5-[4-(2-Methyl-2-sulfanylpropyl)piperazinyl]-5-oxopentanoic Acid

Glutaric anhydride (0.655 g, 5.7 mmol) was dissolved in toluene (10 mL) and the product of Example 15a (1.0 g, 5.7 mmol) was added. The reaction mixture was stirred at 80° C. for 20 hours. Volatiles were evaporated and the residue was purified by flash chromatography on silica gel, eluting with methylene chloride/methanol (100:1) to (15:1) to give 0.674 g of the title compound as a white solid. $^1$H NMR (CDCl$_3$, 300 MHz): δ1.33 (s, 6H), 1.81–2.00 (m, 2H), 2.33–2.48 (m, 6H), 2.52–2.74 (m, 4H), 3.47 (br t, 2H), 3.60 (br t, 2H).

15c. 4-[2-(Dimethylamino)ethoxy]-2-methyl-5-(methylethyl)phenyl 5-[4-(2-methyl-2-sulfanylpropyl)piperazinyl]-5-oxopentanoate Under a nitrogen atmosphere the product of Example 15b (0.486 g, 1.69 mmol) was dissolved in anhydrous chloroform (12 mL) the product of Example 6a (0.400 g, 1.69 mmol) was added, followed by 4-dimethylaminopyridine (0.206 g, 1.69 mmol). A solution of 1,3-dicyclohexylcarbodiimide (0.348 g, 1.69 mmol) in chloroform (5 mL) was added dropwise and the resulting mixture was stirred at room temperature for 24 hours. The precipitate was removed by filtration and the filtrate was concentrated in vacuo. The residue was purified by flash chromatography on silica gel, eluting with methylene chloride/methanol (30:1) to give 0.760 g (89%) of the title compound. $^1$H NMR (CDCl$_3$, 300 MHz): δ1.17 (d, 6H, J=6.9 Hz), 1.32 (s, 6H), 1.98–2.11 (m, 6H), 2.36–2.42 (m, 8H), 2.47 (t, 2H, J=7.4 Hz), 2.54–2.70 (m, 4H), 2.84 (t, 2H, J=5.7 Hz), 3.19–3.32 (m, 1H), 3.42–3.53 (m, 4H), 3.58–3.67 (m, 2H), 4.09 (t, 2H, J=5.7 Hz), 6.66 (s, 1H), 6.80 (s, 1H).

15d. 4-[2-(Dimethylamino)ethoxy]-2-methyl-5-(methylethyl)phenyl 5-{4-[2-methyl-2-(nitrosothio)propyl]piperazinyl}-5-oxopentanoate The product of Example 15c (0.760 g, 1.40 mmol) was dissolved in methylene chloride (14 mL) and 4N HCl in ether (0.500 mL) was added. The resulting mixture was cooled to 0° C. and tert-butyl nitrite (0.270 mL, 2.80 mmol) was added. The reaction mixture was stirred on ice for 10 minutes and volatiles were evaporated. The residue was purified by flash chromatography on silica gel, eluting with methylene chloride/methanol (30:1) to give 0.380 g (45%) of the title compound. $^1$H NMR (CDCl$_3$, 300 MHz): δ1.16 (d, 6H), 1.87 (s, 6H), 1.98–2.12 (m, 5H), 2.35 (s, 6H), 2.45 (t, 2H), 2.59 (t, 4H), 2.65 (t, 2H), 2.77 (t, 2H), 3.01 (s, 2H), 3.18–3.22 (m, 1H), 3.42 (t, 2H), 3.51–3.62 (m, 2H), 4.05 (t, 2H), 6.65 (s, 1H), 6.78 (s, 1H).

15e. 4-[2-(Dimethylamino)ethoxy]-2-methyl-5-(methylethyl)phenyl 5-{4-[2-methyl-2-(nitrosothio)propyl]piperazinyl}-5-oxopentanoate, Hydrochloride Salt The product of Example 15d (0.380 g, 0.62 mmol) was dissolved in methylene chloride (3 mL) and 4N HCl in ether (1 mL) was added. The solvent was evaporated to afford 0.415 g of the title compound as a green solid. mp 30–42° C. $^1$H NMR (CDCl$_3$, 300 MHz): δ1.11 (d, 6H), 1.92–2.06 (m, 5H), 2.17 (s, 6H), 2.45 (br s, 2H), 2.63 (br s, 2H), 2.91 (s, 6H), 3.01–3.22 (m, 3H), 3.31–3.61 (m, 4H), 3.69–3.98 (m, 4H), 4.12–4.39 (m, 4H), 6.68 (s, 1H), 6.79 (s, 1H).

Example 16

4-[2-(Dimethylamino)ethoxy]-2-methyl-5-(methylethyl)phenyl 2-(2-{N-[2-methyl-2-(nitrosothio)propyl]carbamoyl}phenyl)benzoate 16a. 2-{2-[N-(2-methyl-2-sulfanylpropyl)carbamoyl]phenyl}benzoic Acid To an ice-cooled suspension of 1-amino-2-methyl-2-propanethiol hydrochloride (1.08 g, 7.62 mmol) in methylene chloride (20 mL) was added triethylamine (1.2 mL, 8.61 mmol) followed by dibenzo[c,e]oxepin-5,7-dione (1.68 g, 7.42 mmol). After stirring at room temperature for 1 h, cold 2 N HCl (50 mL) was added. After separation, the aqueous layer was extracted with dichloromethane (2×15 mL). The combined organic layers were washed with brine and dried under sodium sulfate. The solvent was removed and the resulting residue was triturated with hexane to give the title compound as white solid (2.44 g, 98.9%). mp 150–153° C.; $^1$H NMR (CDCl$_3$, 300 MHz): δ1.03 (s, 3H), 1.12 (s, 3H), 1.36 (s, 1H), 3.15 (dd, J=13.7 and 5.7 Hz, 1H), 3.38 (dd, J=13.7 and 6.9 Hz, 1H), 6.92 (t, J=6.1 Hz, 1H), 7.09–7.17 (m 2H), 7.38–7.48 (m, 4H), 7.57–7.61 (m, 1H), 7.80–7.83 (m, 1H); $^{13}$C NMR (CDCl$_3$, 75 MHz,): δ29.36, 29.75, 44.66, 53.01, 127.28, 127.96, 128.04, 129.38, 129.93, 130.06, 130.20, 131.19, 132.02, 134.69, 138.90, 140.11, 170.99, 171.24; LCMS (m/e): 330 (M+1).

16b. 2-(2-{N-[2-methyl-2-(nitrosothio)propyl]carbamoyl}phenyl)benzoic Acid

To a solution of the product of Example 16a (1.23 g, 3.73 mmol) in methylene chloride (25 mL) at room temperature was added t-butyl nitrite (0.46 mL, 3.93 mmol). After 30 minutes, the reaction was concentrated and the residue was triturated with hexane to afford the title compound as a green solid (1.32 g, 98.6%). mp 121–123° C.; $^1$H NMR (CDCl$_3$, 300 MHz): δ1.50 (s, 3H), 1.64 (s, 3H), 3.86 (dd, J=14.1 and 5.6 Hz, 1H), 4.08 (dd, J=14.1 and 7.1 Hz, 1H), 6.05 (br s, 1H), 6.89 (t, J=6 Hz, 1H), 7.06–7.82 (m, 8H); $^{13}$C NMR (CDCl$_3$, 75 MHz): δ26.28, 26.86, 49.74, 56.54, 127.39, 127.93, 128.02, 129.56, 129.79, 130.02, 130.39, 131.37, 131.42, 134.76, 138.83, 140.42, 171.01, 171.33; LCMS (m/e): 359 (M+1).

16c. 4-[2-(Dimethylamino)ethoxy]-2-methyl-5-(methylethyl)phenyl 2-(2-{N-[2-methyl-2-(nitrosothio)propyl]carbamoyl}phenyl)benzoate The product of Example 16b (170 mg, 0.718 mmol) and dimethylaminopyridine (35.0 mg, 287 mmol) were dissolved in CHCl$_3$ (5 mL) and cooled to 0° C. A solution of the product of Example 6a (257 mg, 718 mmol) in CHCl$_3$ (2 mL) was added followed by a solution of 1-[3-(dimethylamino)propyl]-3-ethylcarbodiimide hydrochloride (137 mg, 718 mmol) in CHCl$_3$ (5 mL). The mixture was allowed to warm to room temperature and stirred for 5.5 hours. The reaction mixture was diluted with methylene chloride, washed with water and brine, and dried (MgSO$_4$). Evaporation of the solvent followed by chromatography on silica gel eluting with 30:1 methylene chloride/methanol gave 208 mg (50%) of the title compound as a green oil. $^1$H NMR (CDCl$_3$): δ1.17 (d, J=6.8, 6H), 1.38 (s, 3H), 1.64 (s, 3H), 2.02 (s, 3H), 2.33 (d, J=4.6, 6H), 2.73 (t, J=5.8, 2H), 3.28–3.23 (m, 1H), 3.69 (dd, J=5.0, 14.1, 1H), 4.02 (t, J=5.5, 2H), 4.11 (dd, J=7.7, 14.1, 1H), 6.59 (s, 1H), 6.63 (s, 1H), 6.88 (br t, NH), 7.11–7.08 (m, 1H), 7.53–7.30 (m, 5H), 7.64–7.60 (m, 1H), 7.99 (dd, J=7.6, 1.3, 1H).

Example 17

4-[2-(Dimethylamino)ethoxy]-2-methyl-5-(methylethyl)phenyl 1-[3-methyl-3-(nitrosothio)butanoyl]piperidine4-carboxylate, Succinic Acid Salt 17a. Ethyl 1-[3-methyl-3-(2,4,6-trimethoxyphenylthio)butanoyl]piperidine-4 Carboxylate Ethyl isonipecotate (1.99 g, 12.7 mmol) was dissolved in anhydrous chloroform (30 mL) the product of Example 4a (4.0 g, 12.7 mmol) was added, followed by 4-dimethylaminopyridine (1.55 g, 12.7 mmol). A solution of 1-(3-dimethylaminopropyl)-3-ethylcarbodiimide hydrochloride (2.42 g, 12.7 mmol) in chloroform (10 mL) was added dropwise and the resulting mixture was stirred at room temperature for 22 hours. Volatiles were evaporated and the residue was purified by flash chromatography on silica gel, eluting with hexane/ethyl acetate (1:1) to give 4.1 g (72%) of the title compound. $^1$H NMR (CDCl$_3$, 300 MHz): δ1.17 (t, 3H), 1.44 (s, 6H), 1.46–1.62 (m, 2H), 1.75–1.84 (m, 2H), 2.31–2.47 (m, 1H), 2.65 (s, 2H), 2.66–2.78 (m, 1H), 2.97–3.08 (m, 1H), 3.56–3.78 (m, 11H), 3.79–3.88 (m, 1H), 4.05 (q, 2H), 4.28–4.37 (m, 1H), 6.03 (s, 2H).

17b. 1-[3-Methyl-3-(2,4,6-trimethoxyphenylthio)butanoyl] piperidine-4-carboxylic Acid The product of Example 17a (2.44 g, 5.39 mmol) was dissolved in ethanol (25 mL) and a solution of sodium hydroxide (1.94 g, 48.5 mmol) in water (12 mL) was added. The reaction mixture was stirred at reflux temperature for 20 minutes and volatiles were evaporated. The residue was cooled to 0° C. and 2N HCl (25 mL) was added to produce a white precipitate. The reaction mixture was concentrated in vacuo, and the precipitate was separated by filtration. The solid was dissolved in methylene chloride, washed with brine, and dried over anhydrous sodium sulfate. Volatiles were evaporated to give 1.92 g (84%) of the title compound. $^1$H NMR (CDCl$_3$, 300 MHz): δ1.56–1.75 (m, 2H), 1.85 (d, 6H, J=1.70 Hz), 1.87–1.99 (m, 2H), 2.51–2.60 (m, 1H), 2.77 (s, 1H), 3.02 (br t, 2H), 3.72–3.86 (m, 11H), 4.04–4.19 (m, 2H), 5.75 (br s, 1H), 6.11 (s, 2H).

17c. 4-[2-(Dimethylamino)ethoxy]-2-methyl-5-(methylethyl)phenyl 1-[3-methyl-3-(2,4,6-trimethoxyphenylthio)butanoyl]piperidine-4-carboxylate Under a nitrogen atmosphere the product of Example 17b (1.92 g, 4.52 mmol) was dissolved in anhydrous chloroform (30 mL) and the product of Example 6a (1.07 g, 4.52 mmol) was added, followed by 4-dimethylaminopyridine (0.551 g, 4.52 mmol). A solution of 1-(3-dimethylaminopropyl)-3-ethylcarbodiimide hydrochloride (0.863 g, 4.52 mmol) in chloroform (20 mL) was added dropwise and the resulting mixture was stirred at room temperature for 48 hours. Volatiles were evaporated and the residue was purified by flash chromatography on silica gel, eluting with methylene chloride/methanol (40:1) to (30:1) to give 1.95 g (67%) of the title compound. $^1$H NMR (CDCl$_3$, 300 MHz): δ1.16 (d, 6H, J=6.9 Hz), 1.54 (s, 6H), 1.74–1.84 (m, 3H), 2.01–2.13 (m, 5H), 2.44 (s, 6H), 2.76 (s, 3H), 2.78–2.91 (m, 2H), 3.22–3.28 (m, 2H), 3.74–3.88 (m, 11H), 3.93–4.08 (m, 1H), 4.12 (t, 2H, J=5.7 Hz), 4.44–4.52 (m, 1H), 6.11 (s, 2H), 6.67 (s, 1H), 6.78 (s, 1H).

17d. 4-[2-(Dimethylamino)ethoxy]-2-methyl-5-(methylethyl)phenyl 1-(3-methyl-3-sulfanylbutanoyl)piperidine-4-carboxylate The product of Example 17c (1.95 g, 3.03 mmol) was dissolved in methylene chloride (21 mL) and anisole (1.5 mL), phenol (1.5 g), water (1.5 mL) and trifluoroacetic acid (9 mL) were added. After 1 hour 20 minutes of stirring at room temperature, toluene (25 mL) was added and volatiles were evaporated. The residue was purified by flash chromatography on silica gel, eluting with hexane/ethyl acetate (9:1) to (1:1), and then with methylene chloride/methanol (20:1) to give 1.1 g (79%) of the title compound. $^1$H NMR (CDCl$_3$, 300 MHz): δ1.16 (d, 6H), 1.55 (s, 6H), 1.76–1.94 (m, 2H), 2.01–2.16 (m, 5H), 2.55 (s, 1H), 2.69 (s, 2H), 2.72–2.82 (m, 2H), 2.83 (s, 6H), 3.09–3.28 (m, 2H), 3.52 (br s, 2H), 3.99 (d, 1H), 4.43 (br s, 2H), 4.54 (d, 1H), 6.70 (s, 1H), 6.80, (s, 1H), 17e. 4-[2-(Dimethylamino)ethoxy]-2-methyl-5-(methylethyl)phenyl 1-[3-methyl-3-(nitrosothio)butanoyl] piperidine-4-carboxylate The product of Example 17d (0.970 g, 2.10 mmol) was dissolved in methanol (15 mL) and 4N HCl in ether (0.400 mL) was added. The resulting mixture was cooled to 0° C. and tert-butyl nitrite (0.810 mL, 6.3 mmol) was added. The reaction mixture was stirred on ice for 30 minutes and volatiles were evaporated. The residue was purified by flash chromatography on silica gel, eluting with methylene chloride/methanol (40:1) to (30:1) to give 0.629 g (61%) of the title compound. $^1$H NMR (CDCl$_3$, 300 MHz): δ1.16 (d, 6H, J=6.9 Hz), 1.57–1.86 (m, 2H), 1.96–2.13 (m, 11H), 2.36 (s, 6H), 2.77 (t, 2H, J=5.9 Hz), 2.81–2.94 (m, 2H), 3.05–3.27 (m, 4H), 3.86 (br d, 1H), 4.06 (t, 2H, J=5.9 Hz), 4.49 (br d, 1H), 6.66 (s, 1H), 6.75 (s, 1H).

17f. 4-[2-(Dimethylamino)ethoxy]-2-methyl-5-(methylethyl)phenyl 1-[3-methyl-3-(nitrosothio)butanoyl] piperidine-4-carboxylate, Succinic Acid Salt The product of Example 17e (0.628 g, 1.27 mmol) was dissolved in methanol (3 mL) and succinic acid (0.150 g, 1.27 mmol) was added. The solvent was evaporated and the residue was recrystallized from the mixture of acetone (3 mL) and ethyl ether (1 mL) to afford 0.340 g of the title compound as a green crystalline solid. mp 84–85° C. $^1$H NMR (300 MHz, DMSO): δ1.13 (d, 6H), 1.38–1.72 (m, 2H), 1.90–2.11 (m, 11H), 2.32 (s, 6H), 2.41 (s, 4H), 2.76 (t, 2H), 2.78–2.94 (m, 2H), 3.07–3.11 (m, 2H), 3.34 (s, 2H), 3.90 (d, 1H), 4.08 (t, 2H), 4.29 (d, 1H), 6.82 (s, 1H), 6.87 (s, 1H).

Example 18

4-[2-(Dimethylamino)ethoxy]-2-methyl-5-(methylethyl) phenyl 2,2-bis[(nitrooxy)methyl]-3-(nitrooxy)propyl Pentane-1,5-dioate 18a. 2-(Hydroxymethyl)-2-[(1,1,2,2-tetramethyl-1-silapropoxy)methyl]propane-1,3- diol [Pentaerythritol Mono-tert-butyldiphenylsilyl Ether]

Pentaerythritol [2,2-bis(hydroxymethyl)propane-1,3-diol] (10.55 g, 77 mmol) was taken up in 100 mL of dry pyridine. Tert-butyldiphenylsilyl chloride (4.26 g, 15 mmol, 0.2 eq) was then added dropwise over 10 minutes to the pyridine solution at ambient temperature. The reaction mixture was stirred at ambient temperature for 24 hours at which point TLC (EtOAc) indicated that the reaction was complete. The reaction was worked-up by diluting the reaction mixture with 250 mL of EtOAc and washing the organic layer with 10% HCl (3×200 mL). The organic layer was dried over sodium sulfate and then concentrated in vacuo to afford a thick pale yellow oil. Column chromatography on 200 g of silica gel eluting with EtOAc followed by concentration of the appropriate fractions afforded 5.01 g of the product as a clear colorless oil which solidified very slowly upon standing (86%). $^1$H NMR (CDCl$_3$, 300 MHz): δ1.08 (s, 9H), 3.66 (s, 2H), 3.74 (s, 6H), 7.42 (m, 6H), 7.65 (m, 4H); MS (70 eV, EI) 392 (M+NH$_4$)$^+$.

18b. Nitro{3-(nitrooxy)-2-[(nitrooxy)methyl]-2-[(1,1,2,2-tetramethyl-1-silapropoxy)methyl]propyl}oxy (Pentaerythritol Mono-tert-butyldiphenylsilyl Ether Trinitrate)

The product of Example 18a (332 mg, 0.89 mmol) was dissolved in 4 mL of dry methylene chloride. Fuming nitric acid (335 mg, 5.32 mmol, 6 eq, 0.24 mL of the 90% nitric acid) and acetic anhydride (1.20 mL) were premixed (exothermic) and then the pale yellow solution was added dropwise to the methylene chloride solution at ambient temperature. The reaction mixture was stirred at ambient temperature for 30 minutes at which point TLC (7:3 EtOAc/hexanes) indicated that the reaction had gone to completion. The reaction was worked-up by the dilution with methylene chloride (20 mL) followed by washing with 2×10 mL of sodium bicarbonate (saturated aqueous). The organic layer was then dried over sodium sulfate and then the solvent was concentrated in vacuo to afford 400 mg of a pale yellow oil which was used as is for the desilylation reaction (88.6%). $^1$H NMR (CDCl$_3$, 300 MHz): δ0.99 (s, 9H), 3.64 (s, 2H), 4.40 (s, 6H), 7.35 (m, 6H), 7.53 (m, 4H); MS (70 eV, EI) 527 (M+NH$_4$)$^+$.

18c. 2,2-Bis[(nitrooxy)methyl]-3-(nitrooxy)propan-1-ol (Pentaerythritol Trinitrate)

The product of Example 18b (400 mg, 0.79 mmol) was dissolved in 5 mL of THF. Tetrabutyl-n-butylammonium fluoride (1.2 eq, 0.94 mmol, 0.94 mL of the 1M solution in THF) was added at ambient temperature to the trinitrate solution producing a dark brown solution. The reaction mixture was stirred at ambient temperature for 1.5 hours at which point TLC (1:9 EtOAc/hexanes) indicated that the reaction had gone to completion. The reaction mixture was worked-up by passing the solution through a short pad of silica gel, eluting with 1:1 EtOAc/hexanes. Concentration of the solvent in vacuo afforded a pale yellow oil. This oil was chromatographed on 8 10×20 cm 0.25 mm analytical TLC plates eluting first with 1×1:9 EtoAc/hexanes followed by 2×1:3 EtOAc/hexanes. Extraction of the desired band into EtOAc followed by concentration of the solvent in vacuo afforded 150 mg of the product as a pale yellow (71%). $^1$H NMR (CDCl$_3$, 300 MHz): δ3.71 (s, 2H), 4.51 (s, 6H); MS (70 eV, EI) 289 (M+NH$_4$)$^+$.

18d. 4-[2-(Dimethylamino)ethoxy]-2-methyl-5-(methylethyl)phenyl 2,2-bis[(nitrooxy)methyl]-3-(nitrooxy)propyl Pentane-1,5-dioate The product of Example 12d (739 mg, 2.10 mmol) and the product of Example 18c (627 mg, 2.31 mmol, 1.1 eq) are dissolved in 10 mL of dry methylene chloride under Ar in an oven-dried round-bottomed flask at ambient temperature. A small crystal of DMAP was added at ambient temperature followed immediately by the addition of EDAC (463 mg, 2.42 mmol, 1.15 eq). The reaction mixture was stirred at ambient temperature for 18 h at which time TLC (3:7 EtOAc/Hexanes) indicated reaction to be complete. The reaction was worked-up by dilution with methylene chloride and washing 2×10 mL of water and then 1×10 mL of brine. The organic layer was dried over sodium sulfate, the solvent evaporated in vacuo and then preadsorbed onto 2 g of silica gel. The reaction was then flash chromatographed on 15 g of silica gel eluting first with 250 ml of 1:1 EtOAc/hexanes, then 250 mL of EtOAc, and finally 250 mL 1:1 EtOH/EtOAc. Concentration of the appropriate fractions in vacuo and removal of residual solvent on vacuum afforded 820 mg of the trinitrate ester as an extremely viscous pale yellow oil (64.5%). $^1$H NMR (CDCl$_3$, 300 MHz): δ1.16 (d, 6H, J=6.9 Hz), 2.08 (pent, 2H, J=7.2 Hz), 2.10 (s, 3H), 6.67 (s, 1H), 2.52 (t, 2H, J=7.2 Hz), 2.52 (s, 6H), 2.64 (t, 2H, J=7.2 Hz), 2.98 (br, 2H), 3.22 (sept, 1H, J=6.9 Hz), 4.19 (t, 2H, J=5.4 Hz), 4.22 (s, 2H), 4.55 (s, 6H), 6.80 (s, 1H); $^{13}$C NMR (75.5 MHz, CDCl$_3$): δ171.82, 171.27, 153.15, 142.92, 135.84, 127.49, 119.48, 113.80, 69.29, 65.86, 61.69, 57.90, 45.21, 42.13, 32.85, 32.78, 26.56, 22.60, 19.89, 16.11, 14.15; MS (70 eV, EI) 605 (M+1)$^+$.

Example 19
In Vivo Comparative Erectile Responses—I

Male New Zealand white rabbits weighing 2.5 kg were used as the animal model. Animals were first relaxed with an i.m. injection of 25 mg/kg ketamine prior to anesthesia with a bolus i.v. injection of 10 mg/kg Profol and maintained with i.v. infusion at 0.5 mg/kg/minutes. Ventilation of the animals was performed with 1% halothane plus 0.8 L/min O$_2$ and 1 L/min N$_2$O. A 22 gauge angiocatheter was placed in the femoral artery for measurement of systemic blood pressure. A dorsal incision was made in the penis and the corpora cavemosum exposed and cannulated with a 21 gauge butterfly needle to measure intracavernosal pressure.

Drugs at various concentrations were delivered intracavernosally at a volume of 150 μl through a 25 gauge needle. A 150 μl solution of a mixture of papaverine (30 mg/kg), phentolamine (1 mg/kg) and prostaglandin El (10 μg/ml) (pap/phent/PGE1) was injected in the corpora as a standard solution for comparison with the response of yohimbine, Example 1, Example 2, and the combination of yohimbine and Example 1. This pap/phent/PGE1 mixture is considered to cause a maximal erection-inducing effect.

Figure 2:
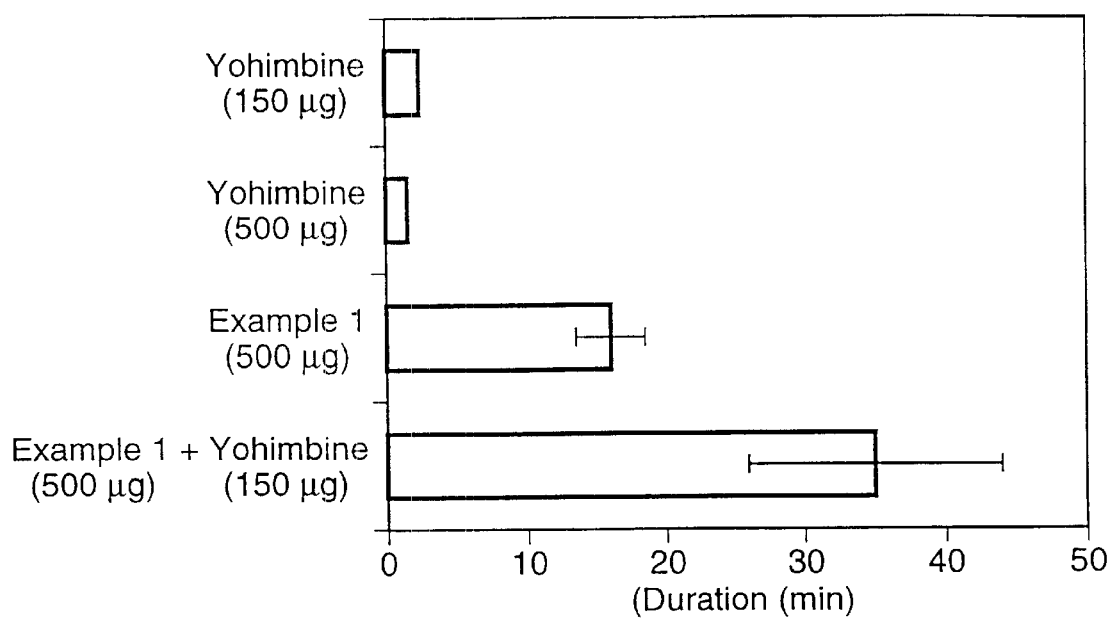
FIG. 2 shows the duration of the erectile response in vivo in the anesthetized rabbit upon intracavemosal administration of yohimbine (150 μg, 500 μg), Example 1 (500 μg), and a combination of yohimbine (150 μg) and Example 1 (500 μg). The ordinate indicates the various drugs given and the abscissa is the duration in minutes.

As shown in FIG. 1, yohimbine dose dependently induced erectile response in the anesthetized rabbit. A 500 μg dose of Example 1 was able to induce near maximal response relative to the standard dose of pap/phent/PGE1. A combination of the submaximal dose of yohimbine (150 μg) and Example 1 (500 μg) also induced maximum erectile response. Yohimbine at both the submaximal and maximal efficacy doses produced very short duration of action (FIG. 2). Example 1 produced a much longer duration of action. The duration of action is potentiated by a combination of Example 1 and yohimbine which is longer than the sum of the duration of each of these compounds alone (FIG. 2).

Figure 3:
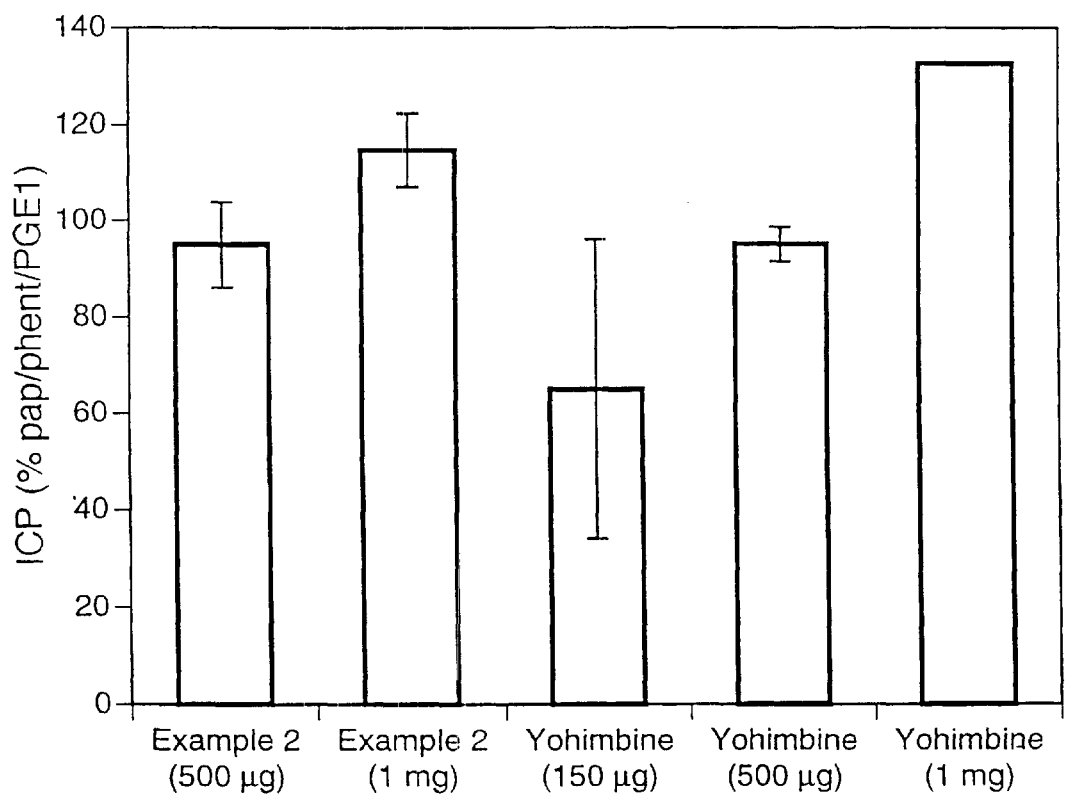
FIG. 3 shows the percent peak erectile response in vivo compared to that produced by 150 μl of pap/phent/PGE1 (30 mg/ml:1 mg/ml:10 μg/ml) in the anesthetized rabbit following the intracavernosal injection of 150 μl of yohimbine (150 μg, 500 μg and 1 mg) and Example 2 (500 μg, 1 mg). The ordinate is the percent response of intracavernosal pressure relative to that produced by pap/phent/PGE1 and the abscissa indicates the various doses of yohimbine and Example 2 given.

FIG. 3 shows that the compound of Example 2 at the 500 μg dose is equipotent to the standard dose of pap/phent/PGE1. A higher dose of the compound of Example 2 (1 mg) is at least equal to or more efficacious than the standard dose of the pap/phent/PGE1 mixture.

Figure 4:
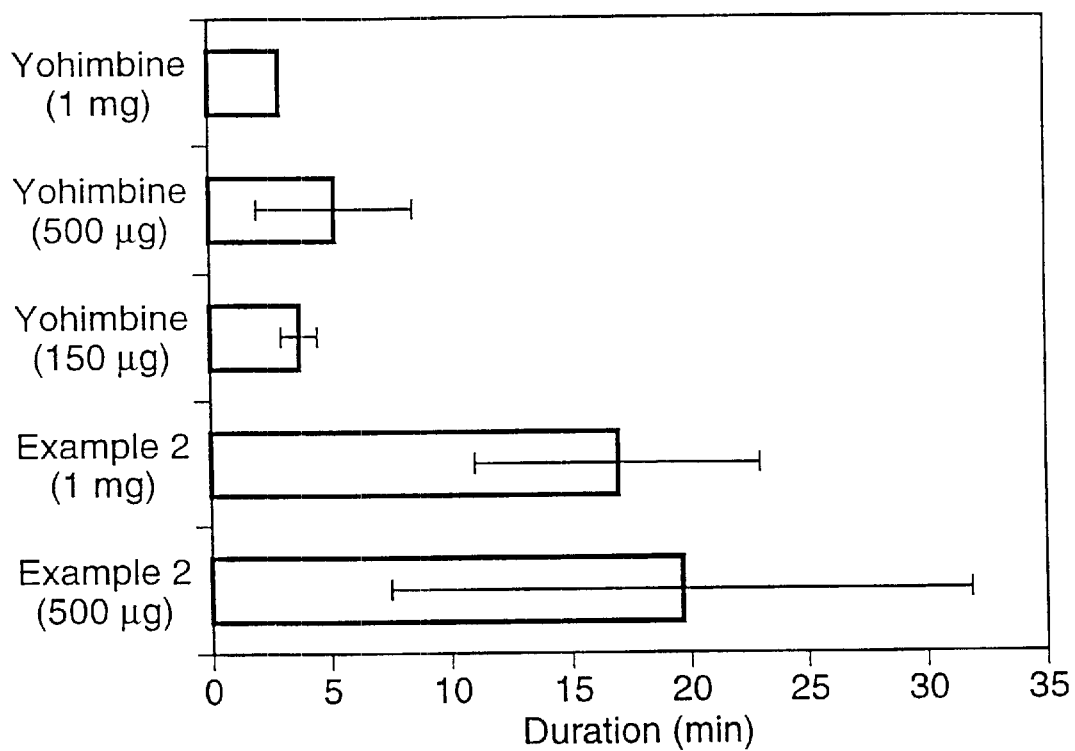
FIG. 4 shows the duration of the erectile response in vivo in the anesthetized rabbit upon intracavernosal administration of yohimbine (150 μg, 500 μg and 1 mg) and Example 2 (500 μg and 1 mg). The ordinate indicates the various doses of yohimbine and Example 2 given and the abscissa is the duration in minutes.
Figure 5A:
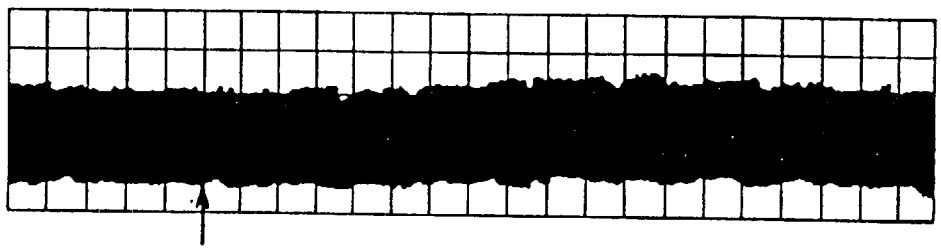
FIG. 5A shows the effects of intracavernosal injections of Example 2 (500 μg) on systemic blood pressure in the anesthetized rabbit. For comparison.
Figure 5B:
FIG. 5B shows the effects of intracavernosal injections of the standard mixture of pap/phent/PGE1 on systemic blood pressure in the anesthetized rabbit.

FIG. 4 shows that the compound of Example 2 has the advantage of producing longer duration of action compared to yohimbine. FIG. 5A demonstrates that a dose (500 μg) of the compound of Example 2 effective in the erectile response did not produce any effect on systemic blood pressure upon intracavernosal injection. However, FIG. 5B demonstrates that a standard dose of the mixture of pap/phent/PGE1 produced a significant decrease in systemic blood pressure upon intracavernosal injection, suggesting that the compound of Example 2 lacks this side effect.

Figure 6:
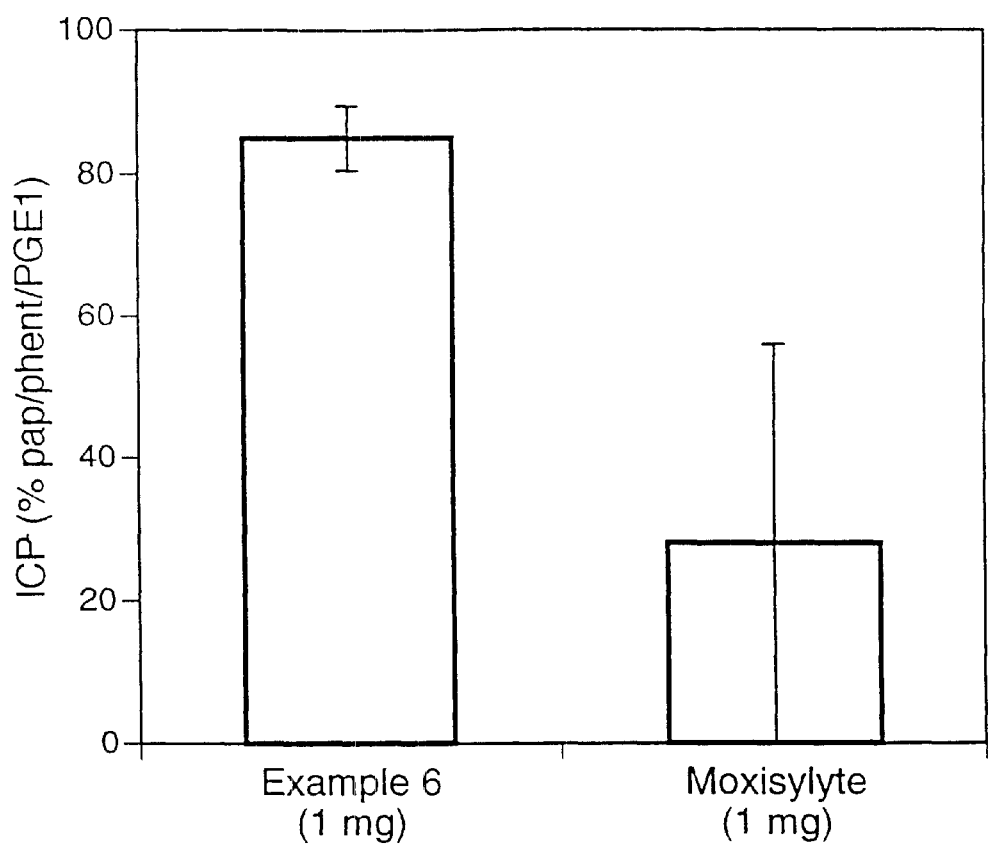
FIG. 6 shows the percent peak erectile response in vivo compared to that produced by 150 μl of pap/phent/PGE1 (30 mg/ml:1 mg/ml:10 μg/ml) in the anesthetized rabbit following the intracavemosal injection of moxisylyte (1 mg) and Example 6 (1 mg). The ordinate is the percent response of intracavemosal pressure relative to that produced by pap/phent/PGE1 and the abscissa indicates the dose of moxisylyte and Example 6 given.
Figure 7:
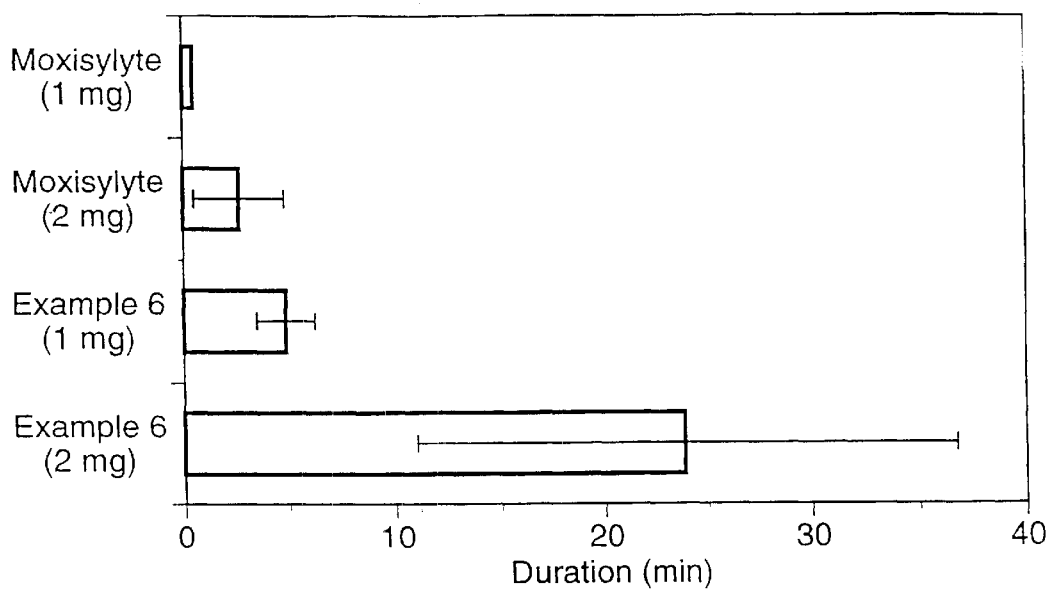
FIG. 7 shows the duration of the erectile response in vivo in the anesthetized rabbit upon intracavernosal administration of moxisylyte (1 and 2 mg) and Example 6 (1 and 2 mg). The ordinate indicates the dose of moxisylyte and Example 6, and the abscissa is the duration in minutes.

FIG. 6 shows that intracavernosal administration of 1 mg of Example 6 is more efficacious than 1 mg moxisylyte in inducing the erectile response in vivo in the anesthetized rabbit. FIG. 7 shows that a 1 mg dose of Example 6 produces a longer duration of erectile response compared to 1 mg moxisylyte. Also, FIG. 7 shows that 2 mg of Example 6 produces a much longer duration of action compared to 2 mg moxisylyte.

Example 20
In vivo Comparative Erectile Responses—II

White New Zealand male rabbits (2.6–3.0 kg) were anesthetized with pentobarbital sodium (30 mg/kg). The femoral artery was exposed and indwelled with PE 50 tubing connected to a transducer for recording systemic arterial blood pressure. The ventral aspect of the penis was then exposed via surgical cut and intracavernosal blood pressure was measured using a 23 gauge needle inserted to the corpus cavernosum. The contralateral corpus cavemosum was implanted with a 23 gauge needle for the administration of drugs.

Following all surgical procedures, rabbits were allowed to rest for 10 minutes during which intracavernosal blood pressure (ICP) and mean arterial blood pressure (MABP) were continuously recorded.

Drugs at various concentrations were prepared as aqueous solution (injection volume of 200 μL). Following drug injection the tubing was flushed with 100 μL distilled water. All drug treatments were administered after stable intracavernosal and systemic blood pressures were established. If an increase in intracavernosal blood pressure (ICP) was observed, the effect was monitored throughout its entire duration. Animals that did not exhibit an increase in ICP received an injection of a combination of phentolamine (0.2 mg) and papaverine (6.0 mg) to confirm the accuracy of needle implantation and to evaluate the erectile responsiveness of the animal. Animals that did not respond to this combination were disregarded from the analysis.

The following parameters were obtained from each experimental recording: (i) Maximum ICP (mm Hg), (ii) Duration (minutes), defined as the time in minutes, that the increase in ICP is greater than the 50% difference between baseline and maximum response. Data were analyzed using ANOVA statistical analysis (p<0.05).

Figure 8:
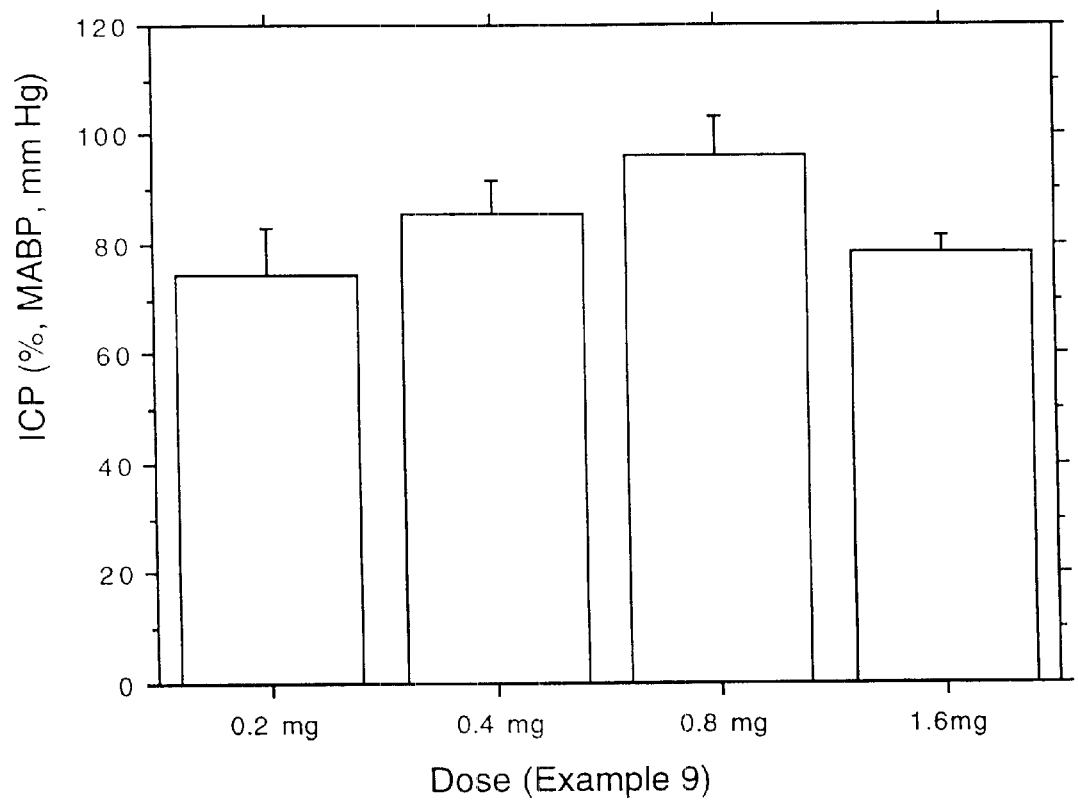
FIG. 8 shows the percent peak erectile response in vivo, expressed as intercavemosal pressure (ICP) as a percent of the mean arterial blood pressure (% MABP) in the anesthetized rabbit following the intracavemosal injection of various doses of Example 9 (0.2 mg, 0.4 mg, 0.8 mg and 1.6 mg). The ordinate is the percent response of intracavernosal pressure and the abscissa indicates the various doses of Example 9 given.

FIG. 8 shows the peak erectile response in vivo in the anesthetized rabbit following the intracavernosal administration of various doses of Example 9 (0.2 mg, 0.4 mg, 0.8 mg and 1.6 mg).

Figure 9:
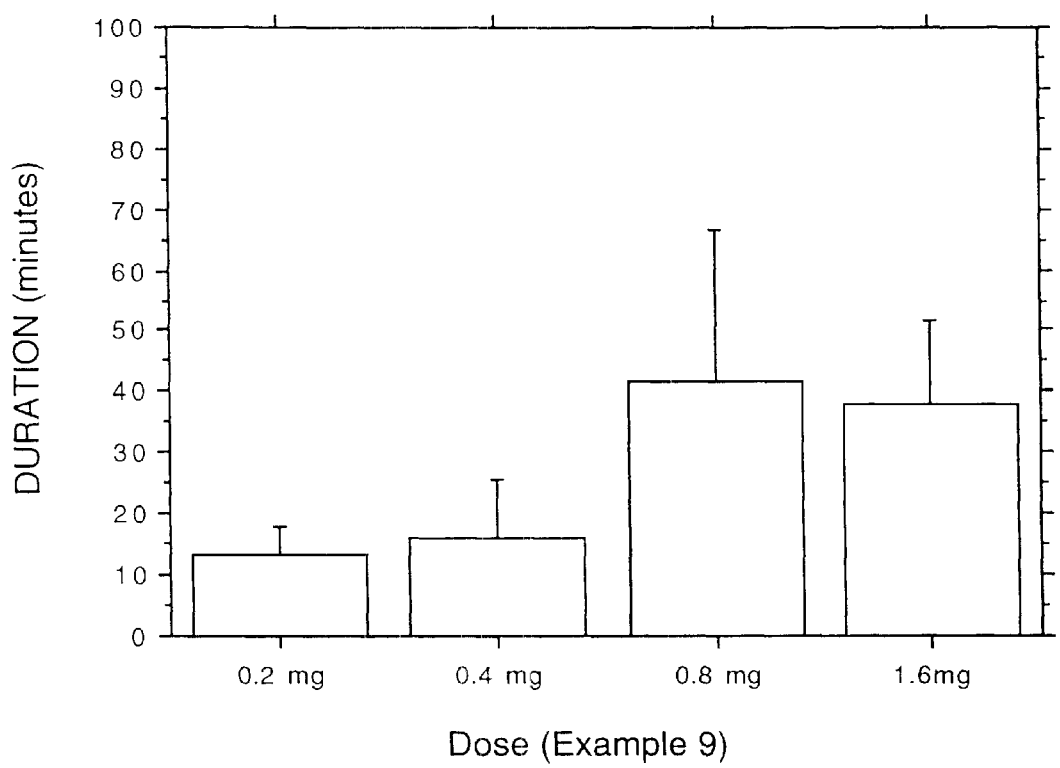
FIG. 9 shows the duration of the erectile response in vivo in the anesthetized rabbit upon intracavernosal administration of Example 9 (0.2 mg, 0.4 mg, 0.8 mg and 1.6 mg). The ordinate is the duration in minutes and the abscissa indicates the various doses of Example 9 (0.2 mg, 0.4 mg, 0.8 mg and 1.6 mg).

FIG. 9 shows the duration of the erectile response in vivo in the anesthetized rabbit upon intracavernosal administration of various doses of Example 9 (0.2 mg, 0.4 mg, 0.8 mg and 1.6 mg).

Figure 10:
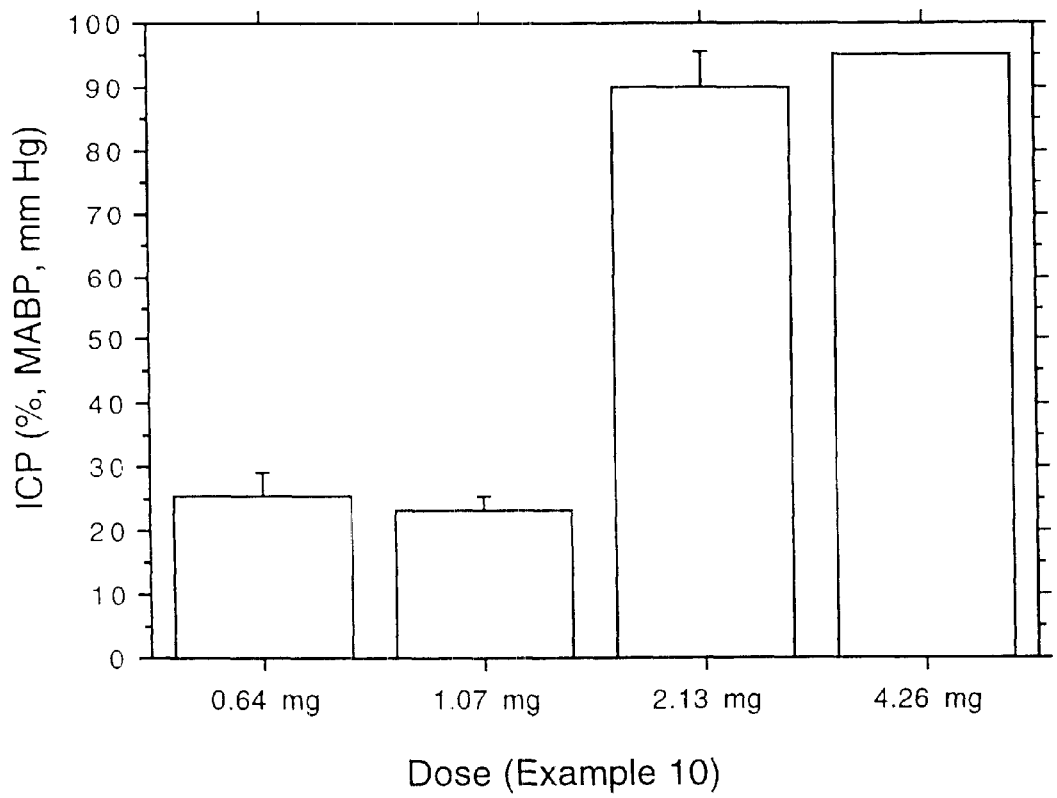
FIG. 10 shows the percent peak erectile response in vivo, expressed as intercavernosal pressure (ICP) as a percent of the mean arterial blood pressure (% MABP) in the anesthetized rabbit following the intracavemosal injection of Example 10 (0.64 mg, 1.07 mg, 2.13 mg and 4.26 mg). The ordinate is the percent response of intracavernosal pressure and the abscissa indicates the doses of Example 10.

FIG. 10 shows the peak erectile response in vivo in the anesthetized rabbit following the intracavernosal administration of various doses of Example 10 (0.64 mg, 1.07 mg, 2.13 mg and 4.26 mg).

Figure 11:
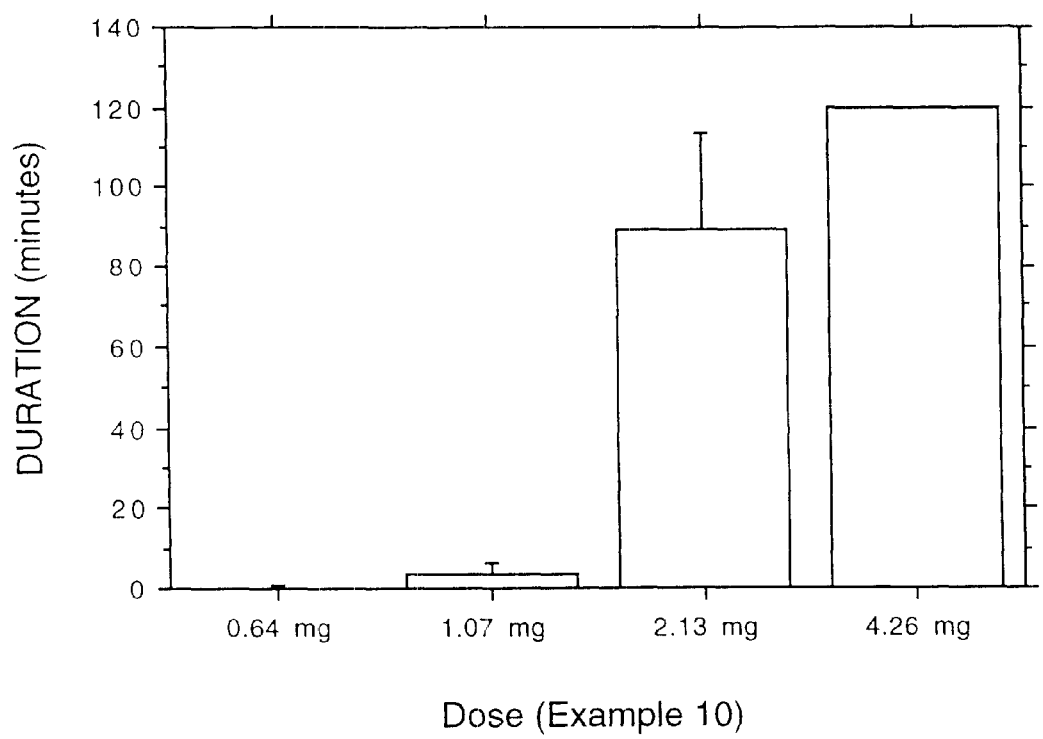
FIG. 11 shows the duration of the erectile response in vivo in the anesthetized rabbit upon intracavernosal administration of Example 10 (0.64 mg, 1.07 mg, 2.13 mg and 4.26 mg). The ordinate is the duration in minutes and the abscissa indicates the doses of Example 10 given.

FIG. 11 shows the duration of the erectile response in vivo in the anesthetized rabbit upon intracavernosal administration of various doses of Example 10 (0.64 mg, 1.07 mg, 2.13 mg and 4.26 mg).

FIG. 10 and FIG. 11 show that 1.07 mg of Example 10 produces a moderate and short-lasting increase of ICP. At 2.13 mg and 4.26 mg of Example 10 a robust effect on both the magnitude and duration of increase in intracavernosal pressure was observed. At 4.26 mg, the duration of the erectile response exceeded 120 minutes. FIG. 8 to FIG. 11 show that the doses of Example 9 needed to produce a robust increase of ICP is lower than the doses of Example 10. At the doses of Example 9, the duration of the erectile was somewhat shorter than that of Example 10.

Each of the publications, patents and patent applications described herein is hereby incorporated by reference herein in their entirety.

Various modifications of the invention, in addition to those described herein, will be apparent to one skilled in the art from the foregoing description. Such modifications are also intended to fall within the scope of the appended claims.

What is claimed is:

1. A compound of formula (VIII):

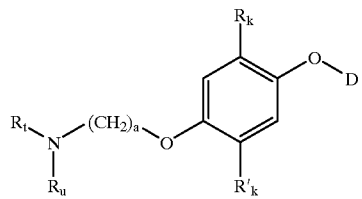

VIII wherein $R_t$ and $R_u$ are each independently a hydrogen, a lower alkyl, a cycloalkyl, or an aryl;

$R_k$ is hydrogen or a lower alkyl;

$R'_k$ is a lower alkyl;

a is an integer of 2 or 3;

D is:
 (i) —NO;
 (ii) —NO$_2$; or
 (iii) —C($R_d$)—O—C(O)—Y—Z—(C($R_e$)($R_f$))$_p$—T—Q;

$R_d$ is a hydrogen, a lower alkyl, a cycloalkyl, an aryl or an arylalkyl;

Y is oxygen, sulfur or NR$_i$;

$R_i$ is a hydrogen or a lower alkyl;

$R_e$ and $R_f$ are each independently a hydrogen, a lower alkyl, a cycloalkyl, amido, alkyl amido, an amino, an alkylamino, an aryl, an arylalkyl, a carboxyl, or $R_e$ and $R_f$ taken together with the carbon atoms to which they are attached are a carbonyl, a cycloalkyl group or a bridged cycloalkyl group;

p is an integer from 1 to 6;

T is independently a covalent bond, oxygen, sulfur or nitrogen;

Z is a covalent bond, a lower alkyl, a cycloalkyl, an aryl, or an arylalkyl; and Q is —NO or —NO$_2$.

2. A composition comprising the compound of claim 1 and a pharmaceutically acceptable carrier.

3. The compound of claim 1, wherein the compound of formula VIII is a nitrosated moxisylyte.

4. The compound of claim 1, wherein the compound of formula VIII is a nitrosylated moxisylyte.

5. The compound of claim 1, wherein the compound of formula VIII is 4-(2-(dimethylamino)ethoxy)-2-methyl-5-(methylethyl)phenyl 3-methyl-3-(nitrosothio) butanoate, or a pharmaceutically acceptable salt thereof.

6. A kit comprising at least one compound of claim 1.

7. The kit of claim 6, further comprising a pharmaceutically acceptable carrier.

8. A kit comprising at least one compound of claim 5.

9. The kit of claim 8, further comprising a pharmaceutically acceptable carrier.

10. A compound of formula (VIIIa), or a pharmaceutically acceptable salt thereof:

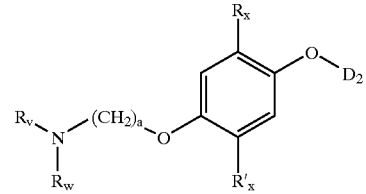

VIIIa wherein a is an integer of 2 or 3;

$R_v$ and $R_w$ are each independently a hydrogen, a lower alkyl, a cycloalkyl, an aryl, or $R_v$ and $R_w$ when taken together with the nitrogen atom to which they are attached are a heterocyclic ring;

$R_x$ is hydrogen or lower alkyl;

$R'_x$ is independently selected from $R_x$;

$D_2$ is:
 (i) —C(O)—Y$_l$—Z$_1$—(G—(C($R_y$)($R_z$))$_{q'}$—T$_f$—Q)$_p$;
 (ii) —P—Z$_1$—(G—(C($R_y$)($R_z$))$_{q'}$—T$_f$—Q)$_p$;
 (iii) —P—B$_1$—V—B$_t$—K$_r$—E$_s$—(C($R_y$)($R_z$))$_w$—E$_c$—(C($R_y$)($R_z$))$_x$—K$_d$—(C($R_y$)($R_z$))$_y$—K$_i$—E$_j$—K$_g$—(C($R_y$)($R_z$))$_z$—T$_f$—Q; or
 (iv) —P—F'$_n$—K$_r$—E$_s$—(C($R_y$)($R_z$))$_w$—E$_c$—(C($R_y$)($R_z$))$_x$—K$_d$—(C($R_y$)($R_z$))$_y$—K$_i$—E$_j$—K$_g$—(C($R_y$)($R_z$))$_z$—T$_f$—Q;

$Y_l$ is oxygen, S(O)$_o$, lower alkyl or NR'$_i$;

o is an integer from 0 to 2;

R'$_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, —$CH_2$—$C(T_f$—$Q)(R_y)(R_z)$, or —$(N_2O_2^-).M^+$, wherein $M^+$ in an organic or inorganic cation;

$R_y$ and $R_z$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, —$T_f$—Q, or $(C(R_y)(R_z))_k$—$T_f$—Q, or $R_y$ and $R_z$ taken together with the carbon atoms to which they are attached are a carbonyl, a methanthial, a heterocyclic ring, a cycloalkyl group or a bridged cycloalkyl group;

k is an integer from 1 to 3;

$T_f$ is independently a covalent bond, oxygen, $S(O)_o$ or $NR_i$;

$Z_f$ is a covalent bond, an alkyl, an aryl, an alkylaryl, an arylalkyl, a heteroalkyl, or $(C(R_y)(R_z))_p$;

G is a covalent bond, —$T_f$—C(O)—, —C(O)—$T_f$— or $T_f$;

q' is an integer from 0 to 5;

P is a carbonyl, a phosphoryl or a silyl;

l and t are each independently an integer from 1 to 3;

r, s, c, d, g, i and j are each independently an integer from 0 to 3;

w, x, y and z are each independently an integer from 0 to 10;

p is an integer from 1 to 10;

B at each occurrence is independently an alkyl, an aryl, or $(C(R_y)(R_z))_p$;

E at each occurrence is independently —Ti—, an alkyl, an aryl, or —$(CH_2CH_2O)q$;

K at each occurrence is independently —C(O)—, —C(S)—, —$T_f$—, a heterocyclic ring, an aryl, an alkenyl, an alkynyl, an arylheterocyclic ring, or —$(CH_2CH_2O)_q$;

q is an integer of from 1 to 5;

V is oxygen, $S(O)_o$, or $NR'_i$;

F' at each occurrence is independently B or carbonyl;

n is an integer from 2 to 5; and

Q is —NO or —$NO_2$;

with the proviso that when $R'_i$ is —$CH_2$—$C(T_f$—$Q)(R_y)(R_z)$ or —$(N_2O_2^-).M^-$, or $R_y$ or $R_z$ are $T_f$—Q, or $(C(R_y)(R_z))_k$—$T_f$—Q then the "—$T_f$—Q" subgroup designated in D can be a hydrogen, an alkyl, an alkoxy, an alkoxyalkyl, an aminoalkyl, a hydroxy, or an aryl.

11. A composition comprising the compound of claim 10 and a pharmaceutically acceptable carrier.

12. The compound of claim 10, wherein the compound of formula VIIIa is a nitrosated moxisylyte.

13. The compound of claim 10, wherein the compound of formula VIIIa is a nitrosylated moxisylyte.

14. The compound of claim 10, wherein the compound of formula VIII is a nitrosated and nitrosylated moxisylyte.

15. The compound of claim 10, wherein the compound of formula VIIIa is 4-(2-(dimethylamino)ethoxy)-2-methyl-5-(methylethyl)phenyl 4-(N-(((nitrosothio)cyclohexyl)methyl)carbamoyl)butanoate, 4-(2-(dimethylamino)ethoxy)-2-methyl-5-(methylethyl)phenyl 2-((N-(2-methyl-2-(nitrosothio)propyl)carbamoyl)methoxy)acetate, 4-(2-(dimethylamino)ethoxy)-2-methyl-5-(methylethyl)phenyl 2-(2-(nitrosothio)adamantan-2-yl)ethyl butane-1,4-dioate, 4-(2-(dimethylamino)ethoxy)-2-methyl-5-(methylethyl) phenyl 2-(((2-(2-(nitrosothio)adamantan-2-yl)ethyl)oxycarbonyl)methoxy)acetate, 4-(2-(dimethylamino)ethoxy)-2-methyl-5-(methylethyl)phenyl 2-(2-(nitrosothio)adamantan-2-yl)ethyl pentane-1,5-dioate, 4-(2-(dimethylamino)ethoxy)-2-methyl-5-(methylethyl)phenyl 4-(N-(2-methyl-2-(nitrosothio)propyl)carbamoyl)butanoate, 4-(2-(dimethylamino)ethoxy)-2-methyl-5-(methylethyl) phenyl 4-(N-methyl-N-(2-methyl-2-(nitrosothio)propyl)carbamoyl)butanoate, 4-(2-(dimethylamino)ethoxy)-2-methyl-5-(methylethyl)phenyl 5-(4-(2-methyl-2-(nitrosothio)propyl)piperazinyl)-5-oxopentanoate, 4-(2-(dimethylamino)ethoxy)-2-methyl-5-(methylethyl)phenyl 2-(2-(N-(2-methyl-2-(nitrosothio)propyl)carbamoyl)phenyl)benzoate, 4-(2-(dimethylamino)ethoxy)-2-methyl-5-(methylethyl)phenyl 1-(3-methyl-3-(nitrosothio)butanoyl)piperidine-4-carboxylate, 4-(2-(dimethylamino)ethoxy)-2-methyl-5-(methylethyl)phenyl 2,2-bis((nitrooxy)methyl)-3-(nitrooxy)propyl pentane-1,5-dioate, or a pharmaceutically acceptable salt thereof.

16. A kit comprising at least one compound of claim 10.

17. The kit of claim 16, further comprising a pharmaceutically acceptable carrier.

18. A kit comprising at least one compound of claim 15.

19. The kit of claim 18, further comprising a pharmaceutically acceptable carrier.

* * * * *

UNITED STATES PATENT AND TRADEMARK OFFICE
CERTIFICATE OF CORRECTION

PATENT NO. : 6,469,065 B1
DATED : October 22, 2003
INVENTOR(S) : Garvey et al.

It is certified that error appears in the above-identified patent and that said Letters Patent is hereby corrected as shown below:

<u>Title page, Item [54] and Column 1, line 1,</u>
Delete "ANTAGONIST" and insert -- ANTAGONISTS --

<u>Title page,</u>
Item [75], Inventors, add -- Subhash K. Khanapure, Clinton, MA (US) --

<u>Column 4,</u>
Line 46, delete "cc" and insert -- α --.
Line 53, delete "no"

<u>Column 5,</u>
Lines 11, 14, 48, 50, 59 and 61, delete "intracavemosal" and insert -- intracavernosal --
Line 11, delete "$\mu$p" and insert -- $\mu$g --

<u>Column 6,</u>
Line 8, delete "intracavemosal" and insert -- intracavernosal --
Line 22, delete "antagonists" and insert -- antagonist --

<u>Column 11,</u>
Line 41, delete "piperizines" and insert -- piperazines --
Line 51, delete "is"

<u>Column 44,</u>
Line 5, delete "adenosin" and insert -- adenosine --

<u>Column 49,</u>
Line 11, delete "3-methyl" and insert -- (3- --

<u>Column 66,</u>
Line 55, delete "dimethylthiirane" and insert -- dimethylthirane --

UNITED STATES PATENT AND TRADEMARK OFFICE
CERTIFICATE OF CORRECTION

PATENT NO.   : 6,469,065 B1
DATED        : October 22, 2003
INVENTOR(S)  : Garvey et al.

It is certified that error appears in the above-identified patent and that said Letters Patent is hereby corrected as shown below:

<u>Column 73,</u>
Line 11, delete "intracavemosal" and insert -- intracavernosal --

Signed and Sealed this

Ninth Day of September, 2003

JAMES E. ROGAN
*Director of the United States Patent and Trademark Office*